(12) United States Patent
Bonacchi et al.

(10) Patent No.: US 8,771,642 B2
(45) Date of Patent: Jul. 8, 2014

(54) ACTIVE PARTICLES FOR BIO-ANALYTICAL APPLICATIONS AND METHODS FOR THEIR PREPARATION

(75) Inventors: Sara Bonacchi, Pistoia (IT); Riccardo Juris, Bologna (IT); Marco Montalti, Calderara di Reno (IT); Luca Prodi, Bologna (IT); Enrico Rampazzo, Bologna (IT); Nelsi Zaccheroni, Bologna (IT)

(73) Assignee: Alma Mater Studiorum—Universita' Di Bologna, Bologna (IT)

( * ) Notice: Subject to any disclaimer, the term of this patent is extended or adjusted under 35 U.S.C. 154(b) by 265 days.

(21) Appl. No.: 13/056,752

(22) PCT Filed: Jul. 31, 2009

(86) PCT No.: PCT/IB2009/006432
§ 371 (c)(1),
(2), (4) Date: Jul. 28, 2011

(87) PCT Pub. No.: WO2010/013136
PCT Pub. Date: Feb. 4, 2010

(65) Prior Publication Data
US 2011/0274621 A1    Nov. 10, 2011

(30) Foreign Application Priority Data

Jul. 31, 2008  (IT) .............................. BO2008A0485
Jul. 31, 2008  (IT) .............................. BO2008A0486

(51) Int. Cl.
*A61K 49/00*    (2006.01)
*A61K 9/16*     (2006.01)
*A01N 55/00*    (2006.01)

(52) U.S. Cl.
USPC .............................. 424/9.1; 424/490; 514/63

(58) Field of Classification Search
None
See application file for complete search history.

(56) References Cited

U.S. PATENT DOCUMENTS

2005/0085619 A1* 4/2005  Wilson ........................... 528/405
2006/0142506 A1* 6/2006  Breitenkamp et al. ......... 525/482
2008/0226741 A1* 9/2008  Richard ......................... 424/501

FOREIGN PATENT DOCUMENTS

CN        101224187 A      7/2008
WO    WO-2007064297 A1    6/2007

OTHER PUBLICATIONS

Heredia, K.L., et al., "Synthesis of protein-polymer conjugates", 2006, Organic & Biomolecular Chemistry, pp. 45-53.*
Yang, W., et al., "Novel fluorescent silica nanoparticle probe for ultrasensitive immunoassays", 2004, Analytica Chimica Acta, pp. 163-169.*
Huo, Q., et al., "A New Class of Silica Cross-Linked Micellar Core-Shell Nanoparticles," *J. A. Chem. Soc.*, vol. 128, No. 19 (2006), pp. 6447-6453.
Huang, K., et al., "Synthesis and Characterization of Self-Assembling Block Copolymers Containing Adhesive Moieties," *Polymer Preprints*, vol. 42, No. 2 (2001), pp. 147-148.
Gigout, A., et al., "The Fate of Pluronic F-68 in Chondrocytes and CHO Cells," *Biotechnology and Bioengineering*, vol. 100, No. 5, (Feb. 11, 2008), pp. 975-987.
Byron, P. M., et al., "Poloxamer-Mediated Functionalization of Bioanalytical Surfaces—The Role of Nanoparticles as Model Surfaces," *Current Organic Chemistry*, Hilversum, NL, vol. 9, No. 11 (Jan. 1, 2005), pp. 1085-1098.
International Search Report in PCT Application No. PCT/IB2009/006432, dated Oct. 21, 2010.
Momose, Isao, et al., "Melleolides K, L and M, New Melleolides from *Armillariella mellea*," *The Journal of Antibiotics*, 2000, vol. 53, No. 2, pp. 137-143.
Chinese Office Action dated Nov. 4, 2013, in counterpart foreign patent application No. CN 2009/80137512.

* cited by examiner

*Primary Examiner* — Michael G Hartley
*Assistant Examiner* — Lance Rider
(74) *Attorney, Agent, or Firm* — Marshall, Gerstein & Borun LLP

(57) ABSTRACT

Nanoparticles, which are luminescent and/or electroactive and/or suitable for MRI (magnetic resonance imaging and/or PET (positron emission tomography) applications, comprise a micelle, which has a hydrophilic shell and an hydrophobic central portion, and a polysilicate core; the micelle comprises a plurality of molecules of a functionalized surfactant having the following structure: $M^1$-Hydro$^1$-Lipo-Hydro$^2$-$M^2$ wherein Lipo indicates a hydrophobic chain; Hydro1 ed Hydro$^2$ indicate, each, a respective hydrophilic chain; $M^1$ ed $M^2$ represent respective recognition functionalities.

16 Claims, 19 Drawing Sheets

ACTIVE PARTICLES FOR BIO-ANALYTICAL APPLICATIONS AND METHODS FOR THEIR PREPARATION

CROSS-REFERENCE TO RELATED APPLICATIONS

This is the U.S. national phase application of International Application No. PCT/IB2009/006432, filed Jul. 31, 2009, which claims the benefit of Italian Patent Application No. BO2008A 000486, filed Jul. 31, 2008, and Italian Patent Application No. BO2008A 00485, filed Jul. 31, 2008.

TECHNICAL FIELD

The present invention relates to a particle, uses of such a particle and preparations comprising such a particle. The present invention, moreover, relates to a procedure and to methods for the preparation of this particle.

BACKGROUND ART

In the bio-analytical field, up to now, there is a very severe need of identifying new diagnostic tools, and in particular particles to be used in applications for the detection, labelling and imaging of bio-molecules. It is nowadays also very urgent the need of making available new tools for treatments in phototherapy.

At the state of the art particles are known for drug delivery (for example *A New Class Of Silica Cross-Linked Micellar Core-Shell Nanoparticles*; Huo, Q.; Liu, J.; Wang, L. Q.; Jiang, Y.; Lambert, T. N.; Fang, E. *J. Am. Chem. Soc.* 2006, 128(19), 6447-6453). This kind of particles are nevertheless hardly suitable for diagnostic applications (and/or phototherapy) since they are not engineered to target specific positions and they present a high tendency to release the drugs or active substances that they contain. The methods for the preparation of these particles are, moreover, in many cases very time demanding.

For what stated above one can gather that there is a great need of making available new particles and new methods for their preparation.

DISCLOSURE OF INVENTION

Aim of the present invention is that to provide a particle, a procedure and methods for the preparation of a particle that allow to overcome, at least partially, the drawbacks of the known state of the art, and that, meanwhile, are of easy and cheap realization.

Aim of the present invention is also to provide uses of the aforementioned particle and preparations comprising the mentioned particle.

According to the present invention, a particle, a procedure and methods for the preparation of a particle, uses of this particle and preparations comprising this particle are provided as recited in the independent claims that follow and, preferably, in any of the dependent claims depending directly or indirectly on the independent claims.

Unless explicitly specified otherwise, the following terms have the meaning reported hereinafter.

Active compound (or particle) means a compound (or particle), in particular an organic or metallo-organic one, that is emissive, and/or electroactive, and/or a contrast agent, and/or able to emit positrons.

Emitting compound (or particle) means a compound (or particle), able to emit energy, preferably as detectable electromagnetic radiations (luminescent compound or particle) or as heat. The emitting compound can be able to emit by its own and/or in combination with at least a second emitting compound; even through appropriate processes of energy transfer in between luminescent species; the emission can take place through fluorescence, phosphorescence, electrochemiluminescence (ECL) processes or through chemiluminescence reactions.

An emitting compound can be fluorescent or luminescent. A luminescent compound is, in particular, either phosphorescent or electrochemiluminescent.

Electrochemiluminescent compound means a compound that when involved in a redox process is able to emit detectable electromagnetic radiations.

Electroactive species (compounds or particles) mean chemical species able to take part in redox processes that can be exploited for analytical detection purposes, or that take part in energy transfer processes with other luminescent species.

Contrast species (compounds or particles) mean species that are suitable for MRI (magnetic resonance imaging) applications.

Particles mean objects with an average hydrodynamic diameter in water less than 500 nm.

Average hydrodynamic diameter means the average diameter of particles so as determined in a dispersion of particles in a solvent via DLS (dynamic light scattering).

In the present text $C_x$-$C_y$ refers to a group having from x to y carbon atoms.

In the present text aliphatic means a hydrocarbon that is non aromatic and non substituted and is saturated or non saturated, linear, branched and/or cyclic. Non limitative examples of aliphatic groups are: t-buthyl, ethenyl, ethyl, 1-o 2-propenyl, n-propyl, 2-propyl, cyclohexyl, cyclohexenyl.

In the present text alkyl means a saturated aliphatic (i.e. an aliphatic group without double or triple carbon-carbon bonds). Non limitative examples of alkyls are: methyl, ethyl, n-propyl, t-butyl, cyclohexyl.

In the present text alkoxy means an aliphatic (preferably an aliphatic $C_1$-$C_5$, advantageously an alkyl $C_1$-$C_4$) bound to the rest of the molecule through an oxygen atom. Non limitative examples of alkoxy are: methoxy, ethoxy.

Alkoxy-silane functionality means a molecular portion that has the structure Si—O—$R^a$, in which $R^a$ indicates an alkyl $C_1$-$C_4$, advantageously an alkyl $C_1$-$C_2$, in particular an ethyl.

Trialkoxysilane means a molecule that has three alkoxysilane functionalities (i.e. functional groups), in which the three alkoxy groups of the alkoxy-silane functionalities are bound to the same silicon atom.

Tetraalkoxysilane means a molecule that has four alkoxysilane functionalities, in which the four alkoxy groups of the alkoxy-silane functionalities are bound to the same silicon atom. The Tetraethoxysilane (TEOS) is an example of tetraalkoxysilane.

Substantially hydrophilic chain means a chain that has a water solubility higher than the water solubility of a substantially hydrophobic chain. Advantageously, the substantially hydrophilic chain has a higher solubility in water than in ethanol.

Substantially hydrophobic chain means a chain that has a water solubility lower than the water solubility of a substantially hydrophilic chain. Advantageously, the substantially hydrophobic chain is substantially lipophilic.

Substantially lipophilic molecular portion (or chain or compound) means a molecular portion (or chain or compound) that has a higher solubility in ethanol than in water.

To silanize means to perform a process of hydrolysis-condensation that involves at least a part of the alkoxy-silane functionalities that are hydrolyzed to silanols and that form, through condensation reactions, siloxane bridge bonds (i.e. Si—O—Si), that, advantageously, take to the formation of a matrix. For merely illustrative purposes, FIG. 1 schematically shows the reactions that take place when the TEOS (tetraethyl orthosilicate or tetraethoxysilane) undergoes a condensation reaction.

Aqueous solution means a solution in which the majority solvent is water. Advantageously, in aqueous solution the only solvent is water.

Recognition functionality means a functionality able to bind a specific substrate or analyte. Advantageously, the substrate and/or the analyte is/are a bio-molecule.

In some advantageous embodiments, the recognition functionality includes a recognition bio-molecule bound to the rest of the molecule, specifically a surfactant, through a bridging bond. In some embodiments, the binding bridge is chosen among the group consisting of:

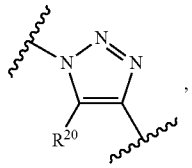

amide (in particular, presenting a structure chosen among the group consisting of: —OR$^{17}$CONH—, —OR$^{18}$CONH—, —CONH—, —OCOR$^{19}$CONH—, in which R$^{17}$, R$^{18}$, R$^{19}$ and R$^{20}$ are defined as reported hereafter).

Bio-molecule means a molecule that is involved in the maintenance and/or in the metabolic processes of the living organism. In some embodiments, the bio-molecule is chosen among the group consisting of: carbohydrates (in particular saccharidic molecules), lipids, proteins, glycoproteins, nucleic acids, peptide nucleic acids, hormones, vitamins. Specific examples of bio-molecules are: avidin, streptavidin, biotin.

Recognition bio-molecule means a bio-molecule or a portion of a bio-molecule. In some embodiments, the recognition bio-molecule is chosen in the group consisting of: proteins, single chain nucleic acids, peptide nucleic acids, hormones, vitamins. Advantageously, the recognition bio-molecule is chosen in the group consisting of: peptides (advantageously, polypeptides and oligopeptides), oligonucleotides, avidin, streptavidin, biotin, monoclonal antibodies, polyclonal antibodies.

Oligonucleotide means a chain no longer than fifty nucleotides. In particular, oligonucleotide means a chain no longer than twenty nucleotides.

Oligopeptide means a peptidic chain no longer than thirty amino acids. In particular, oligopeptide means a peptidic chain no longer than thirty amino acids.

Polypeptide means a peptidic chain longer than thirty amino acids and no longer than three hundreds amino acids. In particular, polypeptide means a peptidic chain longer than thirty amino acids and no longer than three hundreds of amino acids.

If not explicitly specified the contrary, the references (articles, texts, patents applications, etc.) cited in this text is herein referred to in full for the sake of completeness of description. In particular, the mentioned references are herein incorporated by reference.

BRIEF DESCRIPTION OF THE DRAWINGS

The invention will be hereby described with reference to the attached figures, which illustrate some non limiting embodiments.

EMBODIMENTS OF THE INVENTION

Functionalized Particles

Figure 1:
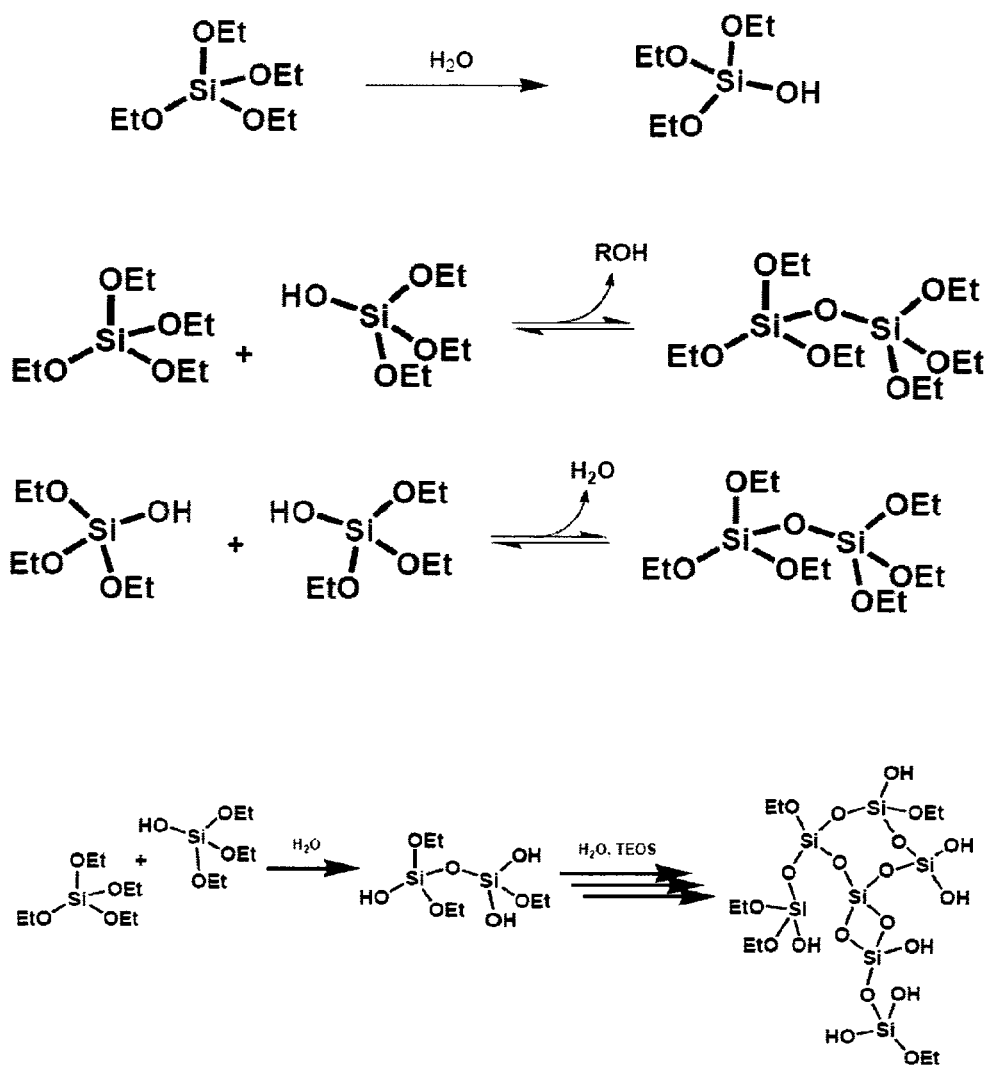
FIG. 1 shows schematically the reactions that take place during the silanization of TEOS.

In accordance with a first aspect of the present invention, it is provided a particle which comprises a micelle, that in turn has a shell (i.e. a part oriented towards the exterior) substantially hydrophilic and an inner part substantially hydrophobic; and a core, which is located in the area of the inner part of the micelle and comprises a silicate network; and at least one active compound. The micelle comprises several molecules of at least one surfactant; these molecules comprise at least one functionalized surfactant molecule, which has the following structure:

$M^1$-Hydro$^1$-Lipo-Hydro$^2$-$M^2$ wherein Lipo indicates a substantially hydrophobic chain, Hydro$^1$ and Hydro$^2$ indicate, independently of each other, a substantially hydrophilic chain, $M^1$ is chosen in the group consisting of: a recognition functionality and a heterogroup; $M^2$ is chosen among the group consisting of: —H, —OH, a recognition functionality and a heterogroup.

In this text, by micelles it is meant either micellar aggregates (comprising molecules of only one kind of surfactants) or micellar co-aggregates (comprising molecules of many kinds of surfactants).

According to some embodiments, micelles are micellar aggregates. In particular, the particles are essentially spherical in shape.

According to some embodiments, APTES is not an active compound as previously defined.

According to some embodiments, $M^1$ represents a recognition functionality. In some embodiments, $M^2$ is chosen among the group consisting of: —H, —OH, a recognition functionality and a heterogroup. In some embodiments, $M^2$ is chosen among the group consisting of: —H, —OH, a recognition functionality (advantageously, $M^2$ represents a recognition functionality).

By heterogroup it is meant a substituent that differs from the components of Hydro$^1$ and Hydro$^2$ and presents at least one heteroatom and/or at least one unsaturated bond. Heterogroups can function as intermediate groups, that, through a reaction, are substituted with or bind a recognition functionality.

Advantageously, the heterogroup is chosen among a group consisting of: —OCO(CH$_2$)$_2$COOH, —SH, —N$_3$, —C≡CH, —SO$_3$Na, —(CH$_2$)$_3$—SO$_3$Na—, —SO$_3$CH$_3$, —OPO$_3$H$_2$, —COOH, —OCH$_2$COOH.

In some specific embodiments, the heterogroup is chosen among the group consisting of: —NH$_2$, —OCO(CH$_2$)$_2$COOH, —SH, —N$_3$, —SO$_3$CH$_3$, —OCH$_2$COOH, —COOH.

According to some specific embodiments, $M^1$ and $M^2$ are chosen, each one independently from the other, in a group consisting of: —H, —OH, a recognition functionality comprising a recognition bio-molecule; at least one of $M^1$ and $M^2$ being a recognition functionality comprising a recognition bio-molecule.

In some particular embodiments, when $M^1$ comprises a recognition bio-molecule, $M^1$ has the following structure:

$RBM^1$-$BL^1$-, wherein $RBM^1$ represents a recognition bio-molecule, $BL^1$ represents a bridge linker, which is, advantageously, chosen in the group consisting of:

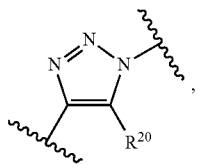

amide (in particular, having a structure chosen in the group consisting of: —NHCO— or —NHCOR$^{19}$COO—, wherein $R^{19}$ is as defined below; advantageously, —NHCO—).

When $M^2$ consists of a recognition bio-molecule, $M^2$ has the following structure:

-$BL^2$-$RBM^2$ wherein $RBM^2$ represents a recognition bio-molecule, $BL^2$ represents a bridge linker, which is, advantageously, chosen in the group consisting of:

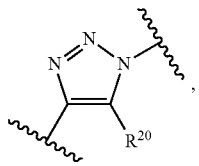

amide (in particular, having a structure chosen in the group consisting of: —OR$^{17}$CONH—, —OCOR$^{19}$CONH—, —NHCO—, wherein $R^{17}$ and $R^{19}$ are as defined below; advantageously, having the structure —OR$^{17}$CONH—).

$R^{20}$ is chosen in the group consisting of: —H, a linear alkyl, a cyclic alkyl, an aromatic ring, an heterogroup. In some embodiments, $R^{20}$ is chosen among the group consisting of: —H, a $C_1$-$C_4$ alkyl, an heterogroup. Advantageously, $R^{20}$ is chosen among the group consisting of: —H, a $C_1$-$C_4$ alkyl. In some specific embodiments, $R^{20}$ represents —H.

Advantageously, $M^1$ is a recognition functionality comprising a recognition bio-molecule chosen among the group consisting of: oligopeptides, polypeptides, oligonucleotides; $M^2$ is chosen among the group consisting of: —H, —OH, a recognition functionality consisting of a recognition bio-molecule chosen among the group consisting of: oligopeptides, polypeptides, oligonucleotides.

In some specific embodiments, the peptides are chosen among those described in the PCT patent application number WO2008064910.

During the synthesis of particles as above defined, wherein at least one among $M^1$ and $M^2$ represents a recognition functionality, it is advantageous to prepare "intermediate" particles that when modified (in particular through a chemical reaction) allow to obtain particles bearing at least one recognition functionality.

To this purpose, in some embodiments, $M^1$ is an heterogroup; $M^2$ is chosen among the group consisting of: —H, —OH and a heterogroup.

Advantageously, $M^1$ is chosen among the group consisting of: —NH$_2$, —OCOR$^{19}$COOH, —SH, —N$_3$, —C≡CH, —SO$_3$Na, —(CH$_2$)$_3$—SO$_3$Na, —SO$_3$CH$_3$, —OPO$_3$H$_2$, —COOH, —OR$^{18}$COOH. In some specific embodiments, $M^1$ is chosen among the group consisting of: —NH$_2$, —OCOR$^{19}$COOH, —SH, —N$_3$, —SO$_3$CH$_3$, —COOH. In some particularly advantageous embodiments, $M^1$ is chosen among the group consisting of: —OCOR$^{19}$COOH, —N$_3$, —COOH. In particular $M^1$ is chosen in the group consisting of: —N$_3$, —COOH.

In some embodiments, $R^{18}$ represents an alkyl $C_1$-$C_4$. Advantageously $R^{18}$ is a linear alkyl. In some particular embodiments, $R^{18}$ represents an alkyl $C_1$-$C_3$. In some specific embodiments, $R^{18}$ represents —CH$_2$—.

Advantageously, $M^2$ is chosen among the group consisting of: —H, —OH, —NH$_2$, —OCOR$^{19}$COOH, —SH, —N, —C≡CH, —SO$_3$Na, —(CH$_2$)$_3$—SO$_3$Na, —SO$_3$CH$_3$, —OPO$_3$H$_2$, —COOH, —OR$^{17}$COOH. In some specific embodiments, $M^2$ is chosen among the group consisting of: —H, —OH, —NH$_2$, —OCOR$^{19}$COOH, —SH, —N, —SO$_3$CH$_3$, —OR$^{17}$COOH. According to some particularly advantageous embodiments, $M^2$ is chosen among the group consisting of: —OCOR$^{19}$COOH, —N$_3$, —OR$^{17}$COOH. In particular, $M^2$ is chosen in the group consisting of: —N$_3$, —OR$^{17}$COOH.

According to some embodiments, $R^{17}$ represents an alkyl $C_1$-$C_4$. Advantageously $R^{17}$ is a linear alkyl. In some particular embodiments, $R^{17}$ represents an alkyl $C_1$-$C_3$. In some specific embodiments, $R^{17}$ represents —CH$_2$—.

According to some embodiments, $R^{19}$ represents an alkyl $C_1$-$C_4$. Advantageously, $R^{19}$ is a linear alkyl. In some particular embodiments, $R^{19}$ represents an alkyl $C_1$-$C_3$. In some specific embodiments, $R^{19}$ represents —(CH$_2$)$_2$—.

Advantageously, $M^1$ is the same as $M^2$; in particular, with the proviso that when $M^1$ is —COOH, $M^2$ is —OR$^{17}$COOH.

According to some embodiments, the active compound is located in the area of to the core. Advantageously, the active compound is an emitting compound. Advantageously, the active compound is luminescent or fluorescent.

In some embodiments, the active compound is a photoluminescent compound, i.e. a chemical species able to emit detectable electromagnetic radiations, advantageously with wavelength from 200 nm to 1500 nm, advantageously higher than 500 nm, advantageously from 550 nm to 1500 nm.

According to some embodiments, the active compound is covalently bound to the silicate network.

In some embodiments, the particle has an average hydrodynamic diameter in water smaller than circa 100 nm, advantageously from circa 40 to circa 10 nm.

In some embodiments, the core has a diameter smaller than 30 nm, in particular from circa 5 to circa 15 nm.

Advantageously, Lipo is substantially lipophilic. Hydro$^1$ and Hydro$^2$ are more soluble in water than in ethanol.

In some embodiments, Hydro¹ represents a chain

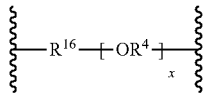

wherein $R^4$ is a linear alkyl $C_1$-$C_3$ (advantageously $C_2C_3$); Hydro² represents a chain

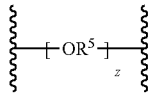

wherein $R^5$ is a linear alkyl $C_1$-$C_3$ (advantageously $C_2$-$C_3$); Lipo represents a chain

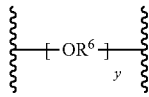

wherein $R^6$ is a branched alkyl $C_3$-$C_4$.

$R^{16}$ represents an alkyl $C_1$-$C_4$. According to some embodiments, $R^{16}$ is a linear alkyl $C_1$-$C_3$. In some specific embodiments, $R^{16}$ is chosen among the group consisting of: —$CH_2$— and —$(CH_2)_2$—.

In particular, when $M^1$ and $M^2$ are chosen in the group consisting of: —H, —OH, —$NH_2$, —$OCOR^{19}COOH$, —SH, —$N_3$, —C≡CH, —$SO_3Na$, —$(CH_2)_3$—$SO_3Na$, —$SO_3CH_3$, —$OPO_3H_2$, —$OR^{17}COOH$; $R^{16}$ represents —$(CH_2)_2$—. When $M^2$ represents —$OR^{17}COOH$ and $M^1$ represents —COOH, $R^{16}$ represents —$CH_2$—.

Advantageously, $R^4$ and $R^5$ represent, each one independently from the other, an ethyl. Advantageously, $R^6$ represents a branched propyl.

Advantageously, the surfactant is a block co-polymer ethylene oxide/propylene oxide.

In some embodiments, y is smaller or equal to x and z; x is from 40 to 130; z is from 40 to 130; y is from 20 to 85. Advantageously, x is from 55 to 130; z is from 55 to 130; y is from 35 to 85. Advantageously, x is from 80 to 120; z is from 80 to 120; y is from 50 to 80. Advantageously, x and z are from 90 to 110 and y is from 60 to 70.

Advantageously, represents a chain

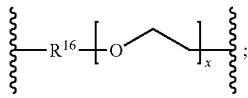

Hydro² represents a chain

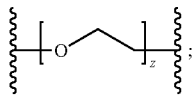

Lipo represents a chain

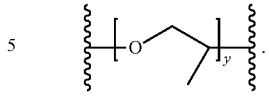

In some embodiments, the surfactant has an average molecular weight of at least 6 KDa, advantageously at least 10 KDa. In particular, the ratios between the average molecular weight of Lipo and the average molecular weight of Hydro¹ and between the average molecular weight of Lipo and the average molecular weight of Hydro² are each, independently from each other, from circa 0.4 to circa 0.2.

Advantageously, the surfactant presents an average molecular weight smaller than 15 KDa. Advantageously, the ratios z/y and x/y are, each, higher than circa 1.3 and smaller than circa 1.7.

According to some embodiments, molecules of surfactant comprise a non functionalized surfactant. Advantageously, the non functionalized surfactant has the following structure:

Hydro³-Lipo¹-Hydro⁴ in which Hydro², Hydro⁴, Lipo¹ are substantially defined as Hydro¹, Hydro² e Lipo.

According to some embodiments, the non functionalized surfactant is chosen is the group consisting of: Pluronic® F127, F98, P105, F68, F108, F88, F87.

According to some embodiments, the molar ratio of the non functionalized surfactant to the functionalized surfactant is smaller than 200/1. Advantageously, in particular, the molar ratio of the non functionalized surfactant to the functionalized surfactant is from 100/1 to 1/100 (advantageously 3/1).

Advantageously, the particle is obtainable in accordance with a method described in a second aspect of the present invention (hereinafter reported)

Advantageously, the particle is obtained in accordance with a method described in a second aspect of the present invention (hereinafter reported)

Preparation Methodology

In accordance with the second aspect of the present invention, it is provided a method for the preparation of an active nanoparticle, in particular as defined in accordance with the first aspect of the present invention, comprising a reaction step, during which several molecules of at least one alkoxysilane are silanized in presence of at least one active compound, of water and of a plurality of molecules of at least one functionalized surfactant; the alkoxysilane is chosen among a tetraalkoxysilane and a trialkoxysilane; the functionalized surfactant being as defined above with reference to the first aspect of the present invention.

According to a first group of embodiments, during the reaction step, the molecules of the alkoxysilane are silanized together with the active compound.

Figure 21:
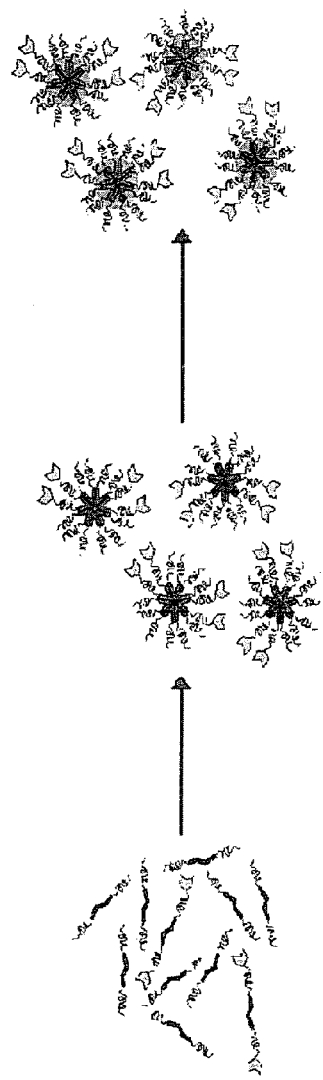
FIG. 21 shows schematically and for merely exemplificative purposes a method in accordance with the present invention.

FIG. 21 shows schematically, for merely exemplificative and non limiting purposes, the formation of particles (shown on the right): the surfactant molecules (or the surfactants molecules, shown on the left) in presence of water form micelles (shown in the middle); the alkoxysilane and the active compound silanize so as to form a core (shown on the right in the area of a central portion of the particles).

According to some embodiments, the reaction step takes place at a temperature from 10° C. to 60° C., advantageously from 20° C. to 50° C., advantageously from 25° C. to 40° C. In some embodiments, the reaction step takes place at a temperature from 10° C. to 80° C., advantageously from 15° C. to 60° C., advantageously from 20° C. to 30° C.

According to some embodiments, the active compound has the following structure:

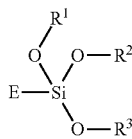

wherein E represents the portion of the molecule responsible for the activity of the active compound. Advantageously, $R^1$, $R^2$ and $R^3$ represent, each one independently from the other, an alkyl $C_1$-$C_4$, advantageously an alkyl $C_1$-$C_2$.

Figure 20:
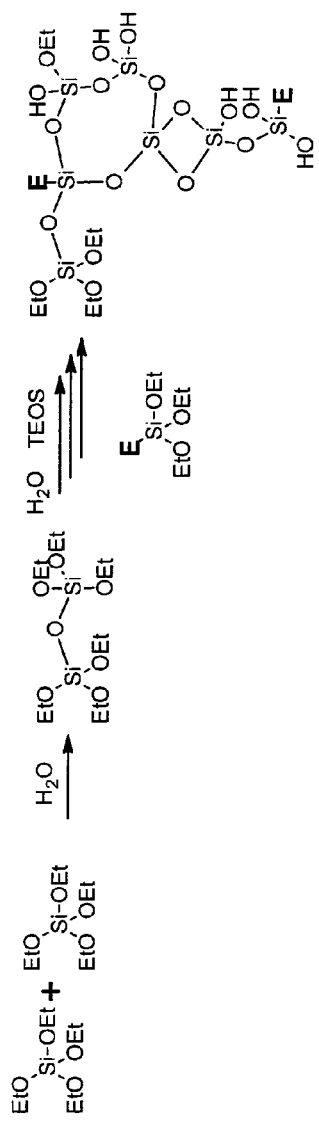
FIG. 20 shows schematically and for merely exemplificative purposes a step of a method in accordance with the present invention.

For merely exemplificative and non limiting purposes, FIG. 20 shows the reaction step, in which $R^1$, $R^2$ and $R^3$ represent each a respective ethyl.

According to embodiments, E is chosen in the group consisting of: dansyl, NBD (7-nitrobenzofurazan), rhodamine B, rhodamine B isothiocyanate, rhodamine B piperazine, 8-oxo-3-propylamino-8H-acenaphtho[1,2-b]pyrrol-9-carbonitrile, ferrocene derivatives, viologen derivatives, ruthenium complexes (for example, bis(2,2'-bipyridyl)-[4-(4'-methyl-2,2'-bipyridin-4-yl)butan-1-amine] Ru (II)), fullerene ($C_{60}$) derivatives, cyanines (Cy7; CY5; CY3) derivatives.

Cyanines are a family of luminescent compounds with a very wide structural variability.

In particular, closed chains cyanines present a structural formula that can be schematized as follows:

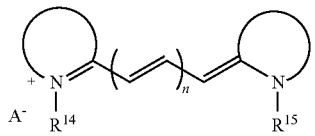

where A is advantageously Cl, Br, I or $ClO_4$. The two quaternary nitrogen atoms are inserted inside an heterocycle and are joint via a polymethinic chain; the polymethinic chain can be differently substituted.

The usual nomenclature distinguishes some subclasses that depend upon the number of the methinic groups present in the molecule.

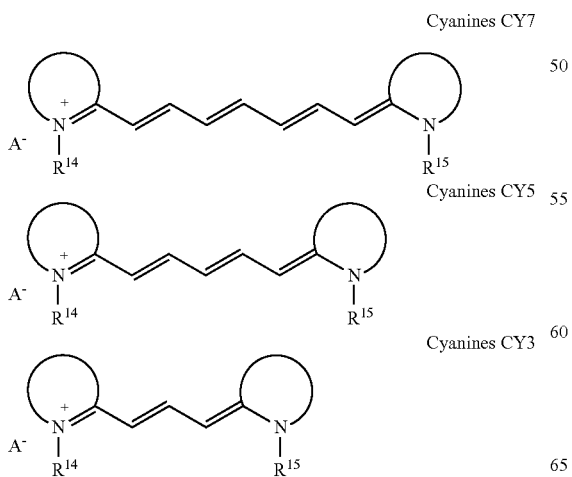

Cyanines CY7

Cyanines CY5

Cyanines CY3

Both the nitrogen atoms can be independently part of an heteroaromatic ring, as for example pyrrole, imidazole, thiazole, pyridine, quinoline, benzothiazole, indole, benzo[e]indole, benzo[cd]indole etc. More precisely, some examples of heterocycles are: dimethylindole, benzodimethyilindole (which presents 2 isomers, benzo[e] and benzo[cd]), benzoxazoles, benzothiazoles, benzimidazoles. Particularly important are the examples including the heterocycles: 1,1-dimethyl-3-(methyl)-indole, 1,1-dimethyl-3-(ethyl)-indole, 1,1-dimethyl-3-(methyl)-benzo[e]indole, 1,1-dimethyl-3-(ethyl)-benzo[e]indole. In this case the base structure can be schematized and rationalized as follows:

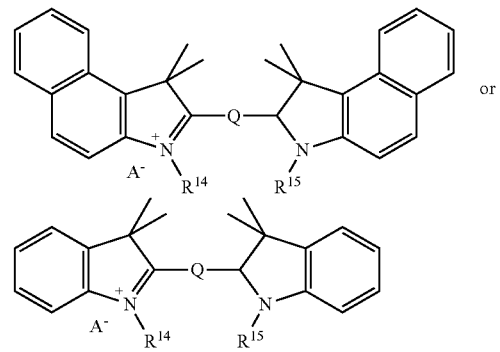

wherein A is advantageously Cl, Br, I or $ClO_4$, and the group Q is advantageously chosen among the group consisting of:

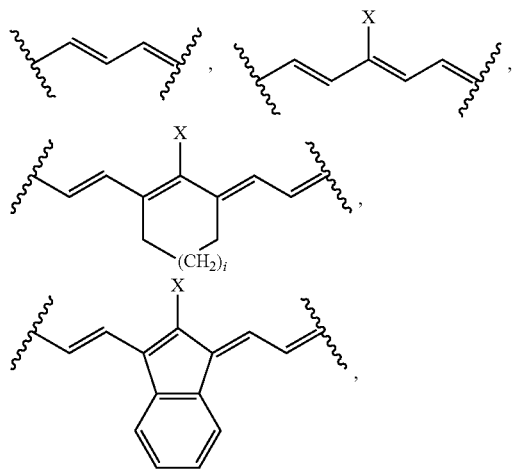

wherein the X group is chosen in the group consisting of: F, Cl, Br, I,

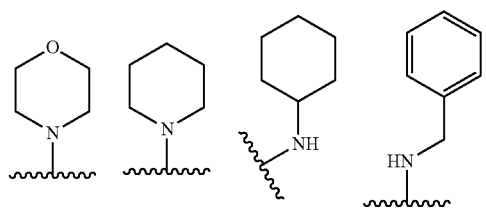

and wherein i is possibly 0 or 1, and wherein the groups $R^{14}$, $R^{15}$ can be advantageously constituted, each one independently from the other, by an alkyl chain $C_1$-$C_{10}$.

An example of cyanine CY7 is the cyanine CY7ClIEt:

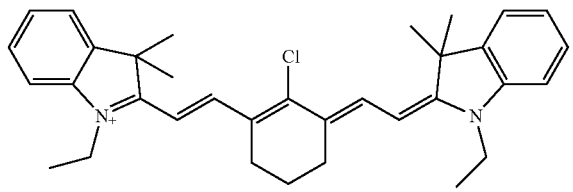 [SMILES: CCN1/C(=C/C=C2\CCCC(/C=C/C3=[N+](CC)c4ccccc4C3(C)C)=C2Cl)C(C)(C)c2ccccc21]

An example of cyanine CY5 is the cyanine Cy5BrNIEt:

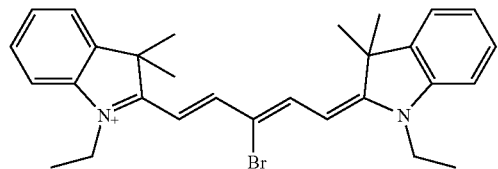 [SMILES: CCN1/C(=C/C=C(Br)/C=C/C2=[N+](CC)c3ccccc3C2(C)C)C(C)(C)c2ccccc21]

Advantageously, E is a ruthenium complex (for example, bis(2,2'-bipyridyl)-[4-(4'-methyl-2,2'-bipyridin-4-yl)butan-1-amine] Ru (II)).

Advantageously, E is chosen among the group consisting of:

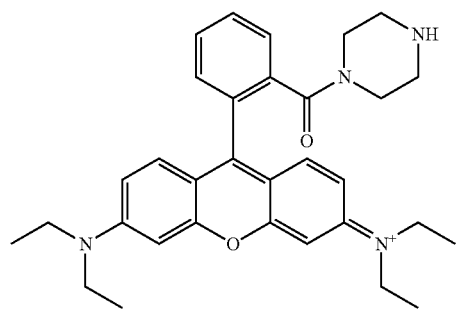

rhodamine B piperizine

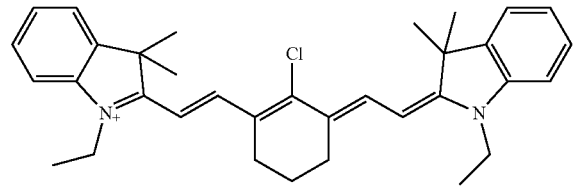

cyanine CY7ClIEt

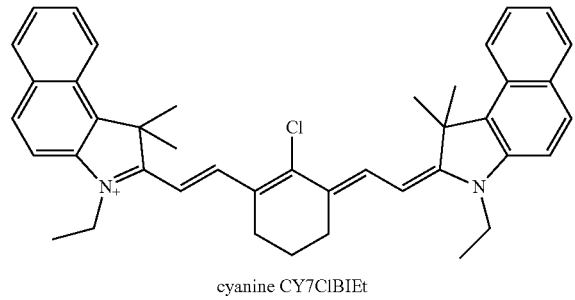

cyanine CY7ClBIEt

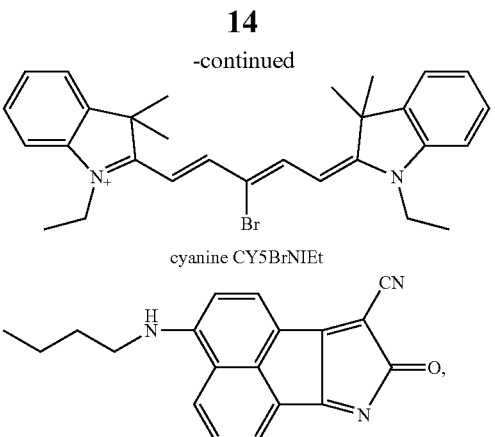

cyanine CY5BrNIEt

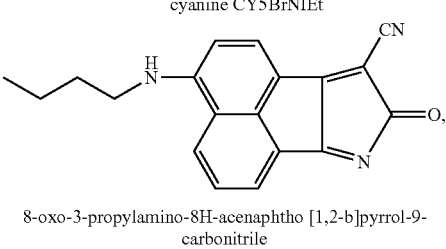

8-oxo-3-propylamino-8H-acenaphtho [1,2-b]pyrrol-9-carbonitrile

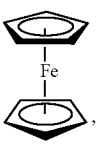

ferrocene

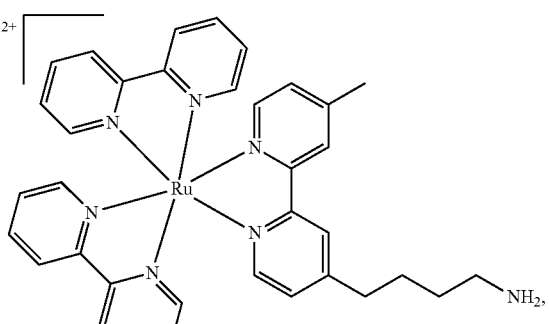

bis (2,2'-bipyridyl)-[4-(4'-methyl-2,2'-bipyridin-4-yl)butan-1-amine] Ru (II)

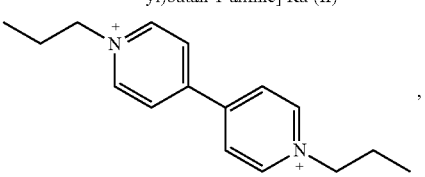

propyl viologen

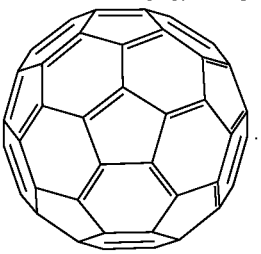

Fullerene $C_{60}$

Advantageously, E is chosen among the group consisting of: dansyl, NBD (7-nitrobenzofurazan), rhodamine B piperazine, rhodamine B isothiocyanate, 8-oxo-3-propylamino-8H-acenaphto[1,2-b]pyrrol-9-carbonitrile, bis(2,2'-bipyridyl)-[4-(4'-methyl-2,2'-bipyridin-4-yl)butan-1-amine] Ru (II), fulleropyrrolidine derivatives, ferrocene derivatives, propyl viologen derivatives. In some embodiments, in addition or as an alternative, E is chosen among the group consisting of:

cyanines CY3 derivatives, cyanines CY5 derivatives, cyanines CY7 derivatives.

Optionally, a linker, which presents an alkylic chain linked to the E portion, is interposed between the E portion as before exemplified and the silicon atom. Optionally, the alkylic chain and the E portion are linked by means of a functional group, for example an aminic or amidic or ureidic or thioureidic.

In some specific embodiments, the active compound is chosen among the group consisting of:

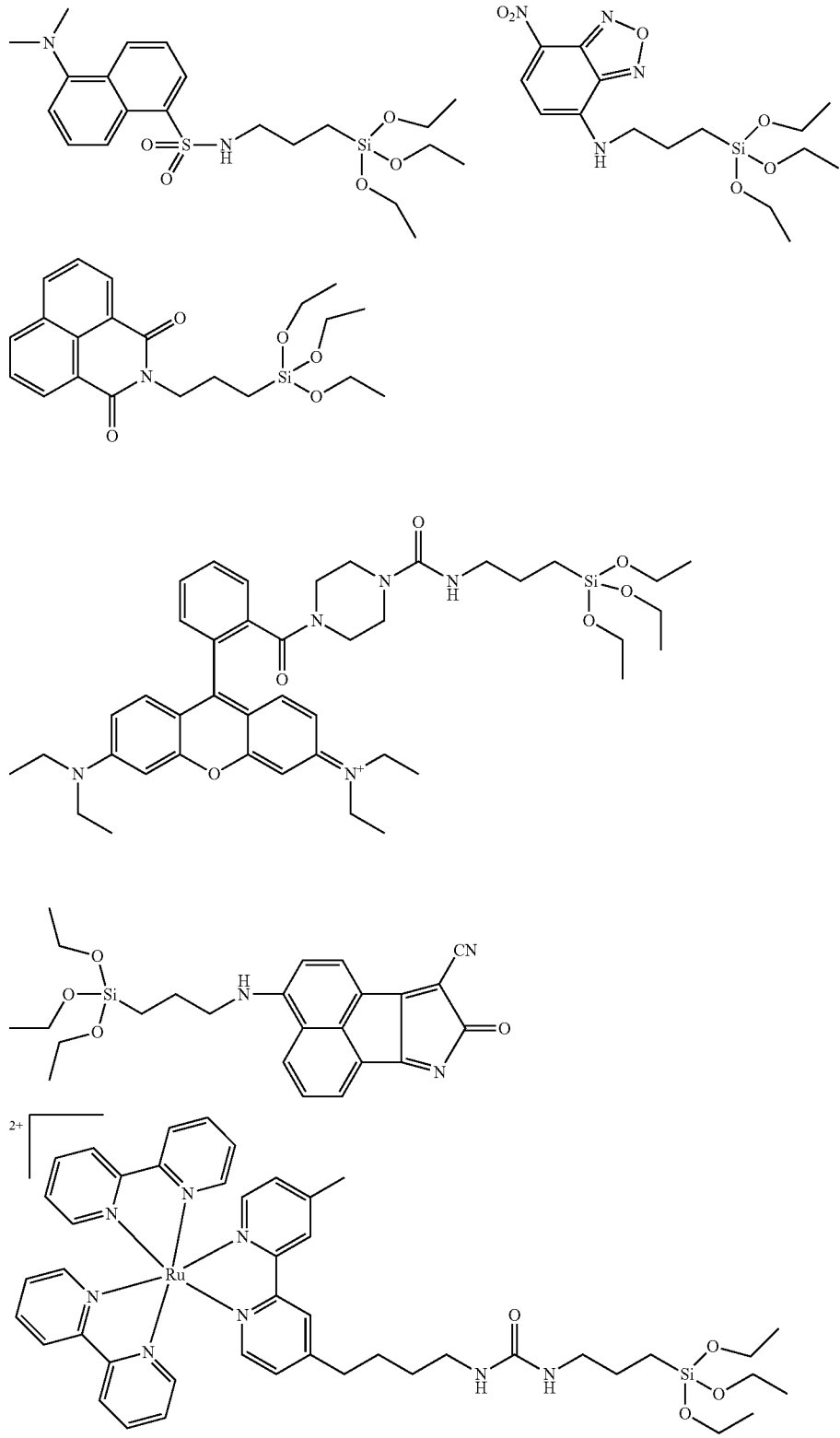

-continued

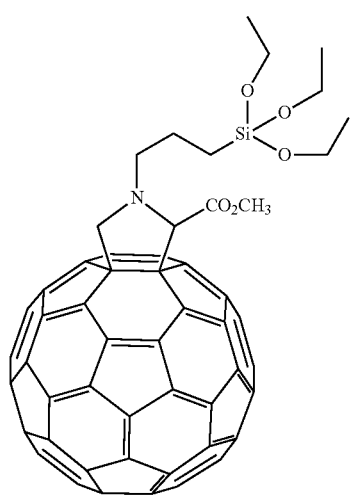
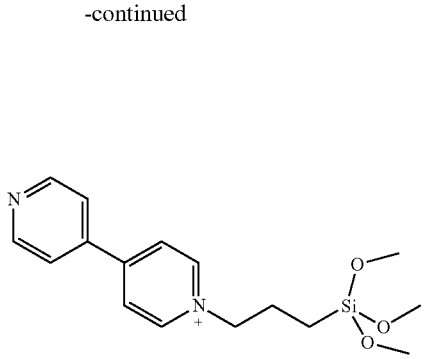
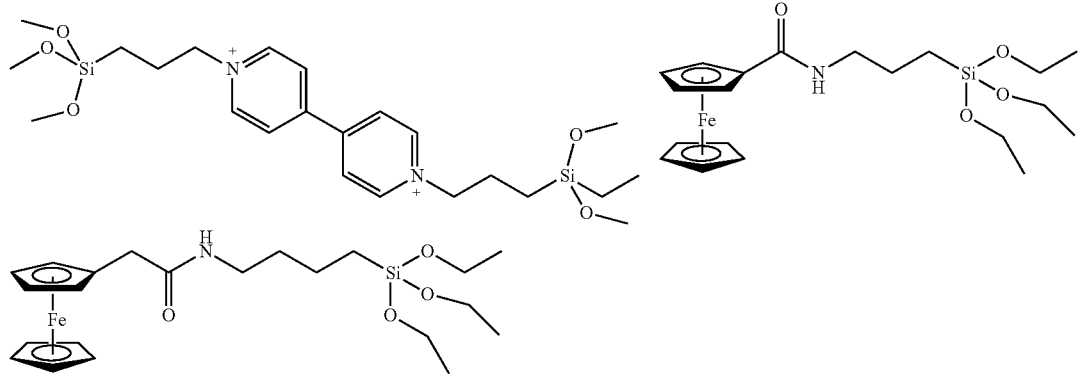
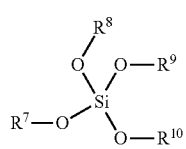

According to some embodiments, the alkoxysilane has a formula chosen in the group consisting of:

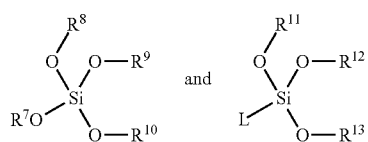

wherein $R^7$, $R^8$, $R^9$, $R^{10}$, $R^{11}$, $R^{12}$ and $R^{13}$ represent, independently of each other, an alkyl $C_1$-$C_4$; L represents a substantially lipophilic molecular portion.

Advantageously, $R^7$, $R^8$, $R^9$, $R^{10}$, $R^{11}$, $R^{12}$ and $R^{13}$ are, independently of each other, an alkyl $C_1$-$C_2$.

According to some embodiments, L represents an alkyl $C_1$-$C_4$. Advantageously, L represents an alkyl $C_1$-$C_2$.

Advantageously, the alkoxysilane has the formula:

According to some embodiments, the alkoxysilane is chosen among the group consisting of:

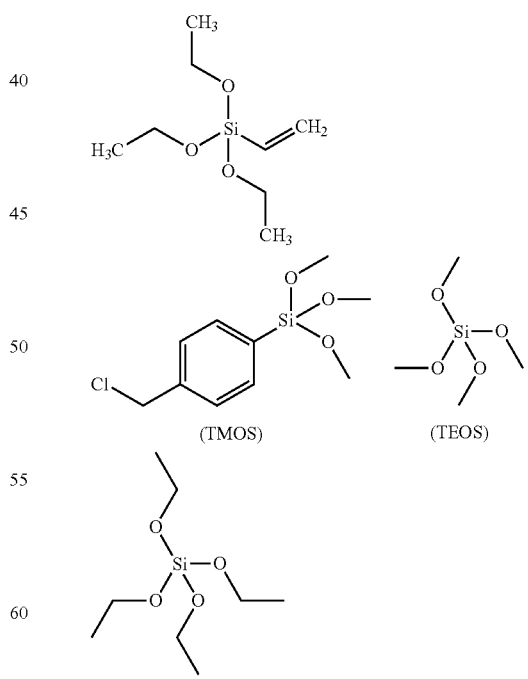

According to some embodiments, the alkoxysilane is chosen among the group consisting of: TMOS e TEOS. Advantageously, the alkoxysilane is TEOS.

According to some embodiments, the reaction step takes place in an aqueous solution. In particular, the aqueous solution has a value of pH lower than about 5 (advantageously higher than about 0), or higher than about 9 (advantageously lower than about 13). In some embodiments, the reaction step takes place in an aqueous solution with a pH lower than about 5, or higher than about 9; the pH is higher than about 0.5 and lower than about 12.

Advantageously, the reaction step takes place in solution; at the beginning of the reaction step, the molar percentage ratio of the active compound to the alkoxysilane is from about 0.002% to about 5%, in particular from about 0.01% to about 0.5% (more precisely, to about 0.2%).

Advantageously, at the beginning of the reaction step, the molar percentage ratio of the alkoxysilane to the surfactant is minor or equal to about 110.

According to some embodiments, where the surfactant has a mean molecular weight higher than circa 10 KDa, the molar ratio of the alkoxysilane to the surfactant is from about 110 to about 90. Where the surfactant has a mean molecular weight from about 8 to about 10 KDa, the molar ratio of the alkoxysilane to the surfactant is from about 90 to about 20. Where the surfactant has a mean molecular weight from about 6 to about 8 KDa, the molar ratio of the alkoxysilane to the surfactant is from about 20 to about 9. Where the surfactant has a mean molecular weight from about 3 to about 6 KDa, the molar ratio of the alkoxysilane to the surfactant is from about 9 to about 4.

In the majority of the embodiments, the reaction step lasts less than about 6 hours. Advantageously, the reaction step lasts more than about 1 hour, specifically it lasts about 1 hour and 45 minutes.

Experimentally, it has been observed that it is possible to improve the monodispersity (i.e. to reduce the amplitude of the distribution of the particle diameters) performing the reaction step in presence of a strong electrolyte. This is particularly useful when trialkoxysilanes instead of tetraalkoxysilanes are used and/or when the aqueous solution contains a weak acid (for example acetic acid) or a weak base (for example ammonia).

Therefore, advantageously, the aqueous solution in the reaction step comprises a strong electrolyte (for example NaCl or KCl) with a concentration from about 0.1 M to about 3.0 M.

According to some embodiments, the above disclosed method above comprises a termination step, during which the reaction is stopped through the addition of a termination compound chosen among the group consisting of: monoalkoxysilane, dialkoxysilane, monohalosilane, dihalosilane; in particular the termination step follows the reaction step.

Advantageously, the termination compound is chosen among: dialkoxysilane, in particular diethoxydimethylsilane, and monohalosilane, in particular chlorotrimethylsilane.

By dihalosilane it is meant a molecule having a silicon bound to only two halogens, advantageously Cl, Br, I, advantageously Cl. Advantageously, the dihalosilane is chosen in the group consisting of:

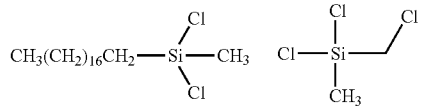

-continued

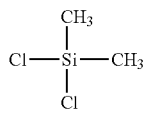

By monohalosilane it is meant a molecule that has a silicon bound to only one halogen, advantageously Cl, Br, I, advantageously Cl. Advantageously, the monohalosilane is chosen among the group consisting of:

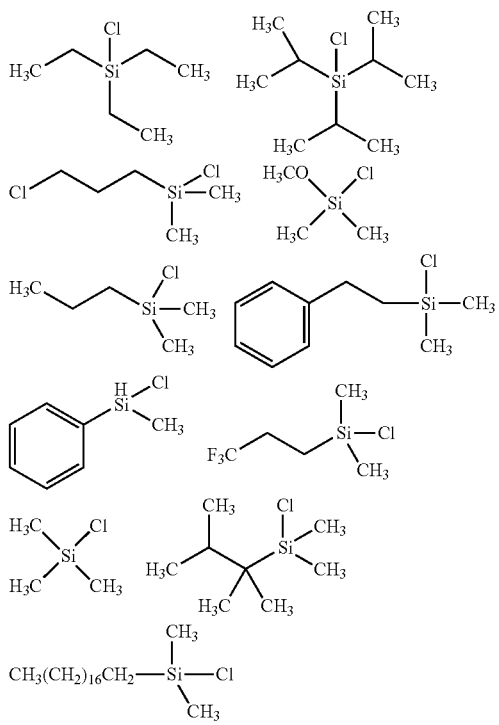

By dialkoxysilane it meant a molecule having only two alkoxysilane moieties, in which the two alkoxy groups of the alkoxysilane moieties are bound to the same silicon atom. Advantageously, the dialkoxysilane is chosen in the group consisting of:

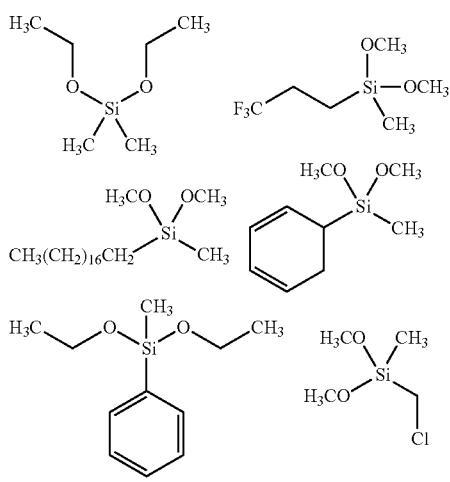

-continued

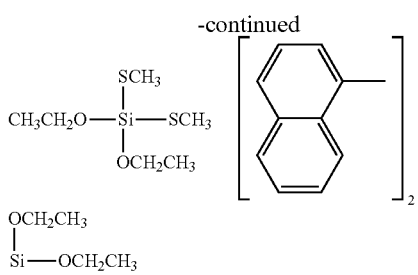

By monoalkoxysilane it is meant a molecule having only one alkoxysilane moiety. Advantageously, the monoalkoxysilane is chosen among the group consisting of:

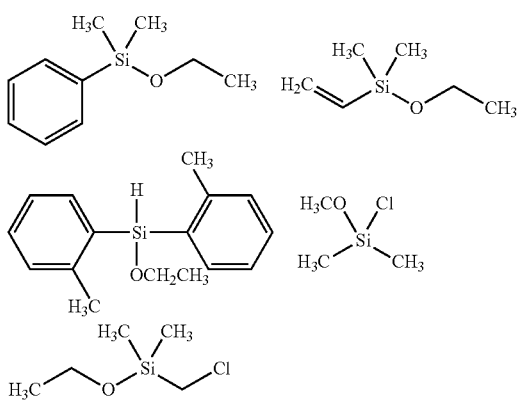

Advantageously, a separation step is performed after the reaction step. Possibly, the separation step is carried out after the termination step. According to some embodiments, the separation step is performed via dialysis and/or ultrafiltration and/or dia-ultrafiltration.

In relation to the afore provided description, it must be noted that the formation of the core, which can be formed from the hydrolysis and condensation processes of organosilicates, leads to the substantially irreversible immobilization of the surfactant molecules in the particle.

In accordance with a second group of embodiments, the method comprises a mixing step, during which the active compound, which is essentially lipophilic, is mixed with molecules of functionalized surfactant in an organic solvent; and an evaporation step, that is subsequent to the mixing step and previous to the reaction step, and during which the organic solvent is evaporated in order to obtain a residue.

It emphasised that in some embodiments, features described in relation to the first group of embodiments are present also in the second group of embodiments.

The organic solvents that can be used during the mixing step are several. According to some embodiments, the organic solvent is chosen among this group: methanol, chloroform, dichloromethane, tetrahydrofuran, acetonitrile, toluene, ethanol.

Advantageously, the alkoxysilane and the surfactant are defined in accordance with the afore presented description.

According to some embodiments, the active compound is chosen in the group consisting of: 4-(Dicyanomethylene)-2-methyl-6-(4-dimethylaminostyryl)-4H-pyran, phthalocyanines, naphthalocyanines, carboxyimidic derivatives of perylene (for example, N,N□-Bis(2,5-di-tert-butylphenyl)-3,4,9,10-perylenedicarboximide), cyanines (CY7; CY5; CY3), Ir (III) complexes, triethoxysilane derivatives of rhodamine B, fullerene $C_{60}$ and its derivatives, organic lipophilic ECL active compounds (for example: rubrene, 9,10-diphenylanthracene, 9,10-dichloroanthracene, acridine, decacyclene, fluoranthene, etc.).

Advantageously, the active compound is chosen in the group consisting of: cyanines (CY7; CY5; CY3), Ir (III) and Ru (II) complexes. In particular, the active compound is chosen among cyanines CY7 and cyanines CY5.

According to some specific embodiments, the active compound is chosen among the group consisting of:

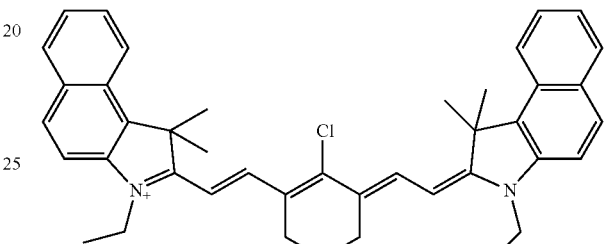

cyanine CY7ClBIEt

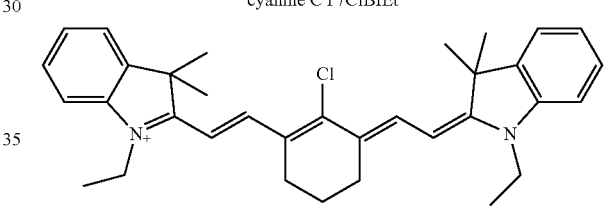

cyanine CY7ClIEt

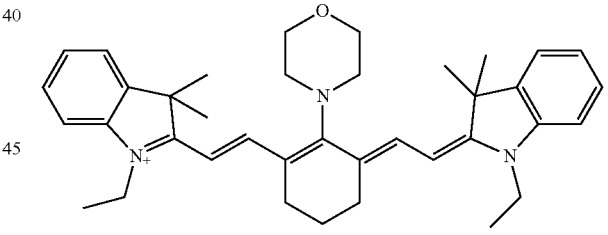

cyanine CY7MorfBrEt

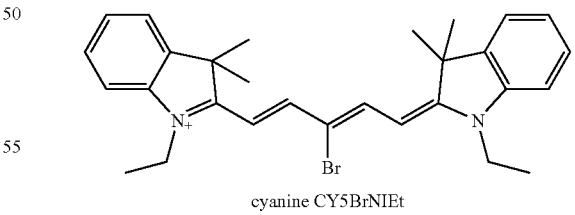

cyanine CY5BrNIEt

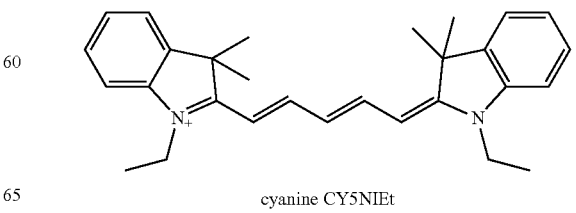

cyanine CY5NIEt

-continued

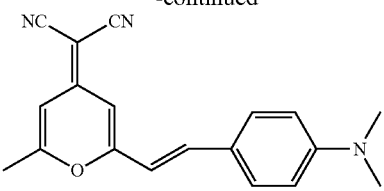

4-(Dicyanomethylene)-2-methyl-6-(4-dimethylaminostyryl)-
4H-pyran

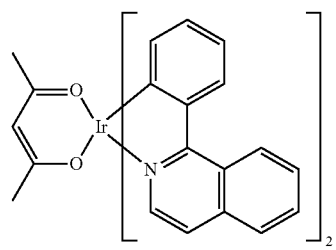

Bis-(1-phenylisoquinoline) (acetylacetonate) iridium (III),
Ir (III) (pq)$_2$acac

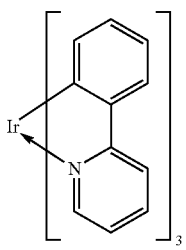

Tris (2-phenylpyridine) iridium (III), Ir (ppy)$_3$

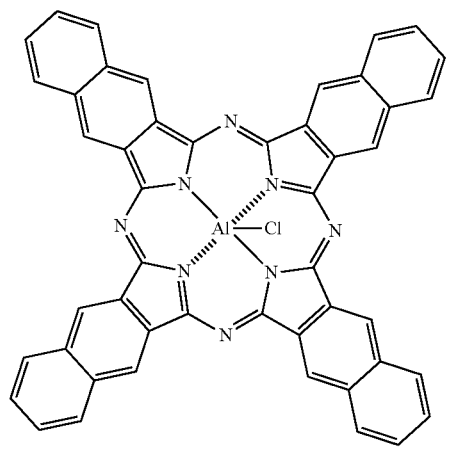

Aluminum 2,3-naphthalocyanine chloride

-continued

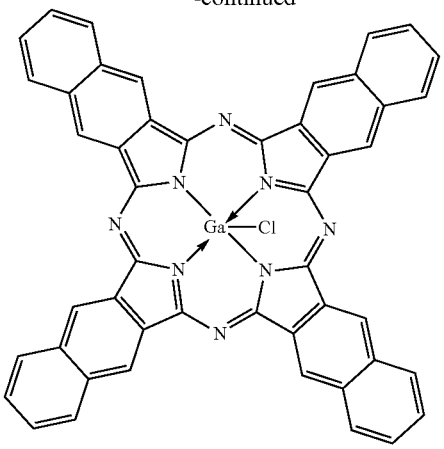

Gallium (III) 2,3-naphthalocyanine chloride

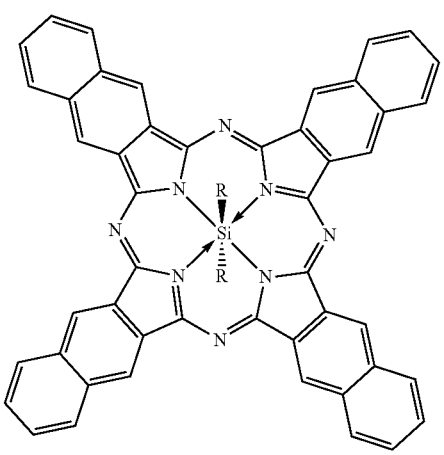

Silicon 2,3-naphthalocyanine dioctyloxide
R = OCH(CH$_2$)$_6$CH$_3$

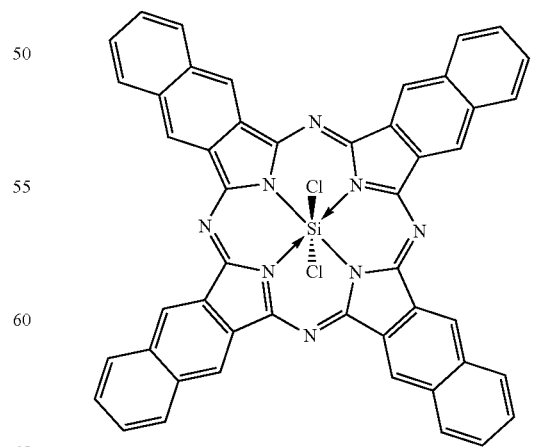

Tin (IV) 2,3-naphthalocyanine dichloride

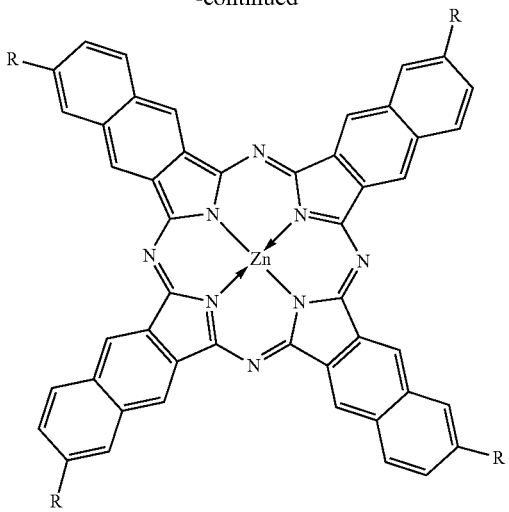

Zinc 2,11,20,29-tetra-tert-butyl-2,3-naphthalocyanine

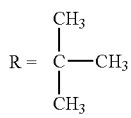

Method for the Preparation of a Particle with a Active Compound Covalently Linked In accordance with a third aspect of the present invention, it is provided a method for the preparation of an active particle comprising a reaction step, during which molecules of at least one alkoxysilane are silanized together with at least one active compound in presence of water and of molecules of at least one surfactant; the alkoxysilane is chosen among a tetraalkoxysilane and a trialkoxysilane; the active compound contains at least one alkoxysilane moiety; the surfactant contains the following structure:

Hydro$^1$-Lipo-Hydro$^2$ wherein Lipo indicates a substantially hydrophobic chain, Hydro$^1$ and Hydro$^2$ indicate each a respective substantially hydrophilic chain.

Figure 45:
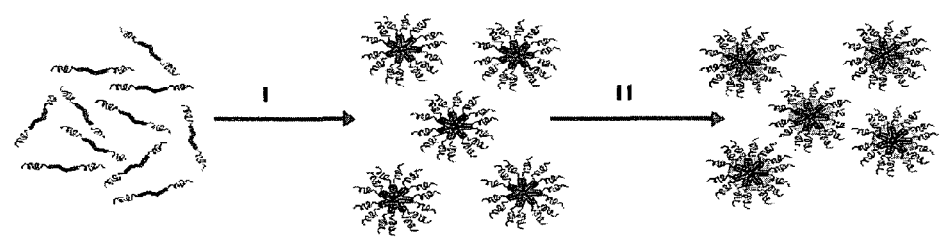
FIG. 45 shows schematically for merely exemplificative purposes a method in accordance with the present invention.

FIG. 45 shows schematically, for merely exemplificative and non limiting purposes, the formation of particles (shown on the right): the surfactant molecules (or the surfactants molecules, shown on the left) in presence of water form micelles (shown in the middle); the alkoxysilane and the active compound silanize forming a core (shown on the right in correspondence of a central portion of the particles).

According to some embodiments, the micelles are micellar aggregates.

According to some embodiments, the reaction step occurs in the conditions described in accordance with the second aspect of the present invention.

Advantageously, the active compound is defined in accordance with the second aspect of the present invention. In particular, the active compound is defined in accordance with the first group of embodiments of the second aspect of the present invention.

According to some embodiments, Lipo is substantially lipophilic. Advantageously, Hydro$^1$ and Hydro$^2$ are more soluble in water than in ethanol.

In some embodiments, Hydro$^1$ represents a chain

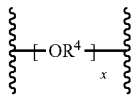

wherein R$^4$ is a linear alkyl C$_1$-C$_3$ (advantageously C$_2$-C$_3$); Hydro$^2$ represents a chain

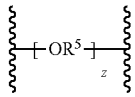

where R$^5$ is a linear alkyl C$_1$-C$_3$ (advantageously C$_2$-C$_3$); Lipo represents a chain

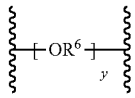

where R$^6$ is a branched alkyl C$_3$-C$_4$.

Advantageously, R$^4$ and R$^5$ are defined, independently of each other, in accordance with the first (and/or the second) aspect of the present invention.

Advantageously the surfactant is a block co-polymer ethylene oxide/propylene oxide.

According to some embodiments, x, y and z are defined, each one independently from the other, in accordance with the first (and/or the second) aspect of the present invention.

Advantageously, Hydro$^1$ represents a chain

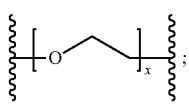

Hydro$^2$ represents a chain

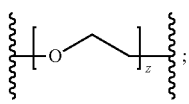

Lipo represents a chain

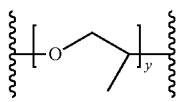

Usually the structure Hydro$^1$-Lipo-Hydro$^2$ presents at the left end one terminal hydrogen atom bound to oxygen, and at the right end one hydroxyl moiety. This is exemplified by Pluronic® F127:

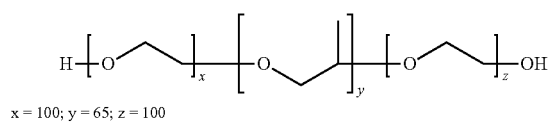

x = 100; y = 65; z = 100

Alternatively, the extremities of the structure Hydro¹-Lipo-Hydro² can be functionalized in different ways. This is for example described in the first and/or second aspect of the present invention.

According to some embodiments, the particle has a hydrodynamic diameter defined in accordance with the first (and/or second) aspect of the present invention.

According to some embodiments, the surfactant has an average molecular weight defined in accordance with the first (and/or second) aspect of the present invention.

In particular, the ratios of the average molecular weight of Lipo to the average molecular weight of Hydro¹ and of the average molecular weight of Lipo to the average molecular weight of Hydro² are, independently of each other, defined in accordance with the first (and/or second) aspect of the present invention.

According to some embodiments, the surfactant is chosen among the group consisting of: Pluronic® F127, F98, P105, F68, F108, F88, F87.

According to some embodiments, the alkoxysilane is defined in accordance with the second (and/or the first) aspect of the present invention.

According to some embodiments, the reaction step is performed in the conditions defined in accordance with the second aspect of the present invention.

For merely exemplificative and non limiting purposes, FIG. 20 shows a specific example of a reaction step.

According to some embodiments, the aforementioned method comprises a termination step, during which the reaction step is stopped through the addition of a termination compound. In particular, the termination step is subsequent to the reaction step.

Advantageously, the termination compound is defined in accordance with the second aspect of the present invention. In some embodiments, the termination step is performed in accordance with what described in relation to the second aspect of the present invention.

Advantageously, a separation step is performed after the reaction step, and potentially after the termination step. In some embodiments, the separation step is performed through dialysis and/or ultrafiltration and/or dia-ultrafiltration.

According to some embodiments, the method in accordance with the third aspect of the present invention presents one or more of the single features indicated above with reference to the first aspect of the present invention.

According to some embodiments, the method in accordance with the third aspect of the present invention has one or more of the single features indicated above with reference to the second aspect of the present invention.

Particle with a Active Compound Covalently Linked

In accordance with a fourth aspect of the present invention, it is provided a particle comprising a micelle, which in turn has a shell (i.e. a part oriented towards the exterior) substantially hydrophilic and an inner portion substantially hydrophobic; and a core, which is located in the area of the inner portion of the micelle and comprises a silicate network bound covalently to at least one active compound. The micelle comprises a plurality of molecules of at least one surfactant, which has the following structure:

Hydro¹-Lipo-Hydro² wherein Lipo indicates a substantially hydrophobic chain, Hydro¹ and Hydro² indicate each a respective substantially hydrophilic chain.

Advantageously, the particle is obtained in accordance with the third aspect of the present invention.

Advantageously, the particle is obtainable in accordance with the third aspect of the present invention.

Advantageously, the surfactant is defined in accordance with the third aspect of the present invention.

Advantageously, the active compound is defined in accordance with the third aspect of the present invention.

Advantageously, the active compound is defined in accordance with the second aspect of the present invention.

According to some embodiments, the particle has an average hydrodynamic diameter in water lower than circa 100 nm, advantageously, from about 40 to about 10 nm.

According to some embodiments some embodiments, the core has a diameter lower than about 30 nm, in particular from about 5 to about 15 nm.

Advantageously, the particle is obtainable in accordance with the method of the third aspect of the present invention.

Advantageously, the particle is obtained in accordance with the method of the third aspect of the present invention.

The formation of the core, which can be formed from the hydrolysis and condensation processes of organosilicates, leads to the substantially irreversible immobilization of the surfactant molecules in the particle.

According to some embodiments, where the surfactant has a mean molecular weight higher of circa 10 KDa, the molar ratio of the alkoxysilane to the surfactant is from about 110 to about 90. Where the surfactant has a mean molecular weight from about 8 to about 10 KDa, the molar ratio of the alkoxysilane to the surfactant is from about 90 to about 20. Where the surfactant has a mean molecular weight from about 6 to about 8 KDa, the molar ratio of the alkoxysilane to the surfactant is from about 20 to about 9. Where the surfactant has a mean molecular weight from about 3 to about 6 KDa, the molar ratio of the alkoxysilane to the surfactant is from about 9 to about 4.

According to some embodiments some embodiments, the particle in accordance with the fourth aspect of the present invention has one or more of the single features indicated above with reference to the first aspect of the present invention.

According to some embodiments some embodiments, the particle in accordance with the fourth aspect of the present invention has one or more of the single features indicated above with reference to the second aspect of the present invention.

With reference to the first and/or second and/or third and/or fourth aspect of the present invention, in some advantageous embodiments, the active compound is different form the surfactant. With reference to the first and/or second and/or third and/or fourth aspect of the present invention, in some advantageous embodiments, the active compound is different form the alkoxysilane. With reference to the first and/or second and/or third and/or fourth aspect of the present invention, in some advantageous embodiments, the alkoxysilane is different from the surfactant.

By different it is meant substances that do not have the same chemical formula (specifically, the same chemical structure).

In accordance with a further aspect of the present invention, the following luminescent, elettrochemiluminescent and electroactive compounds are provided:

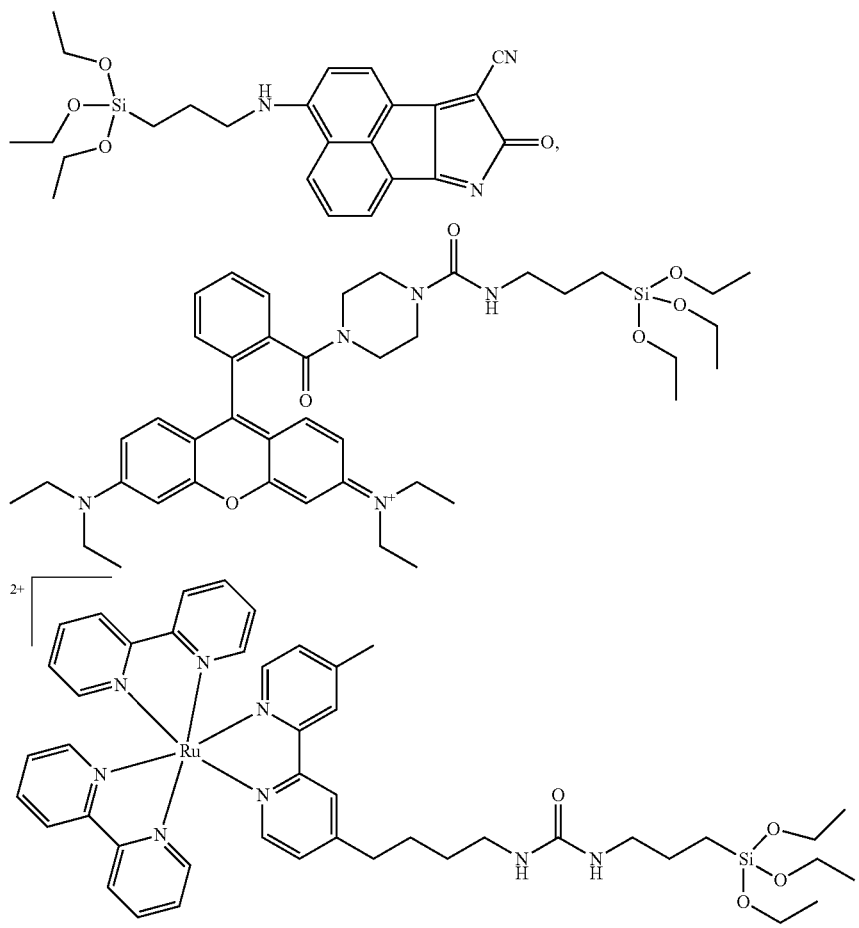

These active compounds are useful in the synthesis of the particles described in the second aspect of the present invention.

The particles in accordance with the present invention can have the following applications:

as luminescent labels (Zhao, X. Et al. *J. Am. Chem. Soc.* 2003, 125, 11474-11475) of systems based on microarrays for diagnostic purposes (Wang, L. et al. *Bioconjugate Chem.* 2007, 18, 610-613) and for in vivo imaging (Kobayashi, H. et al. *Nano Lett.* 2007, 7, 1711-1716) and in vitro imaging (Wang, L. et al. *Bioconjugate Chem.* 2007, 18, 297-301);

for the development of magnetic particles with luminescent properties (Lu, C.-W. et al. *Nano Lett.* 2007, 7, 149-154; Lu, Y. et al. *Nano Lett.* 2002, 2, 183-186; Lattuada, M. et al. *Langmuir* 2007, 23, 2158-2168; Hu, F. et al. *Biomacromolecules* 2006, 7, 809-816; Yang, H.-H. et al. *Anal. Chem.* 2004, 76, 1316-1321; US 20070059705; US006545143B1);

for the photothermal therapy (PTT) (Everts, M.; Saini, V.; Leddon, J. L.; Kok, R. J.; Stoff-Khalili, M.; Preuss, M. A.; Millican, C. L.; Perkins, G.; Brown, J. M.; Bagaria, H.; Nikles, D. E.; Johnson, D. T.; Zharov, V. P.; Curiel, D. T. *Nano Lett.* 2006, 6, 587-591; Zharov, V. P.; Kim, J.-W.; Curiel, D. T.; Everts, M. *Nanomedicine* 2005, 1, 326-345);

for the photodynamic therapy (PDT) (McCaughan, J. S. Jr. *Drugs and Aging* 1999, 15, 46-68; Prasad, P. N. et al. *Nano Lett.* 2007, 7, 2835-2842; Prasad, P. N. et al. *Proc. Natl. Acad. Sci. USA* 2005, 102, 279-284; Prasad, P. N. et al. *J. Am. Chem. Soc.* 2003, 125, 7860-7865; US 20040180096; US 20060088599; US 20070217996);

for PET (positron emission tomography) applications (Pressly, E. D.; Rossin, R.; Hagooly, A.; Fukukawa, K.-i.; Messmore, B. W.; Welch, M. J.; Wooley, K. L.; Lamm, M. S.; Hule, R. A.; Pochan, D. J.; Hawker, C. J. *Biomacromolecules* 2007, 8, 3126-3134; R Cartier et al. *Nanotechnology* 2007, 18, 195102-195120);

for MRI (magnetic resonance imaging) imaging and of the contrast agents;

in ophthalmology as material used in the tissue welding obtained with the use of a laser (Chetoni, P. et al. *J. Drug. Del. Sci. Tech.* 2007, 17, 25-31).

In accordance with further aspects of the present invention it is hereby, therefore, provided what follows.

A particle in accordance with the first aspect of the present invention (or obtained in accordance with the second aspect of the present invention), wherein at least one among $M^1$ and $M^2$ is a recognition functionality, for diagnostic use.

A use of a particle as defined in accordance with the first aspect of the present invention (or obtained in accordance with the second aspect of the present invention), wherein at least one among $M^1$ and $M^2$ is a recognition functionality, for the production of a product for diagnostic use.

A use of a particle as defined in accordance with the first aspect of the present invention (or obtained in accordance with the second aspect of the present invention), wherein at least one among $M^1$ and $M^2$ is a recognition functionality, for diagnostic purposes.

A diagnostic method that makes use of a particle as defined in accordance with the first aspect of the present invention (or obtained in accordance with the second aspect of the present invention), in which at least one among $M^1$ and $M^2$ is a recognition functionality.

A particle as defined in accordance with the first aspect of the present invention (or obtained in accordance with the second aspect of the present invention), wherein at least one among $M^1$ and $M^2$ is a recognition functionality, for a therapeutic treatment, in particular for phototherapy.

A use of a particle as defined in accordance with the first aspect of the present invention (or obtained in accordance with the second aspect of the present invention), wherein at least one among $M^1$ and $M^2$ is a recognition functionality, for the preparation of a product for therapeutic use, in particular for phototherapic use.

A use of a particle as defined in accordance with the first aspect of the present invention (or obtained in accordance with the second aspect of the present invention), wherein at least one among $M^1$ and $M^2$ is a recognition functionality, for a therapeutic treatment, in particular for phototherapy.

A therapeutic method, in particular a phototherapic one, that makes use of a particle as defined in accordance with the first aspect of the present invention (or obtained in accordance with the second aspect of the present invention), wherein at least one among $M^1$ and $M^2$ is a recognition functionality.

A diagnostic preparation containing at least one particle as defined in accordance with the first aspect of the present invention (or obtained in accordance with the second aspect of the present invention), wherein at least one among $M^1$ and $M^2$ is a recognition functionality, and, advantageously, at least one pharmaceutically acceptable excipient.

A pharmaceutical preparation containing at least one particle as defined in accordance with the first aspect of the present invention (or obtained in accordance with the second aspect of the present invention), wherein at least one among $M^1$ and $M^2$ is a recognition functionality, and, advantageously, at least one pharmaceutically acceptable excipient.

A use as a probe (or label) of a particle as defined in accordance with the first aspect of the present invention (or obtained in accordance with the second aspect of the present invention), wherein at least one among $M^1$ and $M^2$ is a recognition functionality.

A use as in vivo probe (or label) of a particle as defined in accordance with the first aspect of the present invention (or obtained in accordance with the second aspect of the present invention), wherein at least one among $M^1$ and $M^2$ is a recognition functionality.

In accordance with further aspects of the present invention, it is, therefore, provided what follows.

A particle in accordance with the fourth aspect of the present invention for diagnostic use.

A use of a particle in accordance with the fourth aspect of the present invention for the preparatione of a product for diagnostic use.

A use of a particle in accordance with the fourth aspect of the present invention for diagnostic purposes.

A diagnostic method that makes use of a particle in accordance with the fourth aspect of the present invention.

A particle in accordance with the fourth aspect of the present invention for a therapeutic treatment, in particular for phototherapy.

An use of a particle in accordance with the fourth aspect of the present invention for the production of a product for therapeutic use, in particular for phototherapic use.

An use of a particle in accordance with the fourth aspect of the present invention for use in a therapeutic treatment, in particular for phototherapy.

A therapeutic method, in particular a phototherapic one, that makes use of a particle in accordance with the fourth aspect of the present invention.

A diagnostic preparation containing at least one particle as defined in accordance with the fourth aspect of the present invention and, advantageously, at least one pharmaceutically acceptable excipient.

A pharmaceutical preparation containing at least one particle as defined in accordance with the fourth aspect of the present invention and, advantageously, at least one pharmaceutically acceptable excipient.

With phototherapy it is meant photothermal therapy and/or photodynamic one; advantageously photothermal.

A use as probe (or label) of a particle as defined in accordance with the fourth aspect of the present invention.

A use as in vivo probe (or label) of a particle as defined in accordance with the fourth aspect of the present invention.

The particles, depending on preparation, are compatible for all kinds of formulation and consequently of administration: in particular, for oral, parenteral or rectal administrations or for inhalations or insufflations (both through the mouth or through the nose). Formulations in view of parenteral administrations are favoured.

For oral administrations, the pharmaceutical preparations can be in form of, for example, pills or capsules prepared by means of known methodologies with acceptable excipients from a pharmaceutical point of view, like binders (for example pregelatinized maize starch, polyvinylpyrrolidone or methylcellulose), fillers (for example lactose, microcrystalline cellulose, or calcium hydrogen phosphate), additives (for example magnesium stearate, talc, silica), disintegrants (for example potato starch), and/or lubricating agents (for example sodium lauryl sulfate). Pills can be covered by means of known methods. Liquid preparations for oral administrations can be in the form of, for example, syrups or suspensions, or they can be in the form of a dried product that can be dissolved in water or in another liquid before usage. These preparations can be prepared in many ways with acceptable excipient from a pharmaceutical point of view, like suspending agents (for example sorbitol, cellulose derivatives, edible hydrogenated fats), emulsifying agents (for example lecithin or acacia), non aqueous liquids (for example almond oil, oily esters, ethyl alcohol or fractionated vegetable oils), and/or preservatives (for example methyl or propyl p-hydroxybenzoates, sorbic acid or ascorbic acid). Preparations can also contain, in appropriate cases, buffered salts, coloring agents, flavor enhancers and/or sweeteners.

Preparations for oral administration can be formulated in a known way, in order to obtain a controlled release of the active compound.

Particles can be formulated, in a known way, for parenteral administration via injection or for a continuous administration. Formulations for injections can be in the form of unit-dose, for example in vials or in multidose containers including preservatives. The dosage form can be a suspension, in aqueous or oily liquids, and can contain elements of the formulation such as dispersing and stabilizing agents.

Particles can be formulated for rectal administration as suppositories or enemas, for example including known excipients for suppositories like, for example, cocoa butter or other glycerides.

Particles can also be formulated, in a known way, for prolonged release dosage forms. These compositions for prolonged release can be administered through an implant (for example subcutaneous or intramuscular) or through an intramuscular injection. Therefore, for example, one can use dosage forms with the appropriate polymeric or hydrophobic (for example an emulsion or an oil) materials or ion-exchange resins, or relatively poorly soluble derivatives, like relatively poorly soluble salts.

For intranasal administrations, particles can be formulated for administrations through a (known) device, for example as a powder with an appropriate carrier.

The dosages of particles will depend on the age and conditions of the patient, therefore the exact dosage will have to be decided each time. The dosage will also depend on the administration method and from the particular kind of particles used.

The subject to be treated can be any mammal, for example a human being. Examples of mammals that can be treated are: farm animals like cows, pigs, sheep, goats and horses; pets like cats and dogs, laboratory animals like guinea-pigs, rabbits, mice and rats.

By phototherapy it is meant photothermal therapy and/or photodynamic one; advantageously photothermal.

The subject matter of the present invention has the following advantages with respect to the state of the art:

Technical Advantages:
ease of the synthetic procedures;
the obtained particles are sterically stabilized, monodispersed, and extremely stable, especially in aqueous solution and in physiological conditions of temperature, ionic strength and pH;
the particles are very soluble in aqueous environment;
one can obtain luminescent systems that emit in a wide range of wavelengths (UV-VIS-IR);
in the majority of the cases, the efficiency (luminescent quantum yield) of the active compounds (in particular, emissive ones) that are trapped or condensed inside the particles, increases;
there is an increase of the resistance to photodegradation of the active compounds that are inside the particles in comparison with the isolated active compound;
the particles can be functionalized with a great variety of functional groups on their surface, that, in particular, allow the same particles to bind with a substrate and/or an analyte so that can be efficiently used for diagnostic and/or therapeutic purposes.

In relation to this last point, it must be noted that, for example, the particles, functionalized in accordance with some aspects of the present invention, bind, when in use, to a specific substrate so that, during a phototherapic treatment, the effects of the emission of the emitting compound take place exactly in the nearness of the aforementioned specific substrate; analogously, it is possible to detect the presence, the position and the amount of an analyte to which particles containing active compounds are bound in accordance with some aspect of the present invention.

The object of the present invention presents has following further advantages:

Economical Advantages:
the initial components and reagents necessary for the synthesis of the particles are extremely cheap;
in order to realize this kind of luminescent particles it is often possible to use commercial and cheap luminophores;
there is no need of special or expensive equipments in order to realize the invention;
the luminophore of election is introduced in the synthetic step, it is quantitatively segregated in the core of the particle without wastes.

Production Advantages:
the initial components and reagents necessary for the synthesis of the particles are easily available;
ease and fastness of the synthetic procedure for the preparation of the particles;
possible synthetic procedures for the modification of the surfactant Pluronic® F127 (or similar) are not laborious;
the possibility of using commercially available luminophores avoids the step of their synthesis or modification that are usually demanding, laborious and long procedures;
normal laboratory equipments are needed to realize the invention, the particle synthesis requires mild conditions of pressure and temperature;
Pluronic® F127 (or similar) is a non toxic surfactant;
water is advantageously used as the reaction solvent.

The present patent application claims the priority of two Italian patent application (specifically, BO2008A000485 and BO2008A000486), the content of which is here entirely reported. In particular, the Italian patent applications are incorporated here as a reference.

Further characteristics of the present invention will arise from the hereinafter description of some examples that are merely illustrative and not limiting.

EXAMPLES

The UV-VIS absorption measurements have been performed using Perkin Elmer Lambda 650 and Lambda 45 spectrophotometers. The luminescence emission measurements have been performed using a Perkin Elmer LS50 spectrofluorimeter and a modular Edinburgh fluorimeter equipped with Picoquant lasers with different wavelengths and with polarizers and with a module for emission lifetime measurements.

The determinations of the hydrodynamic radius of the particles through DLS (dynamic light scattering) technique have been obtained with a NANO ZS by Malvern Instruments.

Example 1

Preparation of the dimesylate Derivative of the Surfactant Pluronic® F127 (BASF)

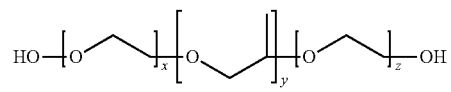

$x = 100; y = 65; z = 100$

Pluronic® F127

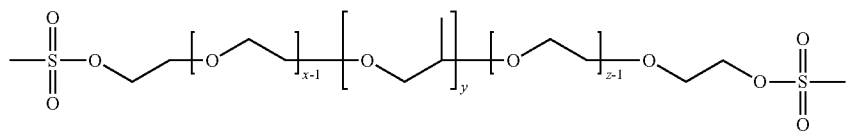

Dimesylate Derivative of the Surfactant Pluronic® F127

12.6 g of Pluronic® F127 surfactant (1.0 mol) dried by means of azeotropic distillation at low pressure in toluene were solubilized in 50 mL of anhydrous $CH_2Cl_2$. This solution was cooled to 0° C. and kept under an inert atmosphere ($N_2$); then, 280 μL of triethylamine (2.0 mmol) and 155 μL of methanesulfonyl chloride (2.0 mmol) were added. The reaction mixture was kept under stirring at 0° C. for three hours and then at room temperature overnight. The suspended solid was filtered away and the collected solution was distilled under reduced pressure and dried under vacuum (almost quantitative yield).

$^1$H NMR (300 MHz, $CDCl_3$, 25° C., δ ppm): 4.38-4.35 (m, 4H, —$OCH2CH_2OSO_2CH_3$), 3.87-3.84 (m, 4H, —$OCH2CH_2OSO_2CH_3$), 3.62 (s, —$OCH_2CH_2O$—), 3.57-3.46 (m, —$OCH_2CHCH_3O$—), 3.41-3.35 (m, —$OCH_2CHCH_3O$—) 1000H, 3.07 (s, 6H, —$OSO_2CH_3$), 1.13-1.10 (m, —$OCH_2CHCH_3O$—) 196H.

$^{13}$C NMR (75.7 MHz, $CDCl_3$, 25° C., δ ppm): 75.0, 74.9, 74.8, 72.9, 72.6, 72.5, 72.3, 70.1, 69.0, 68.6, 17.1, 16.9.

Example 2

Preparation of the diazide Derivative of the Surfactant Pluronic® F127 (BASF)

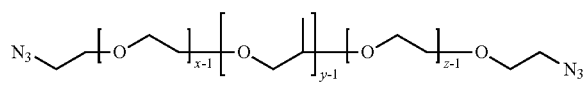

Pluronic® F127 diazide

A solution composed of 10.2 g of the dimesylate derivative of Pluronic® F127 (0.8 mmol) and 156 mg of sodium azide (2.4 mmol) in 50 mL of $CH_3CN$ was heated at reflux for 48 hours. The solvent was then removed from the reaction mixture by means of distillation under reduced pressure. The obtained solid was redispersed in a 5% $NaHCO_3$ aqueous solution and the solution was then saturated with solid NaCl. This mixture was extracted several times with $CH_2Cl_2$ (6-8 times). The reunited organic phases were dried over $Na_2SO_4$, filtered and evaporated at low pressure, affording a white solid (almost quantitative yield).

$^1$H NMR (300 MHz, $CDCl_3$, 25° C., δ ppm): 3.86-3.82 (m, 4H, —$OCH_2CH_2O$—$CH_2CH_2N_3$); 3.60 (s, —$OCH_2CH_2O$—), 3.53-3.45 (m, —$OCH_2CHCH_3O$—), 3.38-3.33 (m, —$OCH_2CHCH_3O$—) 1000H, 2.38 (s, —$OCH_2CH_2N_3$), 1.11-1.08 (m, —$OCH_2CHCH_3O$—) 190H.

$^{13}$C NMR (75.7 MHz, $CDCl_3$, 25° C., δ ppm): 75.0, 74.8, 74.6, 72.8, 72.5, 72.4, 70.1, 50.2, 17.0, 16.9.

IR (NaCl, thin solid film): —$N_3$ 2245 $cm^{-1}$

Example 3

Preparation of the diamine Derivative of the Surfactant Pluronic® F127 (BASF)

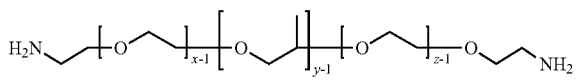

Pluronic® F127 diamine 500 mg of Pluronic® F127 diazide (0.04 mmol) and 31 mg of triphenylphosphine (0.12 mmol) were dispersed in 5.0 mL of anhydrous THF. The minimum necessary amount of anhydrous $CH_2Cl_2$ was added to this mixture in order to obtain an homogeneous solution, that was kept under an inert atmosphere and stirred overnight. 1.0 mL of water was then added and the organic solvent removed using a rotary evaporator The reaction mixture was redissolved in a 5% $NaHCO_3$ aqueous solution and then saturated with solid NaCl and then extracted 6-8 times with $CH_2Cl_2$. The solid obtained by removal of the solvent via evaporation at low pressure was redispersed in water and separated from the by-products by means of dialysis in water (regenerated cellulose membrane, cut-off 10KDa).

$^1$H NMR (300 MHz, $CDCl_3$, 25° C., δ ppm): 3.83-3.80 (m, 4H, —$OCH_2CH_2O$—$CH_2CH_2NH_2$); 3.59 (s, —$OCH_2CH_2O$—), 3.52-3.50 (m, —$OCH_2CHCH_3O$—) 3.36-3.36 (m, —$OCH_2CHCH_3O$—) 1000H, 2.64 (s, —$OCH_2CH_2NH_2$), 1.09-1.08 (m, —$OCH_2CHCH_3O$—) 190H.

$^{13}$C NMR (75.7 MHz, $CDCl_3$, 25° C., δ ppm): 75.0, 74.9, 74.7, 72.9, 72.6, 72.5, 70.1, 68.2, 17.0, 16.9.

Example 4

Preparation of the dicarboxylic acid Derivative of the Surfactant Pluronic® F127 (BASF)

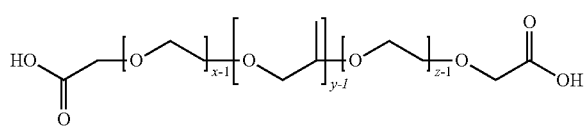

Pluronic® F127 dicarboxylic acid 12.60 g of Pluronic® F127 (1.0 mmol) and 1750 mg of sodium metaperiodate ($NaIO_4$, 8.2 mmol) were placed in a 250 mL round-bottom flask. 60 mL of water, 24 mL of acetonitrile and 21 mL of carbon tetrachloride were added to this mixture. 9.1 mg of RuCl$_3$.3H$_2$O (0.044 mmol, 4.4% in mol) were added to the resulting biphasic solution and the reaction mixture was kept under vigorous magnetic stirring for about 20 hours at room temperature. The reaction mixture was then repeatedly extracted (5-6 times) with CH$_2$Cl$_2$. The reunited organic phases were dried over Na$_2$SO$_4$, filtered, evaporated at low pressure, affording a white solid (75% yield).

$^1$H NMR (300 MHz, CDCl$_3$, 25° C., δ ppm): 4.05 (s, 4H, —CH$_2$COOH); 3.52 (s, —OCH$_2$CH$_2$O—), 3.43 (m, —OCH$_2$CHCH$_3$—), 3.29 (m, —OCH$_2$CHCH$_3$O—) 1000H, (d, —OCH$_2$CHCH$_3$O—) 190H.

$^{13}$H NMR (75.7 MHz, CDCl$_3$, 25° C., δ ppm): 75.2, 75.0, 74.8, 73.0, 72.6, 70.2, 17.1.

IR (NaCl, thin solid film): —COOH 1735 cm$^{-1}$

Alternative synthetic strategies which implies the direct introduction of the carboxyl moiety through the oxidation of the hydroxylic groups at the ends of the surfactant Pluronic® F127 are:

Oxidation with NaClO/TEMPO:
Anelli, P. L.; Biffi, C.; Montanari, F.; Quici, S. *J. Org. Chem.* 1987, 52, 2559-2562.
Adam, W.; Saha-Moller, C. R.; Ganeshpure, P. A. *Chem. Rev.* 2001, 101, 3499-3548. Ref.: 200-203.

Oxidation with RuCl$_3$/H$_2$O$_2$:
Barak, G.; Dakka, J.; Sasson, Y. *J. Org. Chem.* 1988, 53, 3553-3555.

Oxidation with pyridiunium chlorochromate
Hunsen, M. *Synthesis*, 2005, 2487-2490.
Corey, E. J.; Gras, J.-L.; Ulrich, P. *Tetrahedron Lett.* 1976, 11, 809.

Oxidation with o-iodobenzoic acid and Oxone®
Thottumkara, A. P.; Bowsher, M.; S. Vinod, T. K. *Org. Lett.* 2005, 7, 2933-2936.

Example 5

Preparation of the dicarboxylic Acid Derivative II of the Surfactant Pluronic® F127 (BASF)

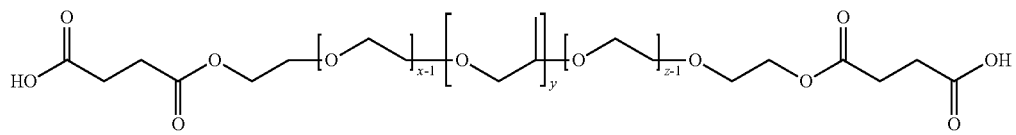

Pluronic® F127 dicarboxylic acid II 2.00 g of Pluronic® F127 (0.16 mmol) and 10 mL of anhydrous toluene were placed in a 100 mL round-bottom flask. The solvent was evaporated at 70° C. at low pressure and then 31.8 mg of succinic anhydride (0.32 mmol) were added. The reaction was kept at 80° C. under stirring overnight, then cooled, affording the reaction product as a white solid (quantitative yield).

$^1$H NMR (300 MHz, CDCl$_3$, 25° C., δ ppm): 4.10 (t, 4H, —COOCH$_2$CH$_2$COOH), 3.74 (m, 4H, —CH$_2$COOCH$_2$CH$_2$COOH), 3.51 (s, —OCH$_2$CH$_2$O—), 3.42-3.41 (m, —OCH$_2$CHCH$_3$O—), 3.28-3.27 (m, —OCH$_2$CHCH$_3$O—) 1000H, 2.49 (t, 4H, —COOCH$_2$CH$_2$COOH), 1.01-0.99 (m, 190H, —OCH$_2$CHCH$_3$O—).

$^{13}$C NMR (75.7 MHz, CDCl$_3$, 25° C., δ ppm): 173.0, 171.8, 75.0, 74.9, 74.8, 74.7, 72.9, 72.4, 70.1, 68.6, 68.1, 63.3, 28.8, 28.417.0, 16.9.

IR (NaCl, thin solid film): —COOH, 1726 cm$^{-1}$

Example 6

Preparation of the dithiol Derivative of the Surfactant Pluronic® F127 (BASF)

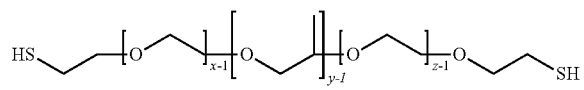

Pluronic® F127 dithiol

A solution consisting of 7.0 mL of EtOH 95% (v/v), 1.00 g of Pluronic® F127 dimesylate (0.078 mmol) and 13 mg of thiourea (0.16 mmol) was heated at reflux for 3 hours. A solution of NaOH (7.5 mg, 0.21 mmol) in H$_2$O (1.0 mL) was added to the reaction mixture, keeping it at reflux for another 2 hours. Once cooled down, the mixture was neutralized with a 10% HCl solution and extracted with CH$_2$Cl$_2$.

$^1$H NMR (300 MHz, CDCl$_3$, 25° C., δ ppm): 4.26 (t, 4H, —OCH$_2$CH$_2$SH); 3.76 (t, 4H, —OCH$_2$CH$_2$O—CH$_2$CH$_2$SH); 3.55 (s, —OCH$_2$CH$_2$O—), 3.45-3.39 (m, —OCH$_2$CHCH$_3$O—), 3.29-3.28 (m, —OCH$_2$CHCH$_3$O—) 1000H, 3.01 (m, 4H, —OCH$_2$CH$_2$SH); 2.63 (s, broad, —OCH$_2$CH$_2$SH), 1.02-1.01 (m, —OCH$_2$CHCH$_3$O—) 190H.

$^{13}$C NMR (75.7 MHz, CDCl$_3$, 25° C., δ ppm): 75.1, 74.9, 74.7, 73.0, 72.6, 72.5, 72.4, 70.2, 69.7, 68.6, 68.2, 17.1, 17.0.

Example 6

Synthesis of Nanoparticles with —COOH Moieties (Pluronic® F127/Pluronic® F127 dicarboxylic acid) Containing the fluorophore The synthesis of samples having four different percentages of modified surfactant (1.0-2.0-3.0-5.0%) with respect to the total quantity in moles of surfactants in the reaction mixture is hereby described by way of example.

The following components were mixed and kept under stirring at the temperature of 25° C. for 1 hour and 45 minutes:

Pluronic® F127: 200-x mg (where x is the quantity in mg of modified Pluronic® surfactant)

Pluronic® F127 dicarboxylic acid surfactant (whose preparation was described in example 4): x mg (x=2.0, 4.0, 6.0, 10.0 mg for the percentages 1.0-2.0-3.0-5.0% respectively)

Rhodamine B piperazine functionalized with triethoxysilane moieties: 0.62 mg, 0.7E-6 mol 0.85 M solution of HCl: 3130 mg TEOS: 308 mg (0.330 mL)

After the aforementioned time DEDMS (diethoxydimethylsilane) was added: 26 mg (0.030 mL).

The whole mixture was kept under stirring for an additional 48 hours at 25° C.

The obtained solution of nanoparticles was then subjected to dialysis in bidistilled water with regenerated cellulose membranes (cut-off 10 KDa).

The dimensional distributions of these particles are illustrated in figures from 4 to 7.

Figure 23:
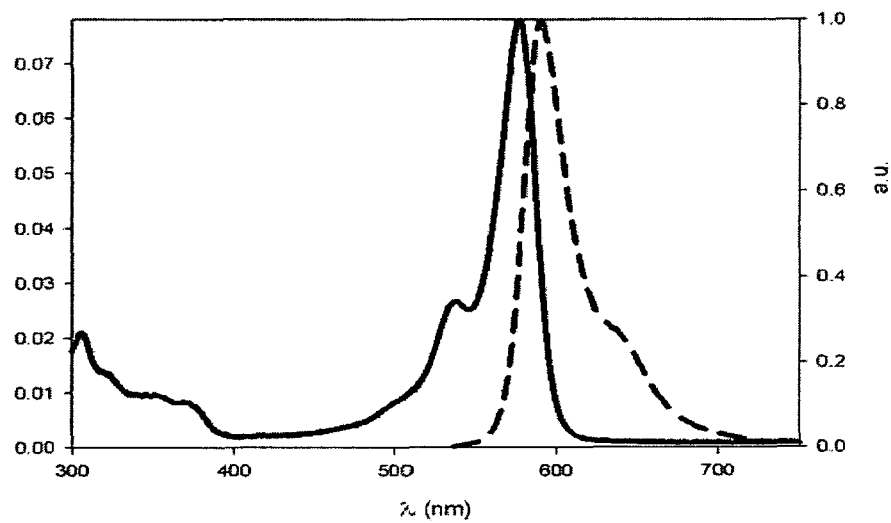
FIG. 23 shows the absorbance spectrum (solid line) and the emission spectrum (dashed line) of rhodamine B piperazine.

FIG. 23 shows the absorption spectrum (solid line) and the fluorescence emission spectrum (dotted line) of rhodamine B piperazine (the wavelengths are reported on the x-axis; absorbance—on the left—and luminescence intensity—on the right—are reported on the y-axis) in EtOH.

Figure 24:
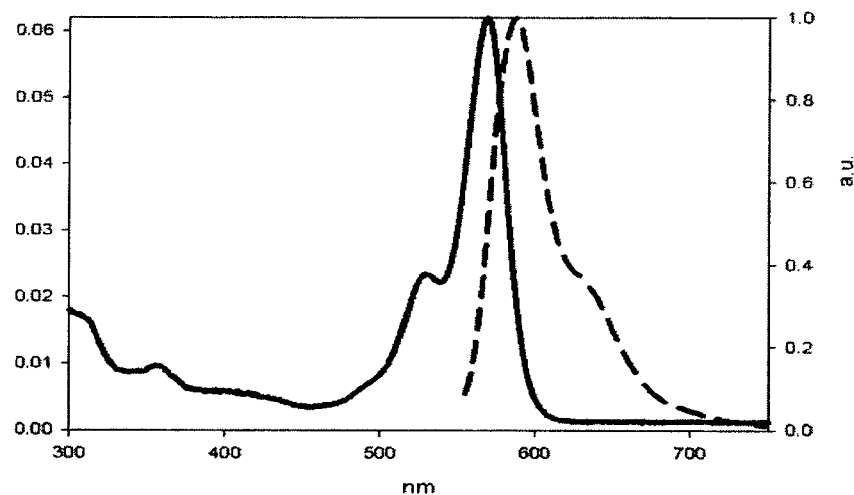
FIG. 24 shows the absorbance spectrum (solid line) and the emission spectrum (dashed line) of particles containing rhodamine B piperazine functionalized with triethoxysilane moieties.

FIG. 24 shows the absorption spectrum (solid line) and the fluorescence emission spectrum (dotted line) of particles containing rhodamine B piperazine functionalized with triethoxysilane moieties (the wavelengths are reported on the x-axis; absorbance—on the left—and luminescence intensity—on the right—are reported on the y-axis) in $H_2O$.

Example 7

Synthesis of Nanoparticles with —$N_3$ Moieties (Pluronic® F127/Pluronic® F127 diazide) Containing the Fluorophore Rhodamine B Piperazine Functionalized with Triethoxysilane Moieties The synthesis of samples having four different percentages of modified surfactant (1.0-2.0-3.0-5.0%) with respect to the total quantity in moles of surfactants in the reaction mixture is hereby described by way of example.

The following components were mixed and kept under stirring at the temperature of 25° C. for 1 hour and 45 minutes:

Pluronic® F127: 200-x mg (where x is the quantity in mg of modified Pluronic® surfactant)

Pluronic® F127 diazide surfactant: x mg (x=2.0, 4.0, 6.0, 10.0 mg for the percentages 1.0-2.0-3.0-5.0% respectively)

Rhodamine B piperazine functionalized with triethoxysilane moieties: 0.62 mg, 0.7E-6 mol 0.85 M solution of HCl: 3130 mg TEOS: 308 mg (0.330 mL)

After the aforementioned time DEDMS (diethoxydimethylsilane) was added: 26 mg (0.030 mL).

The whole mixture was kept under stirring for an additional 48 hours at 25° C.

The obtained solution of nanoparticles was then subjected to dialysis in bidistilled water with regenerated cellulose membranes (cut-off 10 KDa).

The dimensional distributions of these particles are illustrated in figures from 8 to 11.

Example 8

Synthesis of Biotin-$PEO_3$-PropargylAmine

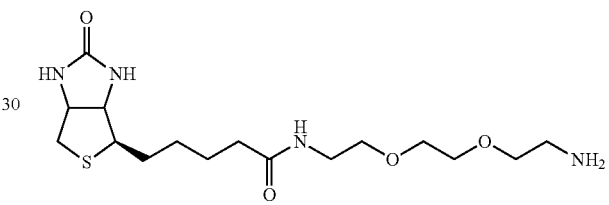

Biotin-$PEO_3$-Amine, Cyanagen S.R.L. (Bologna)

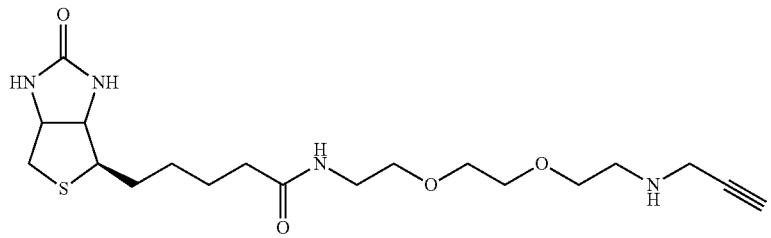 [SMILES: C#CCNCCOCCOCCNC(=O)CCCC[C@H]1SCC2NC(=O)NC21]

Biotin-$PEO_3$-PropargylAmine

35 µL of propargyl p-toluenesulfonate were dissolved in 300 µL of anhydrous DMF. This solution was added at room temperature during one hour in aliquots of 50 µL to a solution consisting of 26 mg of Biotin-$PEO_3$-Amine (68 µmol) and 19 µL of triethylamine (0.136 mmol) dissolved in 500 µL of anhydrous DMF. The reaction mixture was then kept under stirring at room temperature for 20 hours and successively dried at low pressure. The reaction product was used in the following steps for the functionalization of the particles without any further purification.

Example 9

Preparation of Biotinylated Nanoparticles Starting from Pluronic® F127/Pluronic® F127 Dicarboxylic Acid Nanoparticles Containing The Fluorophore Rhodamine B Piperazine Functionalized with the Triethoxysilane Moiety The coupling reaction between Biotin-PEO$_3$-Amine and the nanoparticles functionalized with carboxylic groups was carried out on aliquots of 1000 μL of dialyzed solution of nanoparticles. Considering the synthetic conditions and the dilution occurred during the dialysis, the quantities in mol of carboxylic groups in this volume are (the percentages in mol of modified surfactant with respect to the total amount of surfactant are shown between brackets): 2.6E-8 mol (1.0%); 4.8E-8 mol (2.0%); 7.2E-7 mol (3.0%); 1.2E-7 mol (5.0%).

100 μL of PBS buffer solution 10× (pH 7.4), 50 μL of N-hydroxysuccinimide (NHS) solution 1.87 M in PBS 1× (pH 7.4) and 50 μL of 1-Ethyl-3-(3-dimethylaminopropyl) carbodiimide hydrochloride (EDC.HCl) solution 1.1 M in PBS 1× (pH 7.4) were added to 1000 μL of dialyzed solution of particles. After 2 hours of stirring at room temperature, 54 μL of a Biotin-PEO$_3$-Amine solution 83E-3 M in PBS 1× (pH 7.4) were added to the reaction mixture. 12 hours later, a second aliquot of 50 μL of 1-Ethyl-3-(3-dimethylaminopropyl)carbodiimide hydrochloride (EDC.HCl) solution 2.6 M in PBS 1× (ph 7.4) was added to the reaction mixture, which was then kept under stirring for another 20 hours and finally subjected to dialysis vs. PBS buffer solution 1× (pH 7.4).

The dialyzed solution wad diluted up to 5.00 mL with a PBS buffer solution 1× (pH 7.4).

Example 10

Synthesis of Biotinylated Nanoparticles Starting from Pluronic® F127/Pluronic® F127 Diazide Nanoparticles (Reaction with Cu(0)-Cu(II)/tris(triazolyl)amine)

150 μL of PBS buffer solution 10× (pH 7.4), 100 μL of a Biotin-PEO$_3$-propargylamine solution 0.051M in tert-butanol, 100 μL of a tris(triazolyl)amine suspension 0.025M in PBS 1× (pH 7.4), 63 μL of a CuSO$_4$ solution in water ([Cu (II)]=0.020 M) and a small fragment of copper wire were added to 1000 μL of a dialyzed solution of particles synthesized in accordance with example 7. The reaction was kept under stirring for 20 hours at room temperature and then the reaction mixture was subjected to dialysis vs. a PBS buffer solution 1× (pH 7.4).

The dialyzed solution wad diluted up to 5.00 mL with a PBS buffer solution 1× (pH 7.4).

Example 11

Synthesis of Biotinylated Nanoparticles Starting from Pluronic® F127/Pluronic® F127 diazide Nanoparticles (Reaction with Cu(II)/Sodium ascorbate/tris(triazolyl)amine)

The coupling reaction between Biotin-PEO$_3$-Amine and the nanoparticles functionalized with azide groups was carried out on aliquots of 1000 μL of dialyzed solution of nanoparticles. Considering the synthetic conditions and the dilution occurred during the dialysis, the quantities in moles of azide groups in this volume are: 2.4E-8 mol (1.0%); 5.0E-8 mol (2.0%); 7.3E-7 mol (3.0%); 1.2E-7 mol (5.0%).

150 μL of PBS buffer solution 10× (pH 7.4), 100 μL of a Biotin-PEO$_3$-propargylamine solution 0.051M in tert-butanol, 100 μL of a tris(triazolyl)amine suspension 0.025M in PBS 1× (pH 7.4), 63 μL of a CuSO$_4$ solution in water ([Cu (II)]=0.020 M) and 13 μL of a sodium ascorbate solution 0.20 M in PBS 1× (pH 7.4). The reaction was kept under stirring for 20 hours at room temperature and then the reaction mixture was subjected to dialysis vs. a PBS buffer solution 1× (pH 7.4).

The dialyzed solution wad diluted up to 5.00 mL with a PBS buffer solution 1× (pH 7.4).

Example 12

Agglutination Tests with avidin of Biotinylated Nanoparticles

An indirect method, that consist of monitoring by means of DLS technique (Dynamic Light Scattering) the aggregation (agglutination) of particles promoted by the presence of avidin (or streptavidin), was used to check if the functionalization of nanoparticles with biotin had really occurred.

The agglutination titration were carried out in PBS buffer 1× (pH 7.4) by adding to different samples, in which the concentration of nanoparticles is constant (about 3E-8 M), increasing amounts of avidin (3.7E-9 M; 1.8E-8 M; 3.7E-8 M; 3.7E-7 M). DLS measurements were performed after an incubation time of about 2 hours.

The results are shown in some summarizing graphs (FIGS. 12, 13 and 14) in which the average hydrodynamic diameter resulting form the addition of avidin at different concentration is reported.

Figure 12:
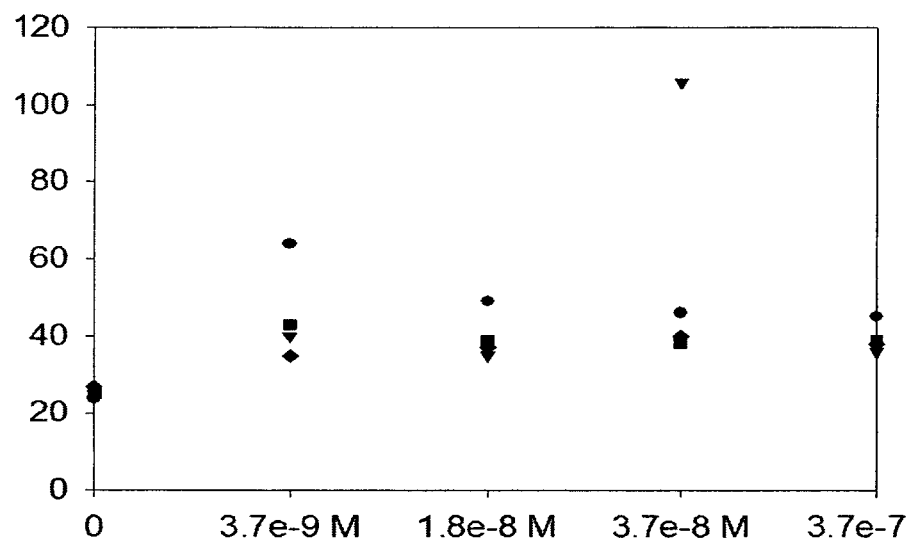

Particles synthesized in accordance with example 9, FIG. 12: ● represents tests performed with particles, in which the percentage of functionalized surfactant with respect to the total amount of surfactant is 1%; ▼ represents tests performed with particles, in which the percentage of functionalized surfactant with respect to the total amount of surfactant is 2%; ■ represents tests performed with particles, in which the percentage of functionalized surfactant with respect to the total amount of surfactant is 3%; ♦ represents tests performed with particles, in which the percentage of functionalized surfactant with respect to the total amount of surfactant is 5%.

Figure 13:
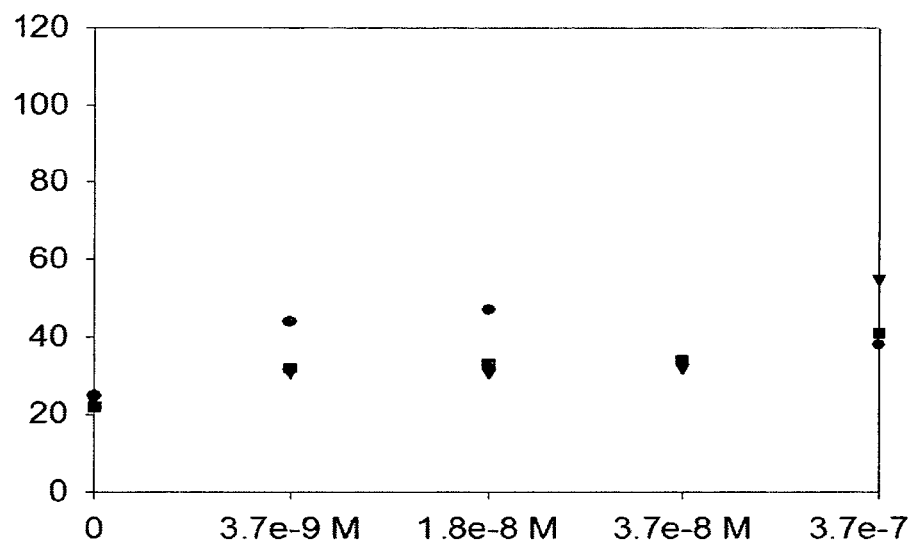
Figure 15:
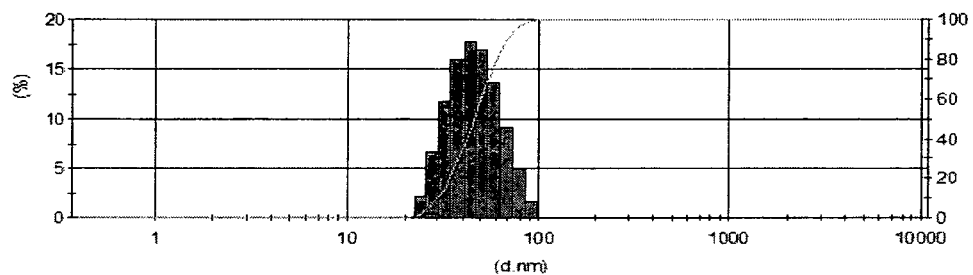
FIGS. 15 to 19 show the dimensional distribution obtained by means of DLS (dynamic light scattering) technique for the agglutination processes depicted with the • symbol in FIG. 14 (the diameter expressed in nm is reported on the x-axis)
Figure 16:
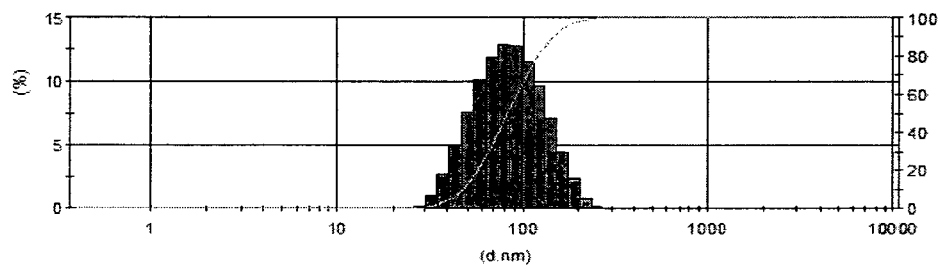
Figure 17:
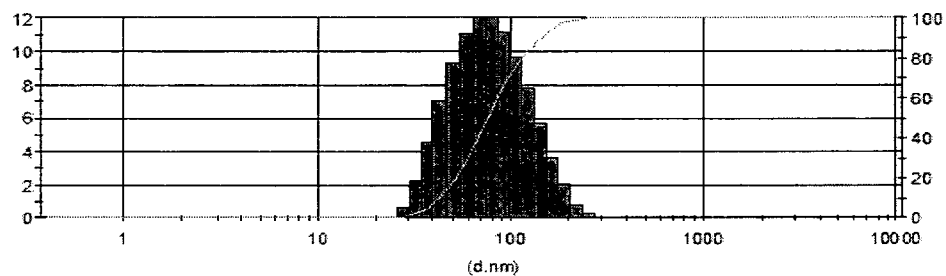
Figure 18:
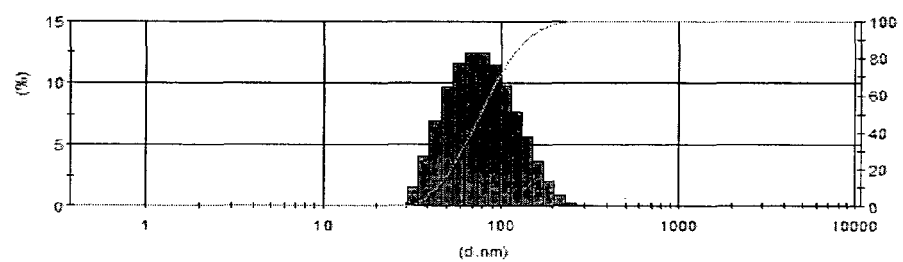
Figure 19:
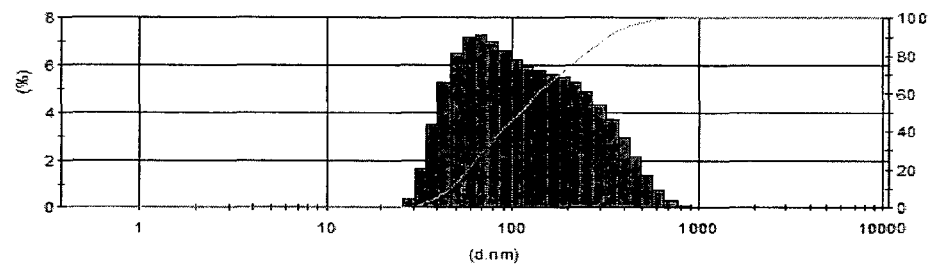

Particles synthesized in accordance with example 10, FIG. 13: ● represents tests performed with particles, in which the percentage of functionalized surfactant with respect to the total amount of surfactant is 1%; ▼ represents tests performed with particles, in which the percentage of functionalized surfactant with respect to the total amount of surfactant is 2%; ■ represents tests performed with particles, in which the percentage of functionalized surfactant with respect to the total amount of surfactant is 5%.

Figure 14:
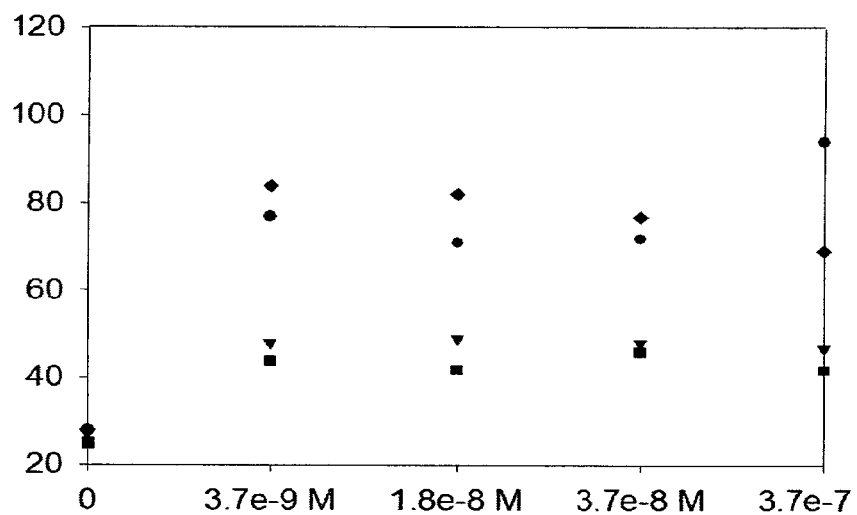
FIGS. 12, 13 and 14 are graphs that shows the average hydrodynamic diameter (on the y-axis, expressed in nm) measured during agglutination processes of biotinylated particles in accordance with the present invention as a function of avidin concentration (on the x-axis, expressed in mol/L)

Particles synthesized in accordance with example 11, FIG. 14: ● represents tests performed with particles, in which the percentage of functionalized surfactant with respect to the total amount of surfactant is 1%; ▼ represents tests performed with particles, in which the percentage of functionalized surfactant with respect to the total amount of surfactant is 2%; ■ represents tests performed with particles, in which the percentage of functionalized surfactant with respect to the total amount of surfactant is 3%; ♦ represents tests performed with particles, in which the percentage of functionalized surfactant with respect to the total amount of surfactant is 5%.

As an example, the dimensional distributions resulting in the agglutination experiments for the particles described in example 11 (Pluronic® F127 diazide 1%) are reported in figures from 15 to 19.

Example 13

Preparation of Particles

An amount of active compound in between 0.03E-6 and 8.00E-5 moles was mixed with 200 mg of surfactant (Pluronic® F127) and 10 mg of the Pluronic® F127 dicarboxylic acid derivative described in example 4.

To the mixture of the solids a small amount of dichloromethane (1-5 mL) was added in order to obtain an homogeneous solution of the surfactants and the active compound.

The organic solvent was then quantitatively evaporated under vacuum. To the obtained solid, 3130 mg of acidic aqueous solution were added (for example HCl 0.85M, alternatively it is possible to use also a basic solution) and stirred at room temperature. 336 mg (0.360 mL) of TEOS were added to the homogeneous obtained solution, and after 1 h and 45 min, 26 mg (0.030 mL) of DEDMS (diethoxydimethylsilane) or TMSCl (chlorotrimethylsilane) were added.

The reaction mixture was maintained under continuous stirring for another 48 hours.

Examples of lipophilic compounds that were used are: cyanines CY7 e CY5 (previously mentioned), 4-(Dicyanomethylene)-2-methyl-6-(4-dimethylaminostyryl)-4H-pyran (Aldrich 410497), Bis(1-phenylisoquinoline)(acetylacetonate)iridium(III) (Ir(III)(pq)$_2$acac), Tris(2-phenylpyridine)iridium(III), Ir(ppy)$_3$, 9,10-diphenylanthracene, rubrene, Red Nile, naphthalocyanines (previously mentioned), N,N□-Bis(2,5-di-tert-butylphenyl)-3,4,9,10-perylenedicarboximide.

Figure 22:
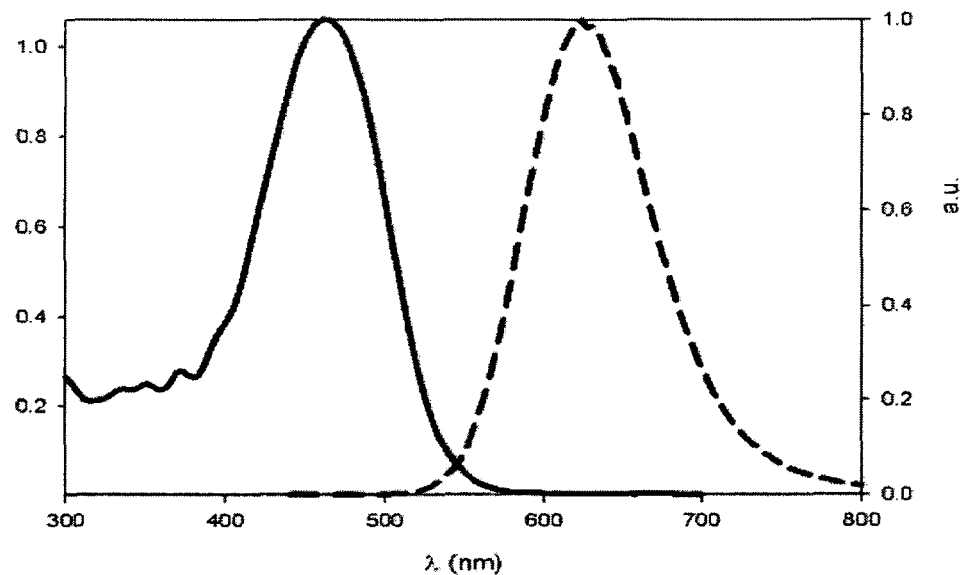
FIG. 22 shows the absorbance spectrum (solid line) and the fluorescence emission spectrum (dashed line) of 4-(Dicyanomethylene)-2-methyl-6-(4-dimethylaminostyryl)-4H-pyran in ethanol.

FIG. 22 shows the absorption spectrum (solid line) and the fluorescence emission spectrum (dotted line) of 4-(Dicyanomethylene)-2-methyl-6-(4-dimethylaminostyryl)-4H-pyran

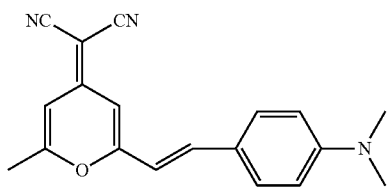

(the wavelengths are reported on the x-axis; absorbance—on the left—and luminescence intensity—on the right—are reported on the y-axis) in acetonitrile.

Figure 2:
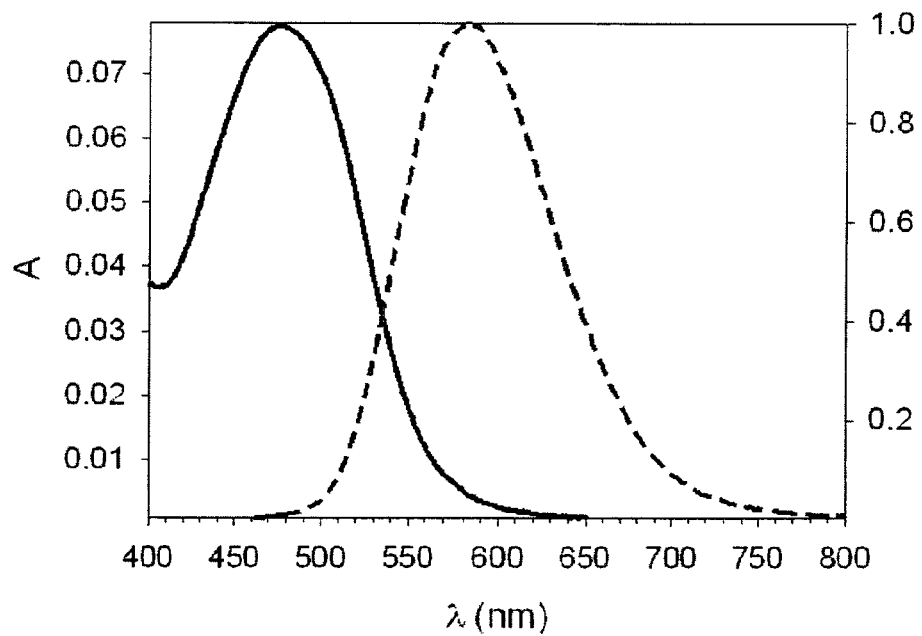
FIG. 2 shows the absorbance spectrum (solid line) and the emission spectrum (dashed line) of particles in accordance with the present invention and comprising 4-(Dicyanomethylene)-2-methyl-6-(4-dimethylaminostyryl)-4H-pyran (conc. 0.05% vs. moles of TEOS) in water, $\lambda_{exc}$=455 nm.
Figure 3:
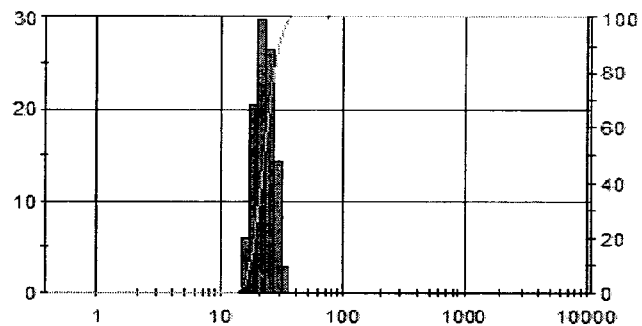
FIG. 3 shows the dimensional distribution obtained by means of DLS (dynamic light scattering) technique of the particles of FIG. 2 (d=23 nm, PDI=0.15) (the diameter expressed in nm is reported on the x-axis)
Figure 4:
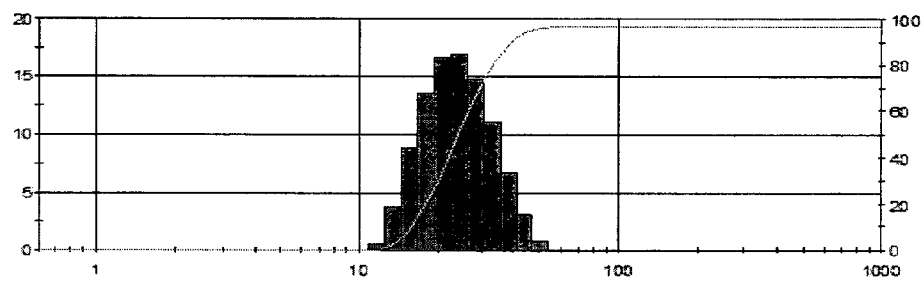
FIGS. 4, 5, 6 and 7 show the dimensional distribution obtained by means of DLS (dynamic light scattering) technique of the particles in accordance with the present invention with rhodamine B piperazine with triethoxysilane moieties and with the surfactants Pluronic® F127 and 1.0%, 2.0%, 3.0%, 5.0% (with respect to the total amount of surfactants) Pluronic® F127 dicarboxylic acid, respectively (the diameter in nm is reported on the x-axis)
Figure 5:
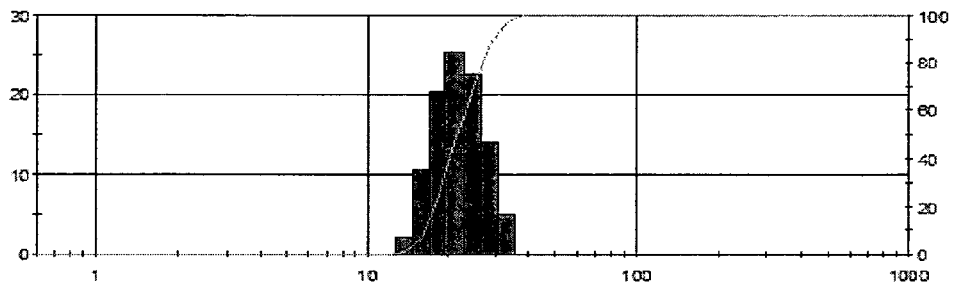
Figure 6:
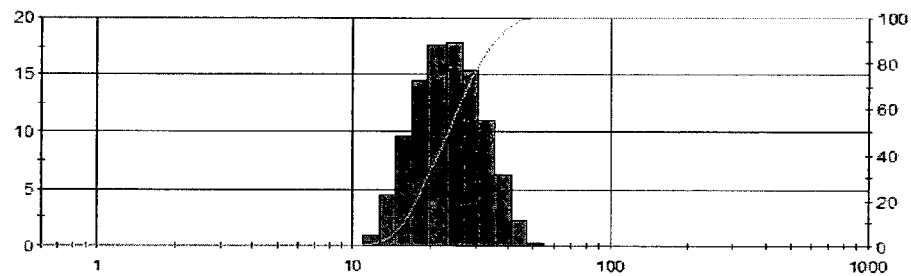
Figure 7:
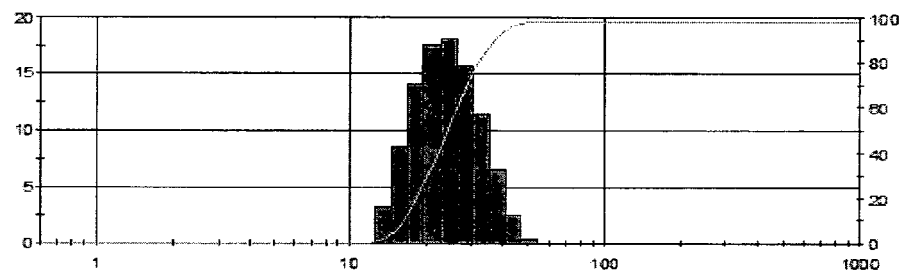
Figure 8:
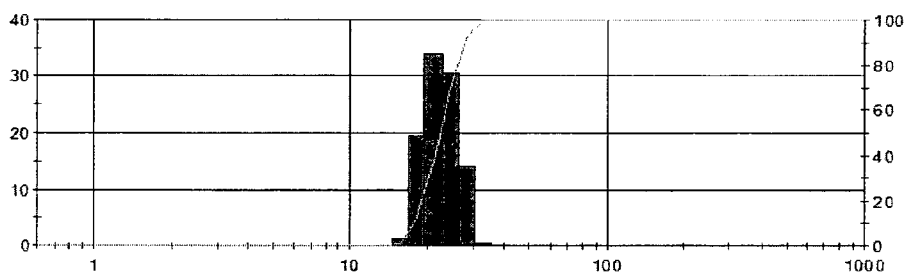
FIGS. 8, 9, 10 and 11 show the dimensional distribution obtained by means of DLS (dynamic light scattering) technique of the particles in accordance with the present invention with rhodamine B piperazine functionalized with triethoxysilane moieties and with the surfactants Pluronic® F127 and 1.0%, 2.0%, 3.0%, 5.0% (with respect to the total amount of surfactants) Pluronic® F127 diazide, respectively (the diameter expressed in nm is reported on the x-axis)
Figure 9:
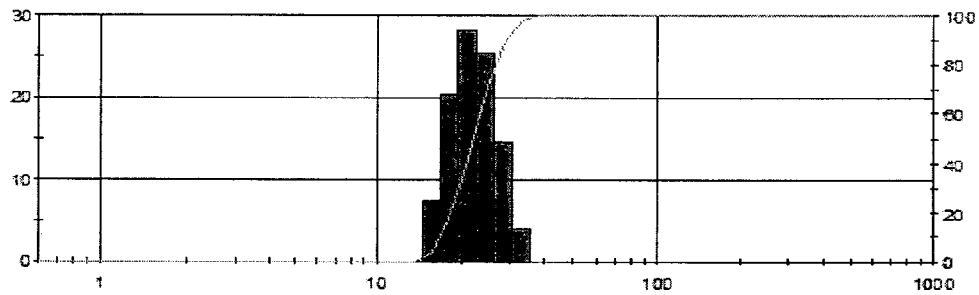
Figure 10:
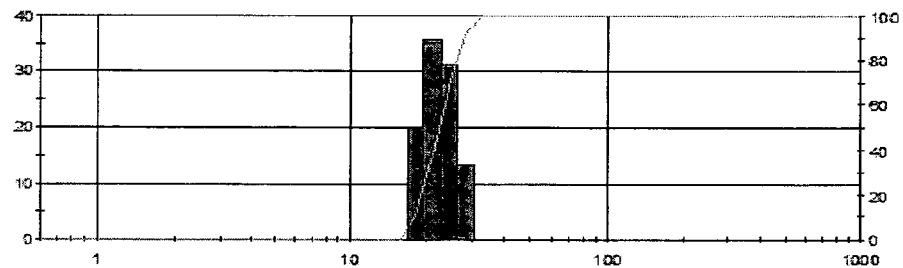
Figure 11:
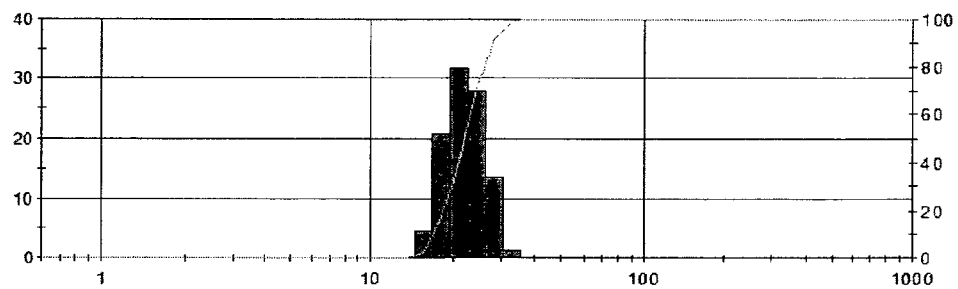

FIG. 2 shows the absorption spectrum (solid line) and the fluorescence emission spectrum (dotted line) of particles containing 4-(Dicyanomethylene)-2-methyl-6-(4-dimethylaminostyryl)-4H-pyran (the wavelengths are reported on the x-axis; absorbance—on the left—and luminescence intensity—on the right—are reported on the y-axis) in H$_2$O.

Example 14

Functionalization of Particles Described in Example 13

Particles described in example 13 containing—(Dicyanomethylene)-2-methyl-6-(4-dimethylaminostyryl)-4H-pyran were conjugated with a probe peptide with the following methodology: 25 µL of a MES (2-(N-morpholino)ethanesulfonic acid) buffer solution 0.2 M (pH 6.0), 25 µL of NHS 0.2 M in water and 25µ of EDC.HCl 0.2 M were added to 975 µL of a dialyzed solution of particles. The solution was kept under stirring for 3 hours, then 200 µL of PBS 10× (pH 7.4) and 50 µL of a peptide solution 0.1 M in DPBS 1× (Dulbecco's phosphate saline buffer) were added. After about 12 hours, the reaction mixture was subjected to dialysis (regenerated cellulose membrane, cut-off 10 KDa) against a PBS buffer solution 1× (pH 7.4).

These particles conjugated with peptides were tested on biological tissues that contained compatible substrates for those peptides. It was possible to identify with the naked eye the position and, approximately, estimate the amount of the aforementioned substrates.

Example 15

Synthesis of dansyl-propargylamine

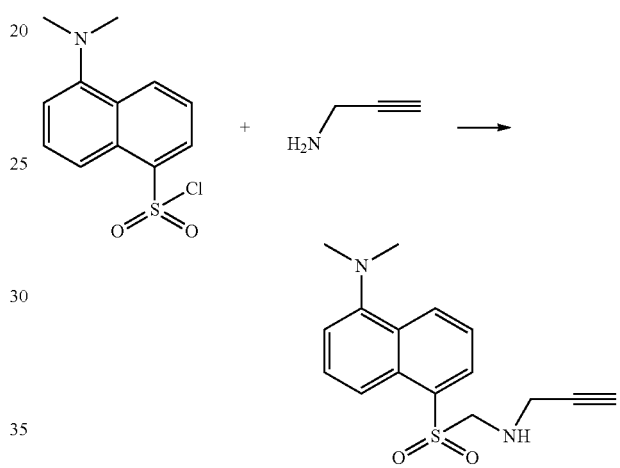

234 mg of dansyl chloride (0.87 mmol) and 4.0 mL of anhydrous dichloromethane were placed in a 25 mL round-bottom flask equipped with a CaCl$_2$ trap. 240 µL of triethylamine (1.73 mmol) and 330 µL of propargylamine (5.20 mmol) were added to the solution, which was then kept under stirring for 12 hours at room temperature. The residue obtained by distillation under reduced pressure was redissolved in some mL of tetrahydrofuran and the resulting mixture was filtrated. The evaporation of the solvent of the filtrated solution under reduced pressure affords the product in quantitative yield.

$^1$H NMR (300 MHz, CDCl$_3$, 25° C., δ ppm): 8.42 (d, 1H), 8.19-8.15 (m, 2H), 7.44-7.34 (m, 2H), 7.04 (d, 1H) H$_{arom}$ dansyl, 5.43 (s broad, 1H, —NHCH$_2$C≡CH), 3.66 (d, 2H, —NHCH$_2$C≡CH), 2.74 (s, 6H, —N(CH$_3$)$_2$), 1.79 (t, 1H, —NHCH$_2$C≡CH).

$^{13}$C NMR (75.7 MHz, CDCl$_3$, 25° C., δ ppm): 151.7, 134.2, 130.5, 129.6, 129.5, 128.3, 122.9, 118.5, 115.0, 77.9, 72.4, 45.2, 32.7.

Example 16

Synthesis of Nanoparticles with dansyl Groups on the Surface

Nanoparticles with the azide functional group non containing the rhodamine B piperazine derivative were obtained following the synthesis described in example 7 (Pluronic® F127/Pluronic® F127 diazide). Superficial functionalization of these particles was accomplished through the reaction of the —N₃ moieties of the particles with dansyl propargylamine.

Different samples were synthesized, in which the percentage of Pluronic® F127 diazide was 1, 6, 10, 30% with respect to the total amount in mol of surfactant in the reaction mixture. The functionalization reaction took place as follows:

particles Pluronic® F127/Pluronic® F127 diazide 1-6-10%:

0.50 mL of Mill-Q water, 2.9 mg of dansyl propargylamine (0.01 mmol), 20 μL of CuSO₄ 0.025 M (0.0005 mmol) and 20 μL of sodium ascorbate 0.05 M (0.001 mmol) were added to 0.50 mL of a nanoparticles solution previously subjected to dialysis against water. The reaction mixture was kept under stirring for 36 hours at room temperature, and then subjected to ultrafiltration with Mill-Q water, using a 75 mL Millipore ultrafiltration cell equipped with 47 mm filters (regenerated cellulose, cu-off 100 kDa). The ultrafiltration was protracted until there was no sign of dansyl fluorescence in the filtrated solution. The retentate solution was then recovered, after it was concentrated to a volume of 5.0 ml.

particles Pluronic® F127/Pluronic® F127 diazide 30%:

0.50 mL of Mill-Q water, 8.64 mg of dansyl propargylamine (0.03 mmol), 20 μL of CuSO₄ 0.075 M (0.0015 mmol) and 20 μL of sodium ascorbate 0.15 M (0.003 mmol) were added to 0.50 mL of a nanoparticles solution previously subjected to dialysis against water. The reaction mixture was kept under stirring for 36 hours at room temperature, and then subjected to ultrafiltration with Mill-Q water, using a 75 mL Millipore ultrafiltration cell equipped with 47 mm filters (regenerated cellulose, cu-off 100 kDa). The ultrafiltration was protracted until there was no sign of dansyl fluorescence in the filtrated solution. The retentate solution was then recovered, after it was concentrated to a volume of 5.0 ml.

Figure 25:
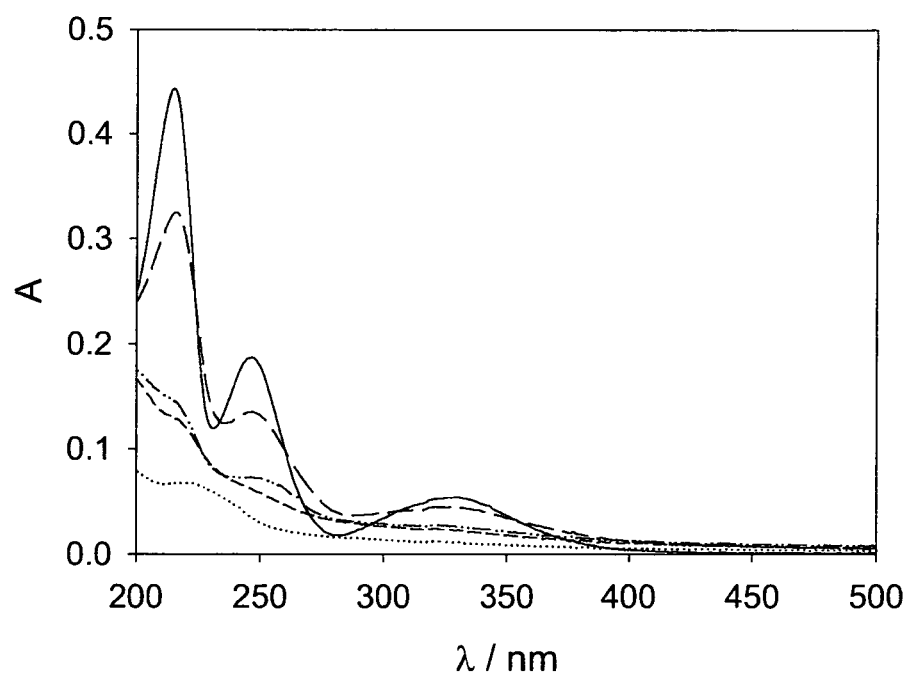
FIG. 25 shows the absorbance spectra of dansyl propargylamine (in water) as reference and of the nanoparticles samples obtained following the methodology described in the experimental procedure (_____ dansyl propargylamine; . . . nanoparticles Pluronic® F127/Pluronic® F127 diazide 1%; ------ nanoparticles Pluronic® F127/Pluronic® F127 diazide 6%; . ._. ._. ._nanoparticles Pluronic® F127/Pluronic® F127 diazide 10%; - - - nanoparticles Pluronic® F127/Pluronic® F127 diazide 30%)

FIG. 25 shows the absorbance spectra of dansyl propargylamine (in water) as reference and of the nanoparticles samples obtained following the methodology previously described in the experimental procedure (_____ dansyl propargylamine; . . . nanoparticles Pluronic® F127/Pluronic® F127 diazide 1%; ------ nanoparticles Pluronic® F127/Pluronic® F127 diazide 6%; . ._. ._. ._nanoparticles Pluronic® F127/Pluronic® F127 diazide 10%; - - - nanoparticles Pluronic® F127/Pluronic® F127 diazide 30%). It is clear that the absorption bands (300-350 nm) distinctive of the dansyl moiety increase in intensity proportionally to the percentage of modified surfactant (Pluronic® F127 diazide) and consequently to the degree of functionalization of the particle.

Figure 26:
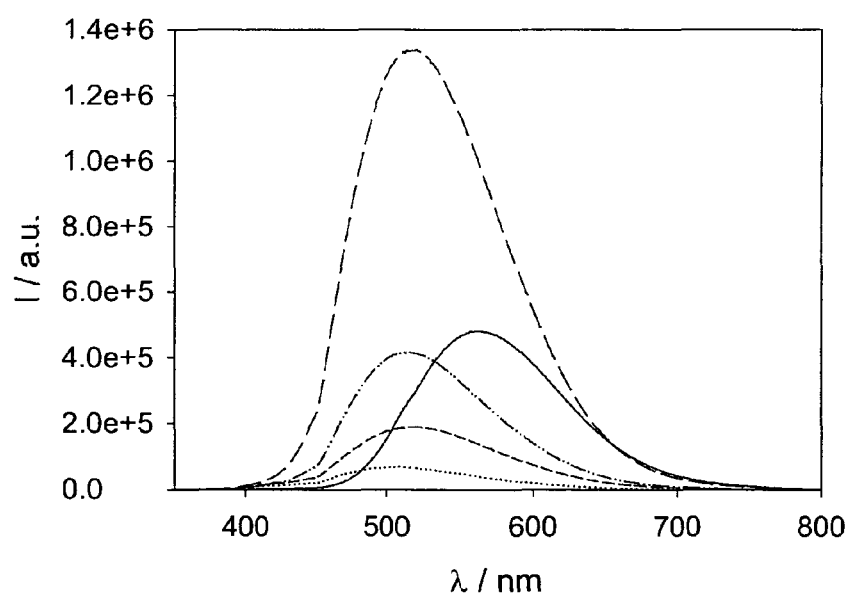
FIG. 26 shows the absorbance spectra ($\lambda_{ex}$=340 nm) of dansyl propargylamine (in water) as reference and of the nanoparticles samples obtained following the methodology described in the experimental procedure (_____ dansyl propargylamine; . . . nanoparticles Pluronic® F127/Pluronic® F127 diazide 1%; ------ nanoparticles Pluronic® F127/Pluronic® F127 diazide 6%; Pluronic®._._._._.nanoparticles Pluronic® F127/Pluronic® F127 diazide 10%; - - - nanoparticles Pluronic® F127/Pluronic® F127 diazide 30%)

FIG. 26 shows the emission spectra ($\lambda_{ex}$=340 nm) of dansyl propargylamine (in water) as reference and of the nanoparticles samples obtained following the methodology previously described in the experimental procedure (_____ dansyl propargylamine; . . . nanoparticles Pluronic® F127/Pluronic® F127 diazide 1%; ------ nanoparticles Pluronic® F127/Pluronic® F127 diazide 6%; . ._. ._. ._nanoparticles Pluronic® F127/Pluronic® F127 diazide 10%; - - - nanoparticles Pluronic® F127/Pluronic® F127 diazide 30%). It is clear that the emission bands distinctive of the dansyl moiety increase in intensity proportionally to the percentage of modified surfactant (Pluronic® F127 diazide) and consequently to the degree of functionalization of the particle.

Example 17

Synthesis of DNS-APTES (3-(dansylamino)propyltriethoxysilane)

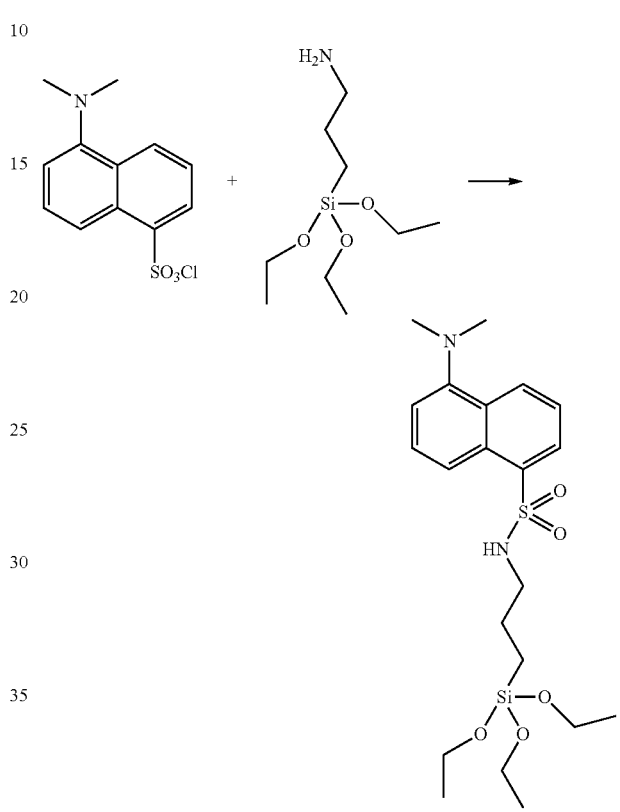

For the experimental procedure, see: Rampazzo E.; Brasola E.; Marcuz S.; Mancin F.; Tecilla P.; Tonellato U. *J. Mater. Chem.* 2005, 15, 2687-2696.

Example 18

Synthesis of NBD-APTES ((7-nitrobenzofurazan-4-yl)-(3-triethoxysilylpropyl)-amine)

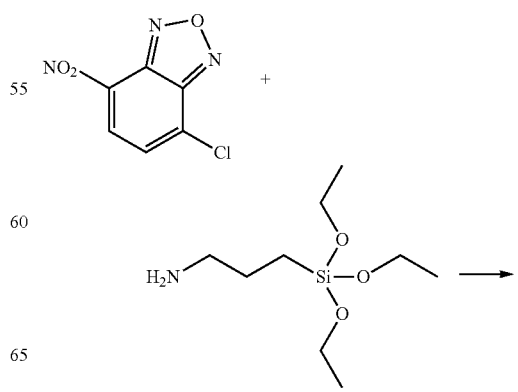

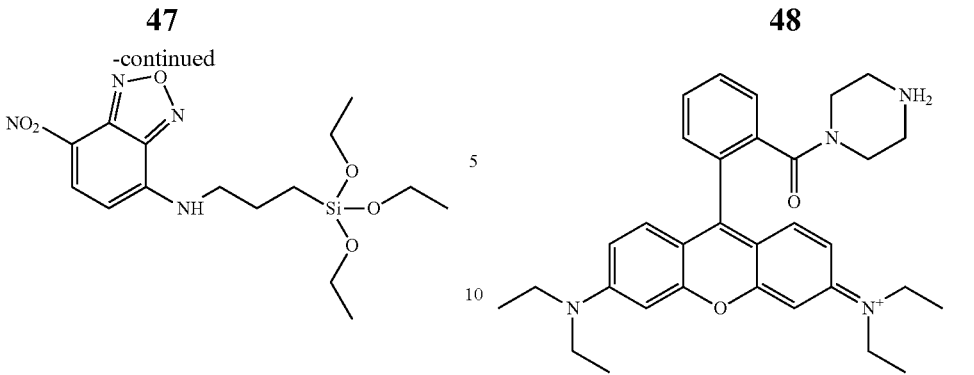

For the experimental procedure, see: Rampazzo E.; Brasola E.; Marcuz S.; Mancin F.; Tecilla P.; Tonellato U. *J. Mater. Chem.* 2005, 15, 2687-2696.

Example 19

Synthesis of 2-(3-triethoxysilyl-propyl)-benzo[de]isoquinoline-1,3-dione

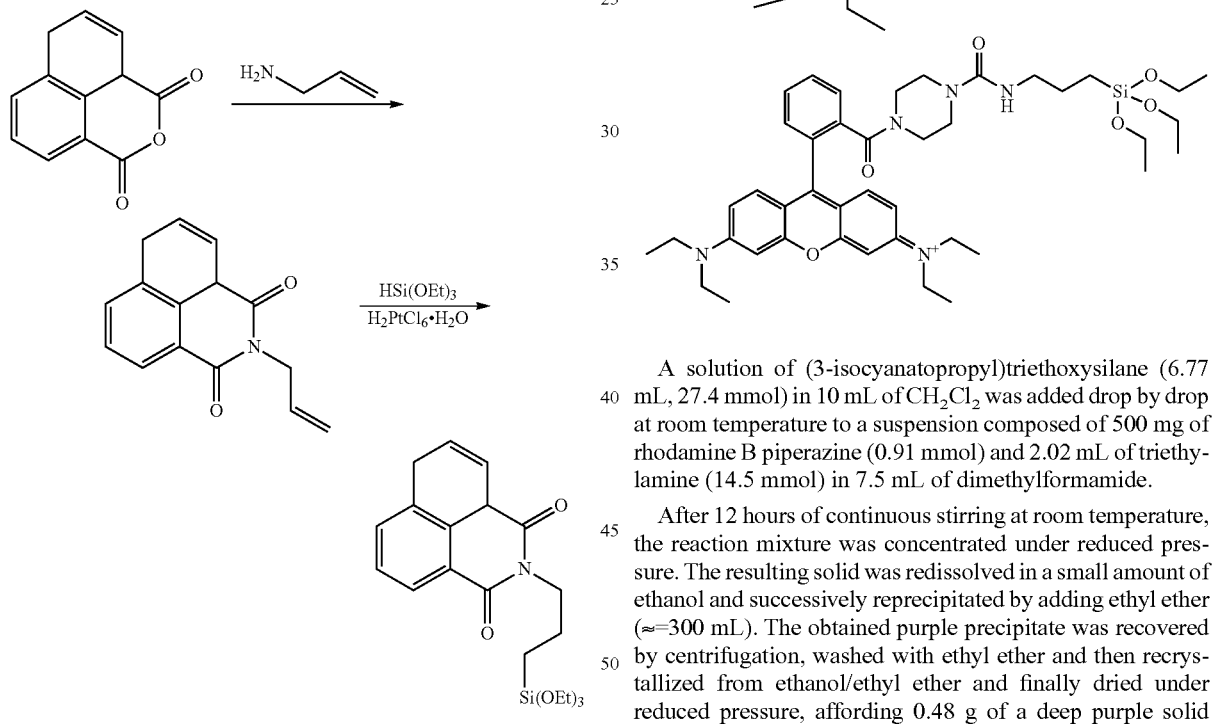

For the experimental procedure, see: Rampazzo E.; Brasola E.; Marcuz S.; Mancin F.; Tecilla P.; Tonellato U. *J. Mater. Chem.* 2005, 15, 2687-2696.

Example 20

Synthesis of Rhodamine B Piperazine Functionalized with Triethoxysilane Moiety

The precursor compound for the synthesis was rhodamine B piperazine, whose synthesis is described by Nguyen, T. et al. in *Org. Lett.* 2003, 5, 3245-3248.

A solution of (3-isocyanatopropyl)triethoxysilane (6.77 mL, 27.4 mmol) in 10 mL of $CH_2Cl_2$ was added drop by drop at room temperature to a suspension composed of 500 mg of rhodamine B piperazine (0.91 mmol) and 2.02 mL of triethylamine (14.5 mmol) in 7.5 mL of dimethylformamide.

After 12 hours of continuous stirring at room temperature, the reaction mixture was concentrated under reduced pressure. The resulting solid was redissolved in a small amount of ethanol and successively reprecipitated by adding ethyl ether (≈300 mL). The obtained purple precipitate was recovered by centrifugation, washed with ethyl ether and then recrystallized from ethanol/ethyl ether and finally dried under reduced pressure, affording 0.48 g of a deep purple solid (yield 65%).

$^1$H NMR (250 MHz, $CD_3OD$, 25° C., δ ppm): 0.59 (t, 2H, J=8.1 Hz), 1.19 (t, J=7.3 Hz) and 1.33 (t, J=8.4 Hz) 21H partially overlapping, 1.57 (m, 2H), 3.09 (t, J=6.9 Hz) and 3.25 (q, J=7.3 Hz) partially overlapping 8H, 3.40 (broad s, 2H), 3.65-3.73 (q, J=7.3 Hz) and 3.76-3.86 (q, J=7.3 Hz,) partially overlapping 14H, 6.97 (d, J=2.6 Hz), 7.05-7.09 (dd, 2H, J=2.6 Hz), 7.27-7.30 (d, 2H, J=9.5 Hz), 7.50-7.54 (m, 1H), 7.67-7.79 (m, 3H).

$^{13}$C NMR (62.9 MHz, $CD_3OD$, 25° C., δ ppm) δ 8.52, 9.10, 12.88, 18.70, 24.60, 44.54, 46.92, 47.54, 59.46, 97.34, 114.86, 115.46, 128.98, 131.28, 131.77, 132.32, 133.24, 136.62, 139.09, 157.12, 157.19, 159.27, 159.80, 169.50.

ESI-MS, m/z (M+H$^+$) 758.6.

Elemental Analysis
Calculated: C, 71.69; H, 7.22; N, 8.36.
Found: C, 71.41; H, 7.24; N, 8.38.

Example 21

Synthesis of 8-oxo-3-propylaminotriethoxysilyl-8H-acenaphtho[1,2-b]pyrrol-9-carbonitrile The synthesis of the compound was obtained starting from precursor 1, whose synthesis, as well as the synthesis of the model compound 8-Oxo-3-propylamino-8H-acenaphtho[1,2-b]pyrrol-9-carbonitrile, is described by Xiao Y. et al. in *Chem. Commun.*, 2005, 239.

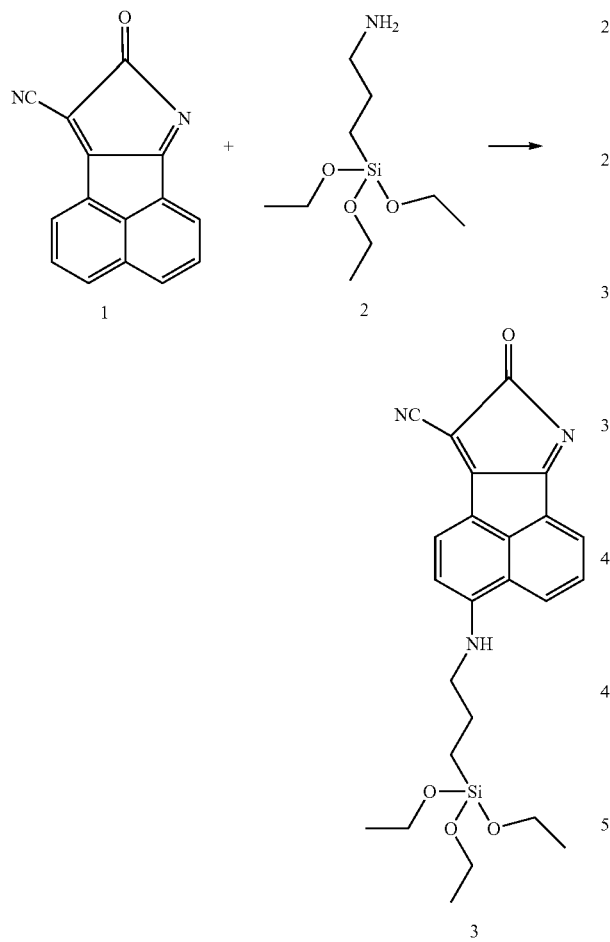

A solution of (3-aminopropyl)triethoxysilane (5.07 mL, 21.72 mmol) in 30 mL of acetonitrile was added at room temperature to a suspension of 1 (1.00 g, 4.3 mmol) in 100 mL of the same solvent. The reaction mixture changed color from yellow-brown to deep red (TLC: dichloromethane and dichloromethane/ethanol 10/0.2). The solvent was removed under reduced pressure and the residue was solubilized with a small quantity of diethyl ether. Then, petroleum ether was added (about 400 mL) and the resulting suspension was filtered. The solid was then purified by flash chromatography on silica gel (dichloromethane/ethanol 10/0.2) obtaining 330 mg of 8-oxo-3-propylaminotriethoxysilyl-8H-acenaphtho[1,2-b]pyrrol-9-carbonitrile (3, yield 15%) as a yellow-golden solid.

$^1$H NMR (250 MHz, CDCl$_3$, 25° c., δ ppm) δ: 0.78 (t, 2H, J=8.1 Hz), 1.15 (t, 9H, J=7.3 Hz), 2.01 (m, 2H), 3.76 (q, 6H, J=7.3 Hz), 4.07 (q, J=7.3 Hz), 7.58-7.71 (m, 3H), 8.04 (t, 2H, J=2.6 Hz), 8.35 (d, 1H, J=9.5 Hz), 8.45-8.49 (dd, 1H, 3J=7.0 Hz, 4J=0.9 Hz).

$^{13}$C NMR (62.9 MHz, CDCl$_3$, 25° C., δ ppm) δ: 7.6, 18.7, 23.9, 47.6, 58.9, 84.9, 118.8, 123.2, 125.6, 126.4, 127.3, 127.5, 127.8, 129.5, 132.6, 134.3.

ESI-MS, m/z (M+H$^+$) 450.2.

Example 22

Synthesis of 1-(3-(trimethoxysilyl)propyl)-4,4'-bipyridin-1-ium and 1,1'-bis(3-(trimethoxysilyl)propyl)-4,4'-bipyridinium

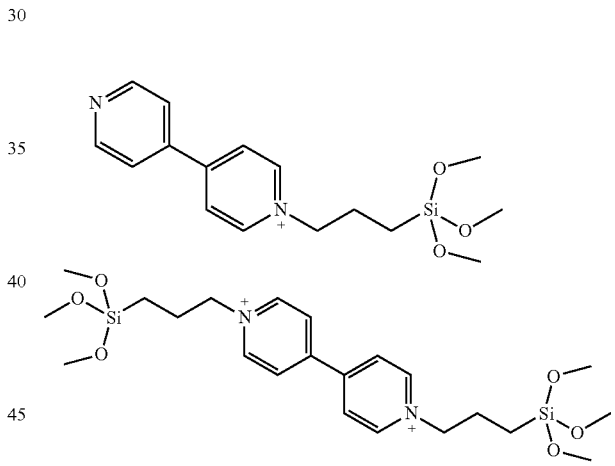

For the experimental procedure, see for example: Alvaro, M.; Ferrer, B.; Garcia, H.; Hashimoto, S.; Hiratsuka, M.; Asahi, T.; Masuhara, H. *ChemPhysChem* 2004, 5, 1058-1062.

Example 23

Trialkoxysilane Derivatives of fulleropyrrolidine and fullerene C$_{60}$

For the experimental procedure, see for example: Bianco, A.; Maggini, M.; Nogarole, M.; Scorrano, G. *European Journal of Organic Chemistry* 2006, 13, 2934-2941 or Kraus, A.; Schneider, M.; Gugel, A.; Mullen, K. *Journal of Materials Chemistry* 1997, 7, 763-765.

Example 24

Synthesis of triethoxysilane Derivative of the bis(2,2'-bipyridyl)-[4-(4'-methyl-2,2'-bipyridin-4-yl)butan-1-amine]ruthenium(II) Complex

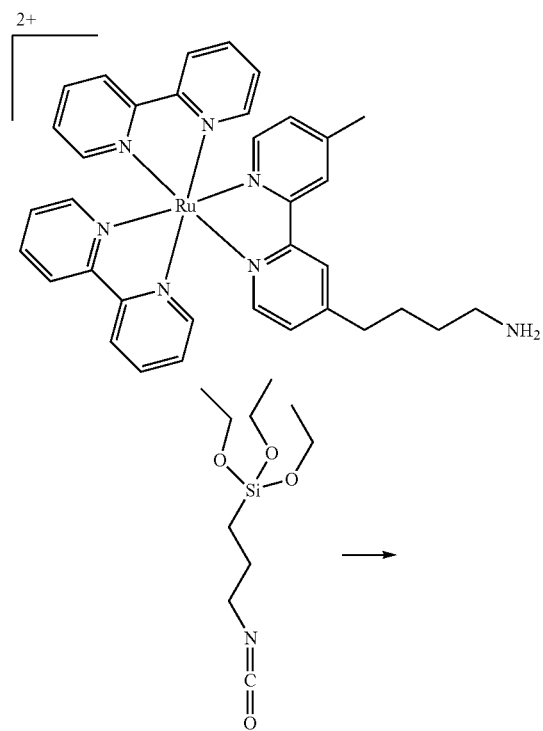

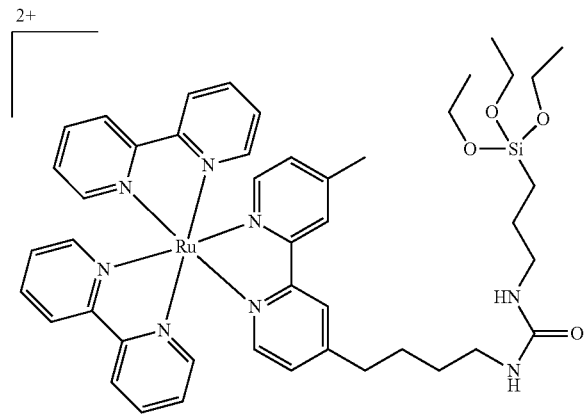

The compound can be easily synthesized with almost quantitative yields at room temperature by reacting equimolar amounts of bis(2,2'-bipyridyl)-[4-(4'-methyl-2,2'-bipyridin-4-yl)butan-1-amine]ruthenium(II) and (3-isocyanatopropyl)triethoxysilane in dimethylformamide or dimethyl sulfoxide as solvent. The product can be isolated through evaporation of the solvent or used as crude mixture.

ESI-MS ($CH_3CN$), m/z ($M/2+CH_3CN$) 470-471-472.

Example 25

Synthesis of (3-ferrocenylamide)propyl)triethoxysilane and of (3-ferrocenylacetamide)propyl)triethoxysilane

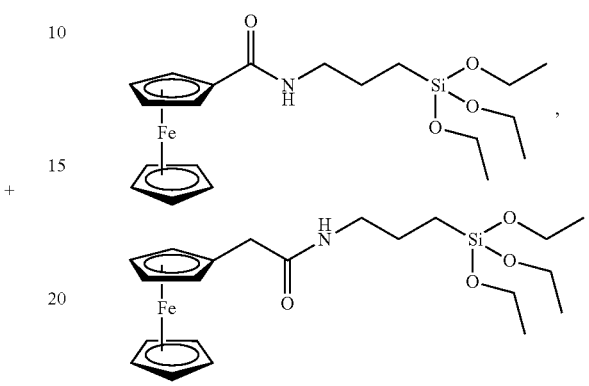

For the experimental procedure; see for example: Delacote, C.; Bouillon, J.-P.; Walcarius, A. *Electrochimica Acta* 2006, 51, 6373-6383 or Budny, A.; Novak, F.; Plumere, N.; Schetter, B.; Speiser, B.; Straub, D.; Mayer, H. A.; Reginek, M. *Langmuir* 2006, 22, 10605-10611 or Jennane, J.; Boutros, T.; Giasson, R. *Can. J. Chem.* 1996, 74, 2509-2517.

Example 26

Preparation of Particles

Rhodamine B piperazine functionalized with triethoxysilane moieties (example 20) was used as the active compound.

The following components were mixed and kept under stirring at the temperature of 25° C. for 1 hour and 45 minutes:

Pluronic® F127: 200 mg 1.1E-3 mol of active compound 0.85 M solution of HCl: 3130 mg TEOS: 336 mg (0.360 mL)

After the aforementioned time, 26 mg (0.030 mL) of DEDMS (diethoxydimethylsilane) were added.

The whole mixture was kept under stirring for an additional 48 hours at 25° C.

FIG. 23 shows the absorption spectrum (solid line) and the fluorescence emission spectrum (dotted line) of rhodamine B piperazine (the wavelengths are reported on the x-axis; absorbance—on the left—and luminescence intensity—on the right—are reported on the y-axis) in EtOH.

Figure 27:
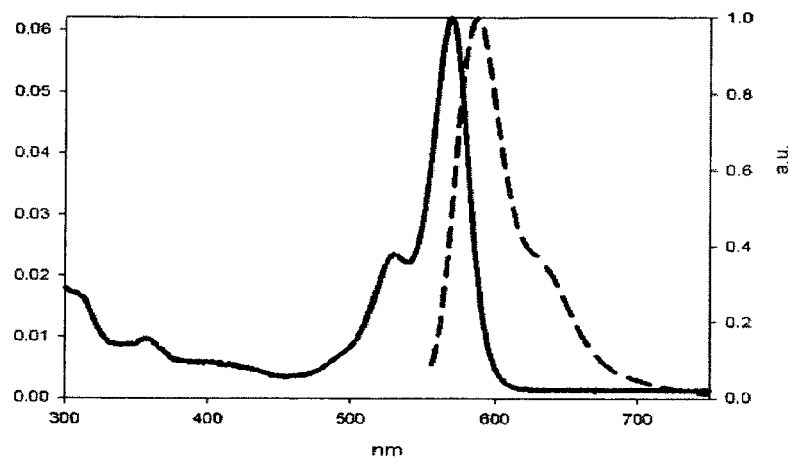
FIG. 27 shows the absorbance spectrum (solid line) and the emission spectrum (dashed line) of particles containing rhodamine B piperazine functionalized with triethoxysilane moieties.

FIG. 27 shows the absorption spectrum (solid line) and the fluorescence emission spectrum (dotted line) of particles containing rhodamine B piperazine functionalized with triethoxysilane moieties (the wavelengths are reported on the x-axis; absorbance—on the left—and luminescence intensity—on the right—are reported on the y-axis) in $H_2O$.

Figure 28:
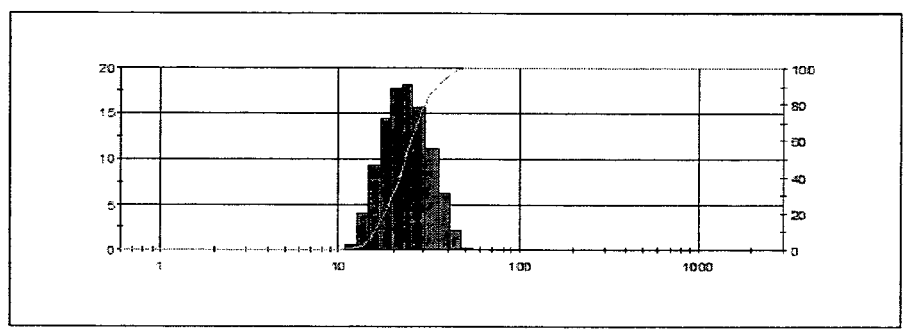
FIG. 28 shows the dimensional distribution obtained by means of DLS (dynamic light scattering) technique of the particles containing rhodamine B piperazine functionalized with triethoxysilane moieties in water (the diameter expressed in nm is reported on the x-axis)

FIG. 28 shows the dimensional distribution obtained by means of DLS technique (dynamic light scattering) of particles containing rhodamine B piperazine functionalized with triethoxysilane moieties in $H_2O$.

Example 27

Preparation of Particles

Rhodamine B piperazine was used as the active compound. The experimental procedure described in the supporting information of the article *J. Am. Chem. Soc.* 2006, 128, 6447-6453 (paragraph 2.4, page S4) was followed.

Example 28

Leaching Tests

Reaction mixtures from examples 26 and 27 were diluted up to 50 mL with Milli-Q water and subjected to dia-ultrafiltration (polyethersulfone membrane, cut-off 50 kDa, diameter 47 mm, 75 mL Millipore cell, P=0.5 atm $N_2$, flux of filtrated solution about 0.20 mL/min, volume of filtrated solution 1300 mL).

Figure 29:
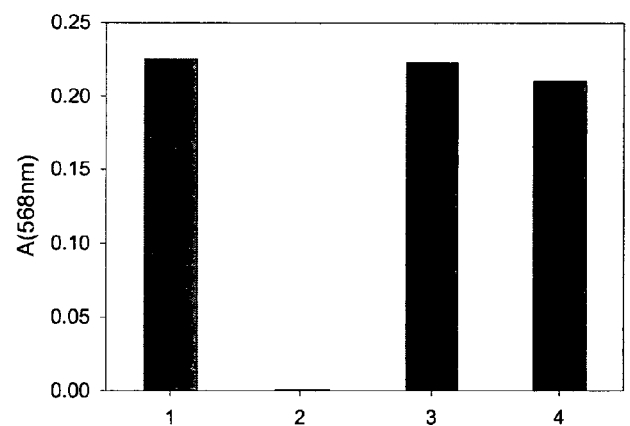
FIG. 29 shows the absorbance of particles in accordance with the present invention containing rhodamine B piperazine functionalized with triethoxysilane moieties (columns 3 and 4) and of particles used for comparison containing rhodamine b piperazine (columns 1 and 2)

The absorbance of the particles of example 27 (FIG. 29, the absorbance at 568 nm is reported on the y-axis), before and after ultrafiltration (column 1 and 2) and of example 26 before and after ultrafiltration (column 3 and 4) was evaluated. As one can notice, the amount of active compound that is kept inside nanoparticles after a prolonged dia-ultrafiltration treatment is clearly different in the two cases. The adoption of derivatives capable of making covalent bonds between the active compound and the silica matrix allows to hold in an almost quantitative way the active compound inside the nanoparticle. The slight decrease of the absorbance of the solution of particles containing the active compound bound covalently after the filtration is likely due to weak adsorption phenomena of particles on the membrane used to carry out the filtration.

Example 29

Preparation of Particles

A quantity of active compound in between 0.03E-6 and 8.00E-5 mol was mixed with 200 mg of surfactant (Pluronic® F127).

A small quantity of dichloromethane (1-5 mL) was added to the mixture of the two solids in order to obtain an homogeneous solution of the surfactant and the active compound.

The organic solvent was then quantitatively evaporated under vacuum. 3130 mg of an acidic aqueous solution were added (for example HCl 0.85 M, alternatively it is possible to use also a basic solution) to the obtained solid and stirred at room temperature. 336 mg (0.360 mL) of TEOS were added to the resulting homogeneous solution, and after 1 h and 45 min, 26 mg (0.030 mL) of DEDMS (dimethyldiethoxysilane) or TMSCl (chlorotrimethylsilane) were added.

The reaction mixture was maintained under continuous stirring for another 48 hours.

Examples of lipophilic compounds that were used are: cyanines CY7 e CY5 (previously mentioned), 4-(Dicyanomethylene)-2-methyl-6-(4-dimethylaminostyryl)-4H-pyran, Bis(1-phenylisoquinoline)(acetylacetonate)iridium(III) (Ir (III)(pq)$_2$acac), Tris(2-phenylpyridine)iridium(III), Ir (ppy)$_3$, 9,10-diphenylanthracene, rubrene, Red Nile, naphthalocyanines (previously mentioned), N,N□-Bis(2,5-di-tert-butylphenyl)-3,4,9,10-perylenedicarboximide.

Hereafter the relative characterizations and some non limiting examples are reported.

Figure 30:
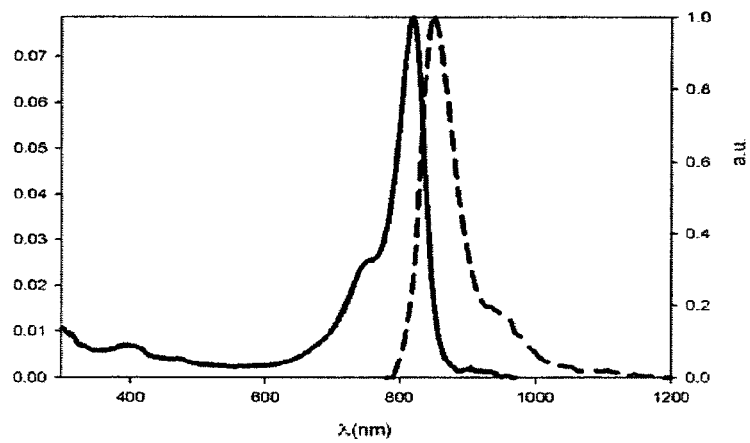
FIG. 30 shows the absorbance spectrum (solid line) and the fluorescence emission spectrum (dashed line) of the CY7ClBIEt cyanine in ethanol.

FIG. 30 shows the absorption spectrum (solid line) and the fluorescence emission spectrum (dotted line) of the cyanine CY7ClBIEt in dichloromethane.

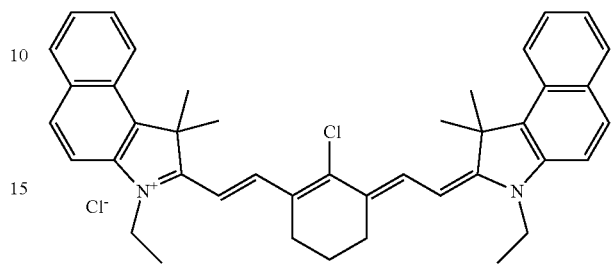

($\lambda_{exc}$=760 nm) (the wavelengths are reported on the x-axis; absorbance—on the left—and luminescence intensity—on the right—are reported on the y-axis) in EtOH.

Figure 31:
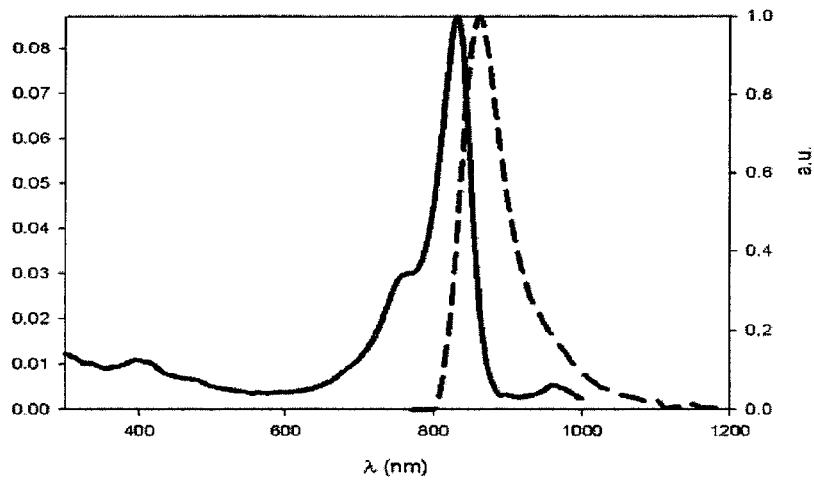
FIG. 31 shows the absorbance spectrum (solid line) and the fluorescence emission spectrum (dashed line) of particles containing the CY7ClBIEt cyanine in water.

FIG. 31 shows the absorption spectrum (solid line) and the fluorescence emission spectrum (dotted line) of particles containing the cyanine CY7ClBIEt ($\lambda_{exc}$=760 nm) (the wavelengths are reported on the x-axis; absorbance—on the left—and luminescence intensity—on the right—are reported on the y-axis) in $H_2O$.

Figure 32:
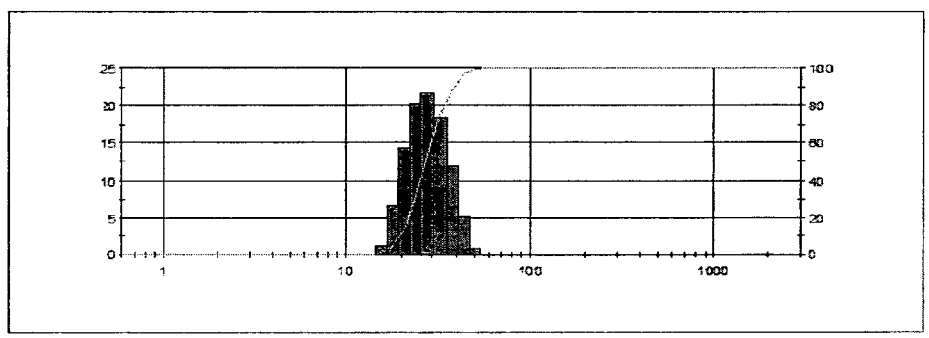
FIG. 32 shows the dimensional distribution obtained by means of DLS (dynamic light scattering) technique of the particles containing the CY7ClBIEt cyanine in water (the diameter expressed in nm is reported on the x-axis)

FIG. 32 shows the dimensional distribution obtained via the DLS (dynamic light scattering) technique for particles containing the cyanine CY7ClBIEt in $H_2O$.

FIG. 22 shows the absorption spectrum (solid line) and the fluorescence emission spectrum (dotted line) of the 4-(Dicyanomethylene)-2-methyl-6-(4-dimethylaminostyryl)-4H-pyran

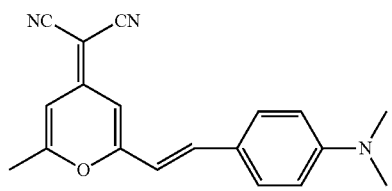

(the wavelengths are reported on the x-axis; absorbance—on the left—and luminescence intensity—on the right—are reported on the y-axis) in acetonitrile.

Figure 33:
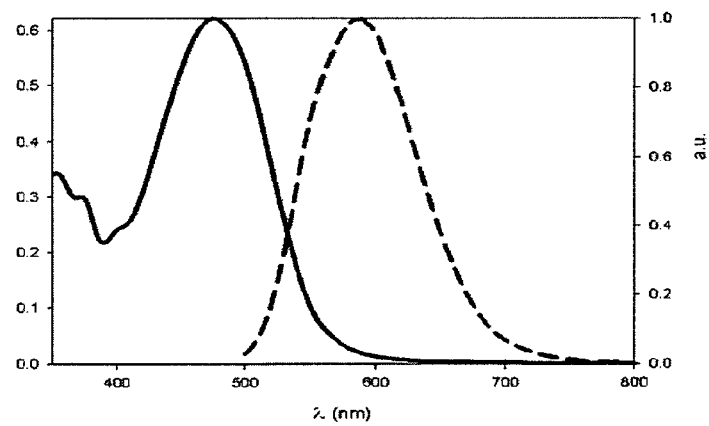
FIG. 33 shows the absorbance spectrum (solid line) and the fluorescence emission spectrum (dashed line) of particles containing 4-(Dicyanomethylene)-2-methyl-6-(4-dimethylaminostyryl)-4H-pyran in water.

FIG. 33 shows the absorption spectrum (solid line) and the fluorescence emission spectrum (dotted line) of particles containing 4-(Dicyanomethylene)-2-methyl-6-(4-dimethylaminostyryl)-4H-pyran (the wavelengths are reported on the x-axis; absorbance—on the left—and luminescence intensity—on the right—are reported on the y-axis) in $H_2O$.

Figure 34:
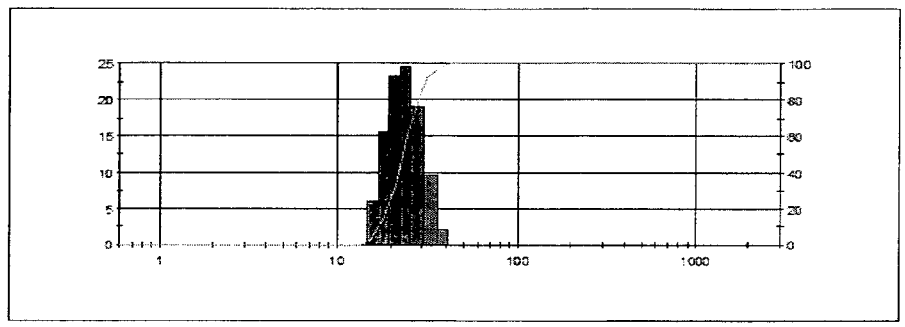
FIG. 34 shows the dimensional distribution obtained by means of DLS (dynamic light scattering) technique of the particles containing 4-(Dicyanomethylene)-2-methyl-6-(4-dimethylaminostyryl)-4H-pyran in water (the diameter expressed in nm is reported on the x-axis)

FIG. 34 shows the dimensional distribution obtained via the DLS (dynamic light scattering) technique for particles containing the 4-(Dicyanomethylene)-2-methyl-6-(4-dimethylaminostyryl)-4H-pyran in $H_2O$.

Figure 35:
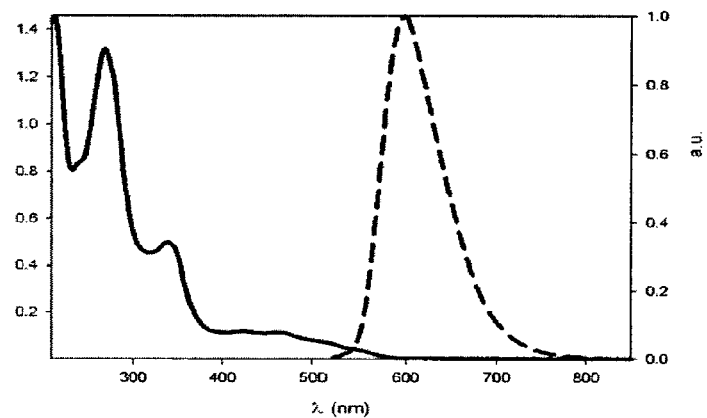
FIG. 35 shows the absorbance spectrum (solid line) and the luminescence emission spectrum (dashed line) of the Bis(1-phenylisoquinoline) (acetylacetonate)iridium(III) (Ir(III)(pq)$_2$acac) complex in ethanol.

FIG. 35 shows the absorption spectrum (solid line) and the fluorescence emission spectrum (dotted line) of the Bis(1-phenylisoquinoline)(acetylacetonate)iridium(III) (Ir(III) (pq)$_2$acac)

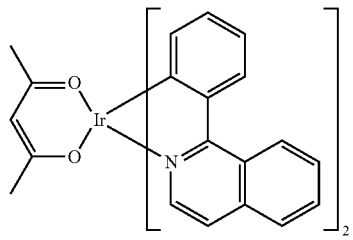

(the wavelengths are reported on the x-axis; absorbance—on the left—and luminescence intensity—on the right—are reported on the y-axis) in EtOH.

Figure 36:
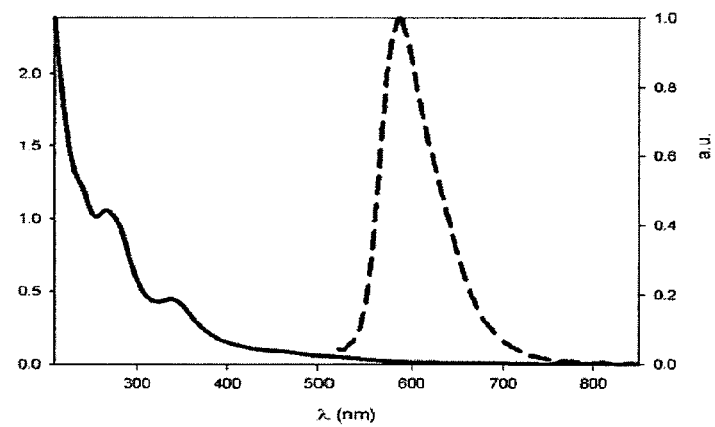
FIG. 36 shows the absorbance spectrum (solid line) and the luminescence emission spectrum (dashed line) of particles containing the Bis(1-phenylisoquinoline)(acetylacetonate) iridium(III) (Ir(III)(pq)$_2$acac) complex in water.

FIG. 36 shows the absorption spectrum (solid line) and the fluorescence emission spectrum (dotted line) of particles containing Bis(1-phenylisoquinoline)(acetylacetonate)iridium (III) (Ir(III)(pq)$_2$acac) (the wavelengths are reported on the x-axis; absorbance—on the left—and luminescence intensity—on the right—are reported on the y-axis) in H$_2$O.

Figure 37:
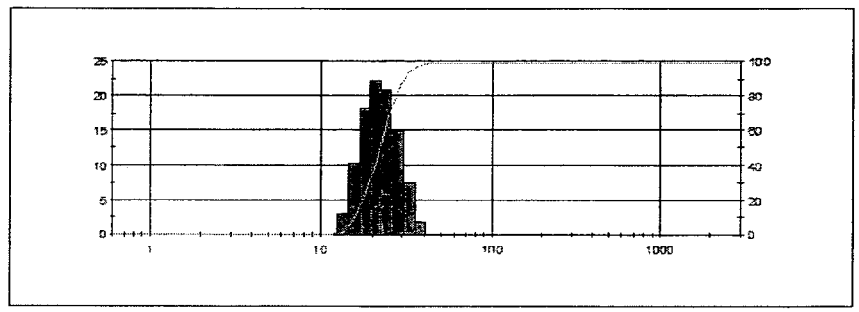
FIG. 37 shows the dimensional distribution obtained by means of DLS (dynamic light scattering) technique of the particles containing the Bis(1-phenylisoquinoline)(acetylacetonate)iridium(III) (Ir(III)(pq)$_2$acac) complex in water.

FIG. 37 shows the dimensional distribution obtained via the DLS (dynamic light scattering) technique for particles containing the Bis(1-phenylisoquinoline)(acetylacetonate) iridium(III) (Ir(III) (pq)$_2$acac) in H$_2$O.

Example 30

Preparation of Particles 8-oxo-3-propylaminotriethoxysilyl-8H-acenaphtho[1,2-b]pyrrol-9-carbonitrile (example 21) was used as the active compound. The procedure described in example 29 was followed.

Figure 38:
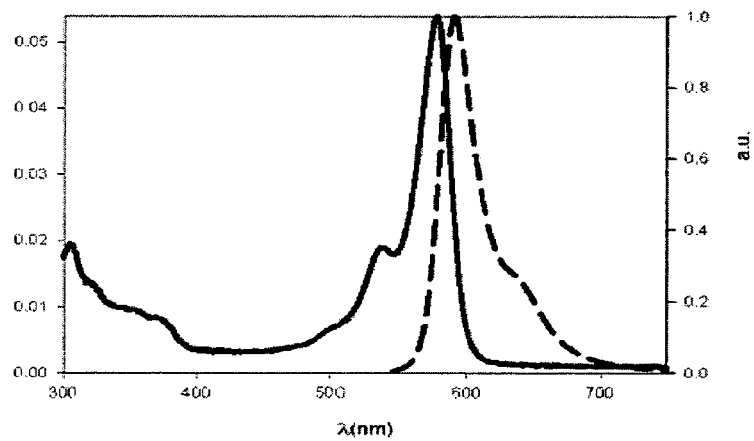
FIG. 38 shows the absorbance spectrum (solid line) and the fluorescence emission spectrum (dashed line) of 8-oxo-3-propylamino-8H-acenaphtho[1,2-b]pyrrol-9-carbonitrile.

FIG. 38 shows the absorption spectrum (solid line) and the fluorescence emission spectrum (dotted line) of the 8-oxo-3-propylamino-8H-acenaphtho[1,2-b]pyrrol-9-carbonitrile ($\lambda_{exc}$=535 nm) (the wavelengths are reported on the x-axis; absorbance—on the left—and luminescence intensity—on the right—are reported on the y-axis) in EtOH.

Figure 39:
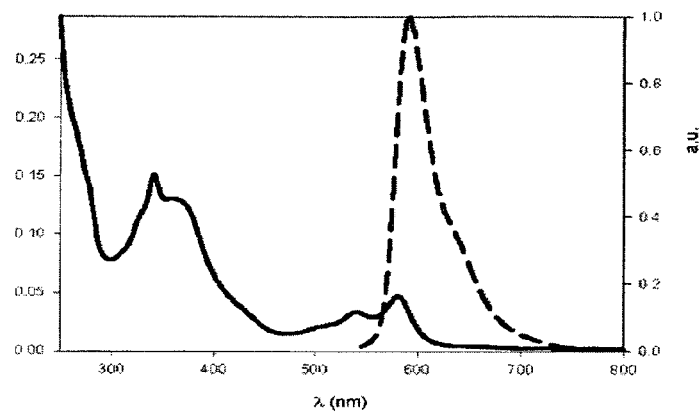
FIG. 39 shows the absorbance spectrum (solid line) and the fluorescence emission spectrum (dashed line) of particles containing 8-oxo-3-propylaminotriethoxysilyl-8H-acenaphtho[1,2-b]pyrrol-9-carbonitrile.

FIG. 39 shows the absorption spectrum (solid line) and the fluorescence emission spectrum (dotted line) of particles containing 8-oxo-3-propylaminotriethoxysilyl-8H-acenaphtho [1,2-b]pyrrol-9-carbonitrile ($\lambda_{exc}$=535 nm) (the wavelengths are reported on the x-axis; absorbance—on the left—and luminescence intensity—on the right—are reported on the y-axis) in H$_2$O.

Figure 40:
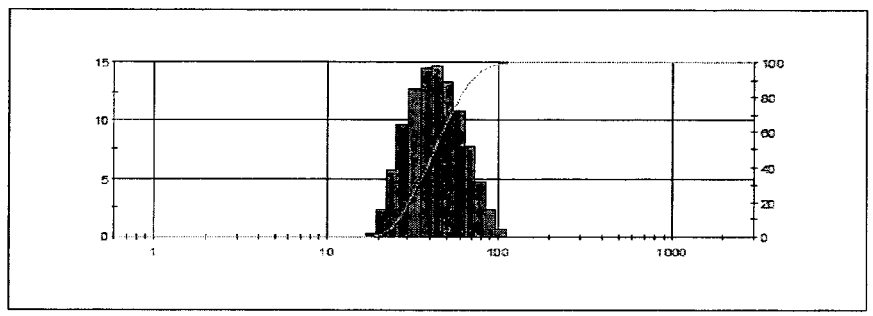
FIG. 40 shows the dimensional distribution obtained by means of DLS (dynamic light scattering) technique of the particles containing 8-oxo-3-propylaminotriethoxysilyl-8H-acenaphtho[1,2-b]pyrrol-9-carbonitrile in water (the diameter expressed in nm is reported on the x-axis)

FIG. 40 shows the dimensional distribution obtained via the DLS (dynamic light scattering) technique for particles containing 8-oxo-3-propylaminotriethoxysilyl-8H-acenaphtho[1,2-b]pyrrol-9-carbonitrile in H$_2$O.

Example 31

Preparation of Particles

Fluorescein sodium salt was used as the active compound.

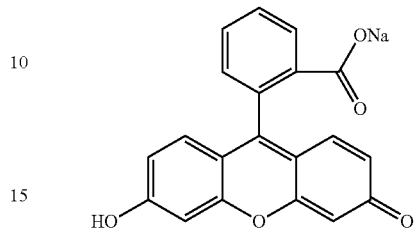

The experimental procedure described in the supporting information of the article *J. Am. Chem. Soc.* 2006, 128, 6447-6453 (paragraph 2.4, page S4) was followed.

Example 32

Preparation of Particles

Red Nile was used as the active compound.

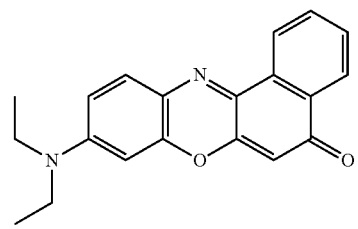 [SMILES: CCN(CC)c1ccc2nc3c4ccccc4c(=O)cc-3oc2c1]

The experimental procedure described in the supporting information of the article *J. Am. Chem. Soc.* 2006, 128, 6447-6453 (paragraph 2.4, page S4) was followed.

Example 33

Leaching Tests

Reaction mixtures from examples 29 (with fluorescein sodium salt, methanol was used as the organic solvent) and 31 were diluted up to 50 mL with Milli-Q water and subjected to dia-ultrafiltration (regenerated cellulose membrane, cut-off 100 kDa, diameter 47 mm, 75 mL Millipore cell, P=0.5 atm N$_2$, flux of filtrated solution about 0.25 mL/min, volume of filtrated solution 3000 mL, pH 7.2).

Figure 41:
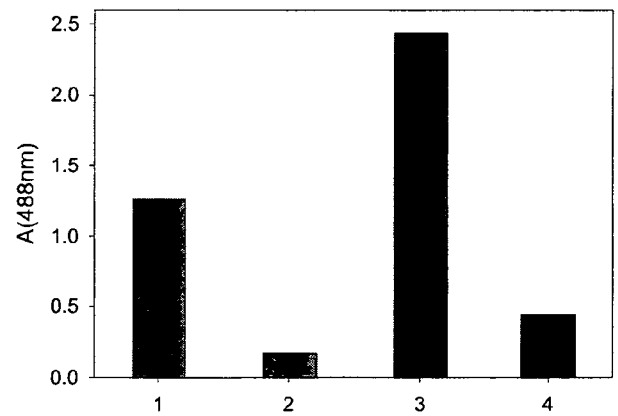
FIG. 41 shows the absorbance of particles in accordance with the invention (columns 3 and 4) and of particles used for comparison (column 1 and 2) containing fluorescein.

The absorbance of the particles of example 31 (FIG. 41, the absorbance at 488 nm is reported on the y-axis), before and after ultrafiltration (column 1 and 2) and of example 29 before and after ultrafiltration (column 3 and 4) was evaluated. As one can notice, the amount of active compound that is kept inside nanoparticles after a prolonged dia-ultrafiltration treatment is different in the two cases. The adoption of the methodology of example 29 allows to hold approximately a double quantity of active compound inside the nanoparticles.

Besides, one can notice that the methodology illustrated in example 29 requires far less time with respect to the methodology in example 31.

Example 34

Leaching Tests

Reaction mixtures from examples 29 (with Red Nile) and 32 were diluted up to 50 mL with Milli-Q water and subjected to dia-ultrafiltration (regenerated cellulose membrane, cut-off 100 kDa, dialysis solution PBS 1×, pH 7.2).

Figure 42:
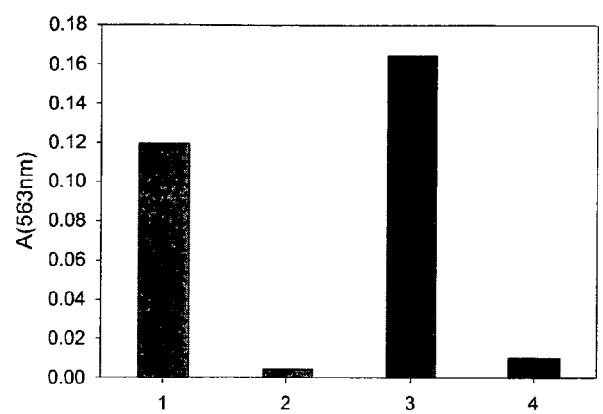
FIG. 42 shows the absorbance of particles in accordance with the invention (columns 3 and 4) and of particles used for comparison (columns 1 and 2) containing Red Nile.

The absorbance of the particles of example 32 (FIG. 42, the absorbance at 563 nm is reported on the y-axis), before and after ultrafiltration (column 1 and 2) and of example 29 before and after ultrafiltration (column 3 and 4) was evaluated. As one can notice, the amount of active compound that is kept inside nanoparticles after a prolonged dia-ultrafiltration treatment is different in the two cases. The adoption of the methodology of example, 29 allows to hold approximately a double quantity of active compound inside the nanoparticles.

Besides, one can notice that the methodology illustrated in example 29 requires far less time with respect to the methodology in example 32.

Example 35

Tests of In Vivo Imaging

Particles that can be used in this kind of experiments must have absorption and emission wavelengths in a region of the electromagnetic spectrum where tissues are transparent to light radiations (X 650-700 nm). For this reason, the utilization of particles containing active compounds like cyanines CY7 and CY5, which absorb and emit in the infrared region, is particularly advantageous.

Particles obtained in accordance with example 29 containing the cyanine CY7ClBIEt (average total diameter nm), have been used for the following tests. For these applications, samples were subjected to dialysis and/or ultrafiltration and conveniently diluted with a PBS 10× buffer in order to reach a pH value of 7.2.

Images were acquired on nude athymic nu/nu female mice (HSD Athymic Nude Fox1nu-homozygotes) from 3 to 4 weeks old. Solutions of particles containing cyanine CY7ClBIEt were used in the experiments with a dosage of 0.005-0.010 ml per g of body weight of the animal (200 μL, approximate concentration of particles: $2 \times 10^{-7}$ M per liter of physiological buffer PBS 1× at pH 7.2).

Figure 43:
FIG. 43 shows three images acquired during an in vivo imaging test on an athymic nu/nu mouse with particles containing the CY7ClBIEt cyanine (conc. 0.1% in mol vs. mol of TEOS)

In FIG. 43, one can notice the good intensity of the luminescence signal and its quite uniform distribution in the organism, with accumulation areas in some organs (liver). On the left is reported the image before the inoculation, in the middle the image right after the inoculation, and on the right the image 3 hours and 20 minutes after the inoculation (images were acquired with exc./em.—ICG/ICG (Indocyanine Green) filters).

For comparison, images obtained in similar conditions were also acquired with a commercial product, which is commonly used for this kind of experiments, that is Quantum Dots 800 (QDs 800), sold by Invitrogen®.

Quantum dots are nanocrystals of semiconductor materials (for example CdSe, CdS, PbS, etc. . . . ) characterized by a broad absorption spectrum and quite narrow emission spectra, with a maximum which depends on the dimension and on the composition of the nanocrystal. Quantum dots are commercially available and are characterized by a number which indicates the maximum wavelength in the fluorescence emission spectrum.

Figure 44:
FIG. 44 shows three images acquired during an in vivo imaging test on an athymic nu/nu mouse with commercial particles (QDs 800 by Invitrogen®)

The image shown in FIG. 44 was acquired injecting a 200 μL sample with a concentration of about $4 \times 10^{-7}$ M QDs 800 per liter. On the left is reported the image before the inoculation, in the middle the image right after the inoculation, and on the right the image 3 hours and 20 minutes after the inoculation (images were acquired with exc./em.—ICG/ICG (Indocyanine Green) filters).

Next to the series of images acquired during each experiment is shown a luminescence intensity scale in pseudo-colors. The recorded intensities in the images obtained with our samples, also considering the lower concentration of luminescent particles inoculated, are much greater in comparison with the ones recorded in the experiment with QDs 800.

The invention claimed is:

1. Particle comprising a micelle, which, on its turn, has a substantially hydrophilic shell and a substantially hydrophobic central portion; a core, which is located in the area of the micelle central portion and comprises a silicate network; and at least an active compound; the micelle comprising a plurality of molecules of at least a surfactant, which molecules comprise at least a molecule of a functionalized surfactant having the following structure:

$M^1$-Hydro$^1$-Lipo-Hydro$^2$-$M^2$ wherein Lipo represent a substantially hydrophobic chain; Hydro$^1$ and Hydro$^2$ represent, independently of each other, a respective substantially hydrophilic chain; $M^1$ has the following structure:

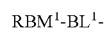

RBM$^1$-BL$^1$- wherein RBM$^1$ represents a recognition bio-molecule, BL$^1$ represents a bridge linker chosen in the group consisting of:

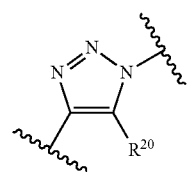

and amide;

$M^2$ is selected in the group consisting of: —H, —OH and the following structure:

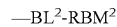

—BL$^2$-RBM$^2$ wherein RBM$^2$ represents a recognition bio-molecule, BL$^2$ represents a bridge linker chosen in the group consisting of:

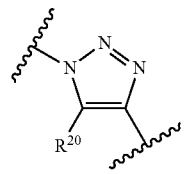

and amide; R$^{20}$ being chosen in the group consisting of: —H, a linear alkyl group, a cyclo-alkyl group, an aromatic ring, a hetero-group; the surfactant and the active compound are different from each other; the molecules of the surfactant comprise a non functionalized surfactant having the following structure:

Hydro$^3$-Lipo$^1$-Hydro$^4$ wherein Lipo$^1$ represent a substantially hydrophobic chain; Hydro$^3$ and Hydro$^4$ represent, independently of each other, a respective substantially hydrophilic chain; the molar ratio between the non functionalized surfactant and the functionalized surfactant is at least 3/1.

2. Particle according to claim 1, wherein BL$^1$ represents a bridge linker chosen in the group consisting of:

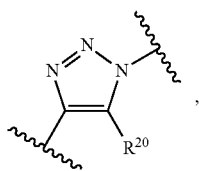
,

—NHCO— and —NHCOR$^{19}$COO—;

BL$^2$ representing a bridge linker chosen in the group consisting of:

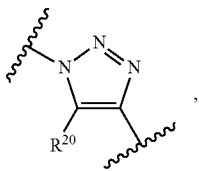
,

—OR$^{17}$CONH—, and —OCOR$^{19}$CONH—;

R$^{17}$ and R$^{19}$ being, independently of each other, a C$_1$-C$_4$ alkyl group; R$^{20}$ being chosen in the group consisting of: —H, a C$_1$-C$_4$ alkyl group; the molar ratio between the non functionalized surfactant and the functionalized surfactant is up to 100/1.

3. Particle according to claim 1, wherein the recognition bio-molecule is chosen in the group consisting of: oligopeptide, polypeptide, oligonucleotide.

4. Particle according to claim 1, wherein M$^1$ and M$^2$ are identical to each other.

5. Particle according to claim 1, wherein the active compound is located in the area of the core; Lipo being substantially lipophilic; Hydro$^1$ and Hydro$^2$ being more soluble in water than in ethanol.

6. Particle according to claim 1, wherein the active compound is an emitting compound.

7. Particle according to claim 1, wherein the active compound is covalently bound to the silicate network.

8. Particle according to claim 1, and having an average hydrodynamic diameter in water lower than approximately 100 nm, in particular from approximately 40 nm to approximately 10 nm.

9. Particle according to claim 1, wherein the core has a diameter lower than approximately 30 nm, in particular from approximately 5 to approximately 15 nm.

10. Particle according to claim 1, wherein the micelle consists of a plurality of molecules of the functionalized surfactant.

11. Particle according to claim 1, wherein Hydro$^1$ represents a chain

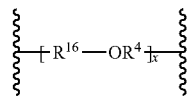

wherein x is from 40 to 130 and R$^4$ is a linear C$_1$-C$_3$ alkyl group; R$^{16}$ is a C$_1$-C$_4$ alkyl group; Hydro$^2$ represents a chain

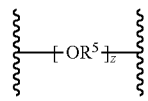

wherein z is from 40 to 130 and R$^5$ is a linear C$_1$-C$_3$ alkyl group; Lipo represents a chain

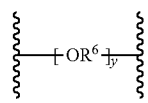

wherein y is from 20 to 85, R$^6$ is a branched C$_3$-C$_4$ alkyl group; with the proviso that, where M$^1$ is —COOH, M$^2$ is —OR$^{17}$COOH.

12. Particle according to claim 11, wherein Hydro$^1$ represents a chain

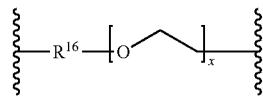

wherein x is from 80 to 120; R$^{16}$ is a linear C$_1$-C$_3$ alkyl group:
Hydro$^2$ represents a chain

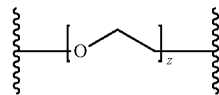

wherein z is from 80 to 120; Lipo represents a chain

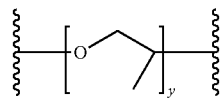

wherein y is from 50 to 80.

13. Particle according to claim 11, wherein R$^{16}$ is chosen in the group consisting of: —CH$_2$— and —(CH$_2$)$_2$—.

14. Particle according to claim 1, wherein the functionalized surfactant has an average molecular weight of at least 6 KDa; the ratios between the Lipo average molecular weight and the Hydro$^1$ average molecular weight and between the Lipo average molecular weight and the Hydro$^2$ average molecular weight being, independently of each other, from approximately 0.4 to approximately 2.0.

15. Particle according to claim 1, wherein said molecules of surfactant comprise a non-functionalized surfactant; the ratio between the non-functionalized and functionalized surfactants is lower than 200/1, in particular from 100/1 to 1/100.

16. A particle according to claim 1, obtainable by a method comprising a reaction step during which a plurality of molecules of at least an alkoxysilane are silanazed in the presence of at least an active compound, water and a plurality of molecules of at least a functionalized surfactant; the alkoxysilane being chosen between a tetraalkoxysilane and a trialkoxysilane; the functionalized surfactant being as defined in claim 1 wherein, during the reaction step, the molecules of alkoxysilane are silanazed together with the active compound; wherein, during the reaction step, the molecules of alkoxysilane are silanazed together with the active compound.

* * * * *

UNITED STATES PATENT AND TRADEMARK OFFICE
CERTIFICATE OF CORRECTION

PATENT NO. : 8,771,642 B2  
APPLICATION NO. : 13/056752  
DATED : July 8, 2014  
INVENTOR(S) : Sara Bonacchi et al.

It is certified that error appears in the above-identified patent and that said Letters Patent is hereby corrected as shown below:

In the Claims

At Column 61, line 5, claim 16, "silanazed" should be -- silanized --.

At Column 61, line 11, claim 16, "silanazed" should be -- silanized --.

At Column 61, line 13, claim 16, "silanazed" should be -- silanized --.

Signed and Sealed this  
Twenty-ninth Day of September, 2015

Michelle K. Lee  
*Director of the United States Patent and Trademark Office*